(12) United States Patent
Ryan et al.

(10) Patent No.: US 11,827,709 B2
(45) Date of Patent: Nov. 28, 2023

(54) ANTI-AVB6 ANTIBODIES AND ANTIBODY-DRUG CONJUGATES

(71) Applicant: SEAGEN INC., Bothell, WA (US)

(72) Inventors: Maureen Ryan, Bellevue, WA (US); Lori Westendorf, Snohomish, WA (US); Eric Bradley Meyer, Hayward, CA (US); Heather Jean Kostner, Bothell, WA (US)

(73) Assignee: Seagen Inc., Bothell, WA (US)

( * ) Notice: Subject to any disclaimer, the term of this patent is extended or adjusted under 35 U.S.C. 154(b) by 250 days.

(21) Appl. No.: 17/112,533

(22) Filed: Dec. 4, 2020

(65) Prior Publication Data

US 2021/0198367 A1    Jul. 1, 2021

Related U.S. Application Data

(60) Provisional application No. 63/012,584, filed on Apr. 20, 2020, provisional application No. 62/943,959, filed on Dec. 5, 2019.

(51) Int. Cl.
| | |
|---|---|
| C07K 16/28 | (2006.01) |
| A61K 47/68 | (2017.01) |
| A61K 38/07 | (2006.01) |
| A61K 47/54 | (2017.01) |
| A61K 45/06 | (2006.01) |
| A61P 35/00 | (2006.01) |
| A61K 47/65 | (2017.01) |

(52) U.S. Cl.
CPC .......... *C07K 16/2839* (2013.01); *A61K 38/07* (2013.01); *A61K 45/06* (2013.01); *A61K 47/545* (2017.08); *A61K 47/65* (2017.08); *A61K 47/6803* (2017.08); *A61K 47/6849* (2017.08); *A61P 35/00* (2018.01); *C07K 2317/24* (2013.01)

(58) Field of Classification Search
CPC ............ C07K 16/2839; C07K 2317/24; A61K 38/07; A61K 45/06; A61K 47/545; A61K 47/65; A61K 47/6803; A61K 47/6849; A61P 35/00
See application file for complete search history.

(56) References Cited

U.S. PATENT DOCUMENTS

| | | | |
|---|---|---|---|
| 5,962,643 A | 10/1999 | Sheppard et al. | |
| 7,150,871 B2 | 12/2006 | Huang et al. | |
| 7,465,449 B2 | 12/2008 | Violette et al. | |
| 7,943,742 B2 | 5/2011 | Violette et al. | |
| 8,398,975 B2 | 3/2013 | Rinkenberger et al. | |
| 8,491,901 B2 * | 7/2013 | Imai | A61P 37/06 424/145.1 |
| 8,496,932 B2 * | 7/2013 | Clegg | A61P 7/00 435/325 |
| 9,845,363 B2 * | 12/2017 | Pritsker | A61P 11/00 |
| 10,633,456 B1 * | 4/2020 | Boyd-Kirkup | C07K 16/464 |
| 10,858,427 B2 * | 12/2020 | Dong | A61P 37/00 |
| 11,479,612 B2 * | 10/2022 | Moon | C07K 16/2863 |
| 2004/0048312 A1 | 3/2004 | Li et al. | |
| 2005/0090648 A1 | 4/2005 | Tsurushita et al. | |
| 2005/0287538 A1 | 12/2005 | Cheung et al. | |
| 2006/0204506 A1 | 9/2006 | Ebel et al. | |
| 2009/0028853 A1 | 1/2009 | Sheppard et al. | |
| 2011/0059469 A1 | 3/2011 | Aburatani et al. | |
| 2011/0046309 A1 | 4/2011 | Cho et al. | |
| 2011/0294982 A1 | 12/2011 | Vanlandschoot et al. | |
| 2012/0171699 A1 | 7/2012 | Goodman et al. | |
| 2016/0017042 A1 | 1/2016 | Violette et al. | |
| 2016/0031992 A1 | 2/2016 | Violette et al. | |
| 2016/0319032 A1 | 11/2016 | Barry et al. | |
| 2016/0376368 A1 | 12/2016 | Ryan et al. | |

FOREIGN PATENT DOCUMENTS

| | | |
|---|---|---|
| JP | 2009-500041 A | 1/2009 |
| WO | WO2003/100033 A2 | 12/2003 |
| WO | WO2006/041934 A2 | 4/2006 |
| WO | WO2006/125140 A3 | 11/2006 |
| WO | WO2007/008712 A2 | 1/2007 |
| WO | WO2007/026000 A2 | 3/2007 |
| WO | WO2008/008315 A2 | 1/2008 |
| WO | WO2008/112004 A2 | 9/2008 |
| WO | WO2008/147434 A1 | 12/2008 |
| WO | WO2011/046309 A2 | 4/2011 |
| WO | WO2013/148316 A1 | 10/2013 |
| WO | WO2014/143739 A2 | 9/2014 |
| WO | WO2014/144466 A1 | 9/2014 |
| WO | WO2019040608 A1 | 2/2019 |
| WO | WO2021113697 A1 | 6/2021 |

OTHER PUBLICATIONS

Munk, C. et al., Uniprot Submission with Accession No. D3Q6V1 [online] Nov. 30, 2010.
PCT Application No. PCT/US2020/063390, International Search Report and Written Opinion dated Mar. 23, 2021, 13 pages.
Ryan et al., Integrin alphaValpha6 is expressed on multiple solid tumors and is a potential therapeutic target for auristatin-based antibody-drug conjugates, Cancer Research, vol. 72, issue 8, suppl 1, abstract 4630, 2012.
Ryan, et al., Integrin AVB6 is Expressed on Multiple Solid Tumors and is a Potential Therapeutic Target for Auristatin-Based Antibody-Drug Conjugates poster, Abstract No. 4630, American Association of Cancer Research, Apr. 1-4, 2012, Chicago, IL.
Tanfous, N.G.B. et al., Characterization of a Novel Monoclonal Antibody with Restricted Specificity to the Free b2 Integrin aM CD11 b Subunit. Hybridoma, vol. 26(6), pp. 373-379: Table 2 abstract, 2007.

* cited by examiner

*Primary Examiner* — Daniel E Kolker
*Assistant Examiner* — Brittney E Donoghue
(74) *Attorney, Agent, or Firm* — Seagen Inc.

(57) ABSTRACT

Provided are novel anti-αvβ6 antibodies and antibody-drug conjugates and methods of using such anti-αvβ6 antibodies and antibody-drug conjugates to treat cancer.

104 Claims, 18 Drawing Sheets

Specification includes a Sequence Listing.

Alignment of h2A2 Heavy Chain Variants with Human Acceptor Sequence, IGHV1-46/HJ4.

```
                         10         20         30         40         50
                 ....|....|....|....|....|....|....|....|....|....|....|....|
m2A2 vH          EF.Q...P.LV....I......S.D.NVN..K.SN.KS...I.V...KY.T.R.
hIGHV1-46/HJ4    QVQLVQSGAEVKKPGASVKVSCKASGYTFTSYYMHWVRQAPGQGLEWMGIINPSGGSTSY
h2A2 vHA         .F.............................S.D.NVN............V...KY.T.R.
h2A2 vHB         .F.............................S.D.NVN............V...KY.T.R.
h2A2 vHC         .F.............................S.D.NVN..........I.V...KY.T.R.
h2A2 vHD         .F.............................S.D.NVN..........I.V...KY.T.R.
Kabat CDRs                                      ******              **********
IMGT CDRs                                        ++++++             +++++++

60         70         80         90        101       110
                 ....|....|....|....|....|....|....|....|....|....|....|....|....|
m2A2 vH          N...K.KA.L.V.KPS..A..Q.N.T..S....T.GLNAW......AS....
hIGHV1-46/HJ4    AQKFQGRVTMTRDTSTSTVYMELSSLRSEDTAVYYCAR---YFDYWGQGTLVTVSS
h2A2 vHA         N...K........P...................T.GLNAW............
h2A2 vHB         N...K..A.L.V.K....A..............T.GLNAW............
h2A2 vHC         N...K..A.L.V.KP..A...............T.GLNAW............
h2A2 vHD         N...K..A.L.V.KP..A...............T.GLNAW............
Kabat CDRs       *******                         ********
IMGT CDRs                                       ++++++++
```

FIGURE 3

Alignment of h2A2 Light Chain Variants with Human Acceptor Sequence, IGKV1D-33/KJ2.

```
                       10        20        30        40        50        60
                ....|....|....|....|....|....|....|....|....|....|....|....|
m2A2 vL         ........A......ET.....G..EN.YGA.....R.Q..S.Q...G.T...AD.MS.
hIGKV1D-33/KJ2  DIQMTQSPSSLSASVGDRVTITCQASQDISNYLNWYQQKPGKAPKLLIYDASNLETGVPS
h2A2 vLA        ...............................G..EN.YGA.....G.T...AD.....
h2A2 vLB        ...............................G..EN.YGA.....G.T...AD.....
h2A2 vLC        ...............................G..EN.YGA.....G.T...A......
h2A2 vLD        ...............................G..EN.YGA.....G.T...AD.....
h2A2 vLE        ..................................EN.YGA.....G.T...A......
h2A2 vLF        ..................................EN.YGA.....G.T...AD.....
h2A2 vLG        ...............................G..EN.YGA.....G.T....D.....
h2A2 vLH        ...............................G..EN.YGA.....G.T...AD.....
Kabat CDRs                                     **************       *******
IMGT CDRs                                          ++++++++                +++

70        80        90       100
                ....|....|....|....|....|....|....|....|....
m2A2 vL         .........RQYS.K....H.D.V......NVLTT......G..
hIGKV1D-33/KJ2  RFSGSGSGTDFTFTISSLQPEDIATYYCQQYDNLPYTFGQGTKLEIK
h2A2 vLA        ..........R.Y.................NVLTT.........
h2A2 vLB        ..........R.Y.................NVLTT.........
h2A2 vLC        ............Y.................NVLTT.........
h2A2 vLD        ..........R.Y.................NVLTT.........
h2A2 vLE        ............Y.................NVLTT.........
h2A2 vLF        ..........R.Y.................NVLTT.........
h2A2 vLG        ..........R.Y.................NVLTT.........
h2A2 vLH        ..........R...................NVLTT.........
Kabat CDRs                                    ***********
IMGT CDRs                                       +++++++++
```

FIGURE 4

SEQUENCE LISTING

<160> NUMBER OF SEQ ID NOS: 45

<210> SEQ ID NO 1
<211> LENGTH: 116
<212> TYPE: PRT
<213> ORGANISM: Artificial Sequence
<220> FEATURE:
<223> OTHER INFORMATION: m2A2 vH

<400> SEQUENCE: 1

```
Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Val Asn Trp Val Lys Gln Ser Asn Gly Lys Ser Leu Glu Trp Ile
        35                  40                  45

Gly Val Ile Asn Pro Lys Tyr Gly Thr Thr Arg Tyr Asn Gln Lys Phe
    50                  55                  60

Lys Gly Lys Ala Thr Leu Thr Val Asp Lys Pro Ser Ser Thr Ala Tyr
65                  70                  75                  80

Met Gln Leu Asn Ser Leu Thr Ser Glu Asp Ser Ala Val Tyr Tyr Cys
                85                  90                  95

Thr Arg Gly Leu Asn Ala Trp Asp Tyr Trp Gly Gln Gly Ala Ser Val
            100                 105                 110

Thr Val Ser Ser
        115
```

<210> SEQ ID NO 2
<211> LENGTH: 98
<212> TYPE: PRT
<213> ORGANISM: Artificial Sequence
<220> FEATURE:
<223> OTHER INFORMATION: mIGHV1-39 (closest murine germline V-gene)

<400> SEQUENCE: 2

Glu Phe Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Asp Tyr
            20                  25                  30

Asn Met Asn Trp Val Lys Gln Ser Asn Gly Lys Ser Leu Glu Trp Ile
        35                  40                  45

Gly Val Ile Asn Pro Asn Tyr Gly Thr Thr Ser Tyr Asn Gln Lys Phe
    50                  55                  60

Lys Gly Lys Ala Thr Leu Thr Val Asp Gln Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg

<210> SEQ ID NO 3
<211> LENGTH: 113
<212> TYPE: PRT
<213> ORGANISM: Artificial Sequence
<220> FEATURE:
<223> OTHER INFORMATION: hIGHV1-46/HJ4

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Asp Tyr Trp Gly Gln Gly Thr Leu Val Thr Val Ser
                100                 105                 110

Ser

<210> SEQ ID NO 4
<211> LENGTH: 116
<212> TYPE: PRT
<213> ORGANISM: Artificial Sequence
<220> FEATURE:
<223> OTHER INFORMATION: h2A2 vHA

<400> SEQUENCE: 4

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Val Asn Trp Val Arg Gln Ala Pro Gly Gln Gly Leu Glu Trp Met
        35                  40                  45

Gly Val Ile Asn Pro Lys Tyr Gly Thr Thr Arg Tyr Asn Gln Lys Phe
    50                  55                  60

```
Lys Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
            100                 105                 110

Thr Val Ser Ser
            115

<210> SEQ ID NO 5
<211> LENGTH: 116
<212> TYPE: PRT
<213> ORGANISM: Artificial Sequence
<220> FEATURE:
<223> OTHER INFORMATION: h2A2 vHB

<400> SEQUENCE: 5

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Asn Val Asn Trp Val Arg Gln Ala Pro Gly Gln Gly Leu Glu Trp Met
            35                  40                  45

Gly Val Ile Asn Pro Lys Tyr Gly Thr Thr Arg Tyr Asn Gln Lys Phe
        50                  55                  60

Lys Gly Arg Val Thr Met Thr Arg Asp Thr Pro Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
            100                 105                 110

Thr Val Ser Ser
            115

<210> SEQ ID NO 6
<211> LENGTH: 116
<212> TYPE: PRT
<213> ORGANISM: Artificial Sequence
<220> FEATURE:
<223> OTHER INFORMATION: h2A2 vHC

<400> SEQUENCE: 6

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Asn Val Asn Trp Val Arg Gln Ala Pro Gly Gln Gly Leu Glu Trp Ile
            35                  40                  45

Gly Val Ile Asn Pro Lys Tyr Gly Thr Thr Arg Tyr Asn Gln Lys Phe
        50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Thr Arg Gly Leu Asn Ala Trp Asp Tyr Trp Gly Gln Gly Thr Leu Val
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: h2A2 vHD

<400> SEQUENCE: 7

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Val Asn Trp Val Arg Gln Ala Pro Gly Gln Gly Leu Glu Trp Ile
        35                  40                  45

Gly Val Ile Asn Pro Lys Tyr Gly Thr Thr Arg Tyr Asn Gln Lys Phe
    50                  55                  60

Lys Gly Arg Ala Thr Leu Thr Val Asp Lys Pro Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
            100                 105                 110

Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: m2A2 vL

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Phe Lys Ile Ser Ser Leu His Pro
65                  70                  75                  80

Asp Asp Val Ala Thr Tyr Tyr Cys Gln Asn Val Leu Thr Thr Pro Tyr
                85                  90                  95

Thr Phe Gly Gly Gly Thr Lys Leu Glu Ile Lys
            100                 105

<210> SEQ ID NO 9
<211> LENGTH: 95
<212> TYPE: PRT
<213> ORGANISM: Artificial Sequence
<220> FEATURE:
<223> OTHER INFORMATION: mIGKV12-89 (closest murine germline V-gene)
```

```
<400> SEQUENCE: 9

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Thr Pro
                85                  90                  95

<210> SEQ ID NO 10
<211> LENGTH: 107
<212> TYPE: PRT
<213> ORGANISM: Artificial Sequence
<220> FEATURE:
<223> OTHER INFORMATION: hIGKV1D-33/KJ2

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Tyr
                85                  90                  95

Thr Phe Gly Gln Gly Thr Lys Leu Glu Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: h2A2 vLA

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95
```

Thr Phe Gly Gln Gly Thr Lys Leu Glu Ile Lys
            100                 105

<210> SEQ ID NO 12
<211> LENGTH: 107
<212> TYPE: PRT
<213> ORGANISM: Artificial Sequence
<220> FEATURE:
<223> OTHER INFORMATION: h2A2 vLB

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: h2A2 vLC

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Thr Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 14
<211> LENGTH: 107
<212> TYPE: PRT
<213> ORGANISM: Artificial Sequence
<220> FEATURE:
<223> OTHER INFORMATION: h2A2 vLD

<400> SEQUENCE: 14

Asp Ile Gln Met Thr Gln Ser Pro Ser Ser Leu Ser Ala Ser Val Gly
1               5                   10                  15

-continued

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 15
<211> LENGTH: 107
<212> TYPE: PRT
<213> ORGANISM: Artificial Sequence
<220> FEATURE:
<223> OTHER INFORMATION: h2A2 vLE

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 16
<211> LENGTH: 107
<212> TYPE: PRT
<213> ORGANISM: Artificial Sequence
<220> FEATURE:
<223> OTHER INFORMATION: h2A2 vLF

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 17
<211> LENGTH: 107
<212> TYPE: PRT
<213> ORGANISM: Artificial Sequence
<220> FEATURE:
<223> OTHER INFORMATION: h2A2 vLG

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Glu Asp Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 18
<211> LENGTH: 107
<212> TYPE: PRT
<213> ORGANISM: Artificial Sequence
<220> FEATURE:
<223> OTHER INFORMATION: h2A2 vLH

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Asp Phe Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys
            100                 105

<210> SEQ ID NO 19
<211> LENGTH: 446
<212> TYPE: PRT
<213> ORGANISM: Artificial Sequence
<220> FEATURE:
<223> OTHER INFORMATION: h2A2 HA heavy chain

<400> SEQUENCE: 19

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

```
Asn Val Asn Trp Val Arg Gln Ala Pro Gly Gln Gly Leu Glu Trp Met
         35                  40                  45

Gly Val Ile Asn Pro Lys Tyr Gly Thr Thr Arg Tyr Asn Gln Lys Phe
 50                  55                  60

Lys Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Thr Arg Gly Leu Asn Ala Trp Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 20
<211> LENGTH: 446
<212> TYPE: PRT
<213> ORGANISM: Artificial Sequence
<220> FEATURE:
<223> OTHER INFORMATION: h2A2 HB heavy chain

<400> SEQUENCE: 20

```
Gln Phe Gln Leu Val Gln Ser Gly Ala Glu Val Lys Pro Gly Ala
1               5                   10                  15

Ser Val Lys Val Ser Cys Lys Ala Ser Gly Tyr Ser Phe Thr Asp Tyr
            20                  25                  30

Asn Val Asn Trp Val Arg Gln Ala Pro Gly Gln Gly Leu Glu Trp Met
        35                  40                  45

Gly Val Ile Asn Pro Lys Tyr Gly Thr Thr Arg Tyr Asn Gln Lys Phe
    50                  55                  60

Lys Gly Arg Val Thr Met Thr Arg Asp Thr Pro Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365
```

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 21
<211> LENGTH: 446
<212> TYPE: PRT
<213> ORGANISM: Artificial Sequence
<220> FEATURE:
<223> OTHER INFORMATION: h2A2 HC heavy chain

<400> SEQUENCE: 21

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Asn Val Asn Trp Val Arg Gln Ala Pro Gly Gln Gly Leu Glu Trp Ile
        35                  40                  45

Gly Val Ile Asn Pro Lys Tyr Gly Thr Thr Arg Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

```
Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 22
<211> LENGTH: 446
<212> TYPE: PRT
<213> ORGANISM: Artificial Sequence
<220> FEATURE:
<223> OTHER INFORMATION: h2A2 HD heavy chain

<400> SEQUENCE: 22

Gln Phe Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Asn Val Asn Trp Val Arg Gln Ala Pro Gly Gln Gly Leu Glu Trp Ile
            35                  40                  45

Gly Val Ile Asn Pro Lys Tyr Gly Thr Thr Arg Tyr Asn Gln Lys Phe
50                  55                  60

Lys Gly Arg Ala Thr Leu Thr Val Asp Lys Pro Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Leu Asn Ala Trp Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

Lys Val Asp Lys Lys Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 23
<211> LENGTH: 214
<212> TYPE: PRT
<213> ORGANISM: Artificial Sequence
<220> FEATURE:
<223> OTHER INFORMATION: h2A2 LA light chain

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 24
<211> LENGTH: 214
<212> TYPE: PRT
<213> ORGANISM: Artificial Sequence
<220> FEATURE:
<223> OTHER INFORMATION: h2A2 LB light chain

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Pro Gly Lys Ala Pro Lys Leu Leu Ile
                35                  40                  45

Tyr Gly Ala Thr Asn Leu Ala Asp Gly Val Pro Ser Arg Phe Ser Gly
        50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 25
<211> LENGTH: 214
<212> TYPE: PRT
<213> ORGANISM: Artificial Sequence
<220> FEATURE:
<223> OTHER INFORMATION: h2A2 LC light chain
```

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Thr Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 26
<211> LENGTH: 214
<212> TYPE: PRT
<213> ORGANISM: Artificial Sequence
<220> FEATURE:
<223> OTHER INFORMATION: h2A2 LD light chain

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 27
<211> LENGTH: 214
<212> TYPE: PRT
<213> ORGANISM: Artificial Sequence
<220> FEATURE:
<223> OTHER INFORMATION: h2A2 LE light chain

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
                20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
        50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
        210

<210> SEQ ID NO 28
<211> LENGTH: 214
<212> TYPE: PRT
<213> ORGANISM: Artificial Sequence
<220> FEATURE:
<223> OTHER INFORMATION: h2A2 LF light chain
```

-continued

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 214
<212> TYPE: PRT
<213> ORGANISM: Artificial Sequence
<220> FEATURE:
<223> OTHER INFORMATION: h2A2 LG light chain

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Glu Asp Gly Val Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 214
<212> TYPE: PRT
<213> ORGANISM: Artificial Sequence
<220> FEATURE:
<223> OTHER INFORMATION: h2A2 LH light chain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Arg Asp Phe Thr Phe Thr Ile Ser Ser Leu Gln Pro
65                  70                  75                  80

Glu Asp Ile Ala Thr Tyr Tyr Cys Gln Asn Val Leu Thr Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 5
<212> TYPE: PRT
<213> ORGANISM: Artificial Sequence
<220> FEATURE:
<223> OTHER INFORMATION: HA, HB, HC, HD CDR1, KABAT
```

```
<400> SEQUENCE: 31

Asp Tyr Asn Val Asn
1               5

<210> SEQ ID NO 32
<211> LENGTH: 17
<212> TYPE: PRT
<213> ORGANISM: Artificial Sequence
<220> FEATURE:
<223> OTHER INFORMATION: HA, HB, HC, HD CDR2, KABAT

<400> SEQUENCE: 32

Val Ile Asn Pro Lys Tyr Gly Thr Thr Arg Tyr Asn Gln Lys Phe Lys
1               5                   10                  15

Gly

<210> SEQ ID NO 33
<211> LENGTH: 7
<212> TYPE: PRT
<213> ORGANISM: Artificial Sequence
<220> FEATURE:
<223> OTHER INFORMATION: HA, HB, HC, HD CDR3, KABAT

<400> SEQUENCE: 33

Gly Leu Asn Ala Trp Asp Tyr
1               5

<210> SEQ ID NO 34
<211> LENGTH: 8
<212> TYPE: PRT
<213> ORGANISM: Artificial Sequence
<220> FEATURE:
<223> OTHER INFORMATION: HA, HB, HC, HD CDR1, IMGT

<400> SEQUENCE: 34

Gly Tyr Ser Phe Thr Asp Tyr Asn
1               5

<210> SEQ ID NO 35
<211> LENGTH: 8
<212> TYPE: PRT
<213> ORGANISM: Artificial Sequence
<220> FEATURE:
<223> OTHER INFORMATION: HA, HB, HC, HD CDR2, IMGT

<400> SEQUENCE: 35

Ile Asn Pro Lys Tyr Gly Thr Thr
1               5

<210> SEQ ID NO 36
<211> LENGTH: 9
<212> TYPE: PRT
<213> ORGANISM: Artificial Sequence
<220> FEATURE:
<223> OTHER INFORMATION: HA, HB, HC, HD CDR3, IMGT

<400> SEQUENCE: 36

Thr Arg Gly Leu Asn Ala Trp Asp Tyr
1               5

<210> SEQ ID NO 37
<211> LENGTH: 11
<212> TYPE: PRT
<213> ORGANISM: Artificial Sequence
<220> FEATURE:
<223> OTHER INFORMATION: LA, LB, LC, LD, LG, LH CDR1, KABAT
```

```
<400> SEQUENCE: 37

Gly Ala Ser Glu Asn Ile Tyr Gly Ala Leu Asn
1               5                   10

<210> SEQ ID NO 38
<211> LENGTH: 7
<212> TYPE: PRT
<213> ORGANISM: Artificial Sequence
<220> FEATURE:
<223> OTHER INFORMATION: LA, LB, LD, LE, LH CDR2, KABAT

<400> SEQUENCE: 38

Gly Ala Thr Asn Leu Ala Asp
1               5

<210> SEQ ID NO 39
<211> LENGTH: 9
<212> TYPE: PRT
<213> ORGANISM: Artificial Sequence
<220> FEATURE:
<223> OTHER INFORMATION: LA, LB, LC, LD, LE, LF, LG, LH CDR3, KABAT

<400> SEQUENCE: 39

Gln Asn Val Leu Thr Thr Pro Tyr Thr
1               5

<210> SEQ ID NO 40
<211> LENGTH: 11
<212> TYPE: PRT
<213> ORGANISM: Artificial Sequence
<220> FEATURE:
<223> OTHER INFORMATION: LE, LF CDR1, KABAT

<400> SEQUENCE: 40

Gln Ala Ser Glu Asn Ile Tyr Gly Ala Leu Asn
1               5                   10

<210> SEQ ID NO 41
<211> LENGTH: 7
<212> TYPE: PRT
<213> ORGANISM: Artificial Sequence
<220> FEATURE:
<223> OTHER INFORMATION: LC, LF CDR2, KABAT

<400> SEQUENCE: 41

Gly Ala Thr Asn Leu Ala Thr
1               5

<210> SEQ ID NO 42
<211> LENGTH: 7
<212> TYPE: PRT
<213> ORGANISM: Artificial Sequence
<220> FEATURE:
<223> OTHER INFORMATION: LG CDR2, KABAT

<400> SEQUENCE: 42

Gly Ala Thr Asn Leu Glu Asp
1               5

<210> SEQ ID NO 43
<211> LENGTH: 6
<212> TYPE: PRT
<213> ORGANISM: Artificial Sequence
<220> FEATURE:
<223> OTHER INFORMATION: LA, LB, LC, LD, LE, LF, LG, LH CDR1, IMGT
```

```
<400> SEQUENCE: 43

Glu Asn Ile Tyr Gly Ala
1               5

<210> SEQ ID NO 44
<211> LENGTH: 3
<212> TYPE: PRT
<213> ORGANISM: Artificial Sequence
<220> FEATURE:
<223> OTHER INFORMATION: LA, LB, LC, LD, LE, LF, LG, LH CDR2, IMGT

<400> SEQUENCE: 44

Gly Ala Thr
1

<210> SEQ ID NO 45
<211> LENGTH: 9
<212> TYPE: PRT
<213> ORGANISM: Artificial Sequence
<220> FEATURE:
<223> OTHER INFORMATION: LA, LB, LC, LD, LE, LF, LG, LH CDR3, IMGT

<400> SEQUENCE: 45

Gln Asn Val Leu Thr Thr Pro Tyr Thr
1               5
```

ANTI-AVB6 ANTIBODIES AND ANTIBODY-DRUG CONJUGATES

CROSS REFERENCE TO RELATED APPLICATIONS

This application claims the benefit of U.S. Provisional App. No. 62/943,959 filed Dec. 5, 2019 and U.S. Provisional App. No. 63/012,584 filed Apr. 20, 2020, each of which is incorporated by reference in its entirety for all purposes.

REFERENCE TO A SEQUENCE LISTING

This application includes an electronic sequence listing in a file named AVB6-00212_ST25 created on Nov. 16, 2020 and containing 52 KB, which is hereby incorporated by reference.

TECHNICAL FIELD

The present invention relates to novel anti-αvβ6 antibodies and antibody-drug conjugates and methods of using such anti-αvβ6 antibodies and antibody-drug conjugates to treat cancer.

BACKGROUND

αvβ6, which is also known as alpha-v beta-6, is a cell adhesion receptor that binds extracellular matrix proteins such as fibronectin. αvβ6 is composed of an alpha v subunit and a beta 6 subunit, and is upregulated in multiple cancers, including non-small cell lung cancer (NSCLC).

NSCLC is the most common type of lung cancer. In the past year, over 200,000 people were diagnosed with lung cancer, which is the leading cause of cancer death. Therefore, there is a need for improved treatments for NSCLC.

All references cited herein, including patent applications, patent publications, and scientific literature, are herein incorporated by reference in their entirety, as if each individual reference were specifically and individually indicated to be incorporated by reference.

SUMMARY

Provided herein are anti-αvβ6 antibodies and αvβ6-directed antibody-drug conjugates (ADCs). Also provided herein are methods of using anti-αvβ6-directed antibodies and ADCs to treat αvβ6-expressing disorders, including cancers. Preferred anti-αvβ6 antibodies comprise heavy chain CDR sequences of SEQ ID NOs: 31, 32, and 33 and light chain CDR sequences of SEQ ID NOs: 37, 42, and 39, as determined by Kabat numbering.

BRIEF DESCRIPTION OF THE DRAWINGS

FIG. 3 shows an alignment of the amino acid sequences of the parental murine mAb (referred to as m2A2) heavy chain variable region with select human germline acceptor (referred to as hIGHV1-46/HJ4) and humanized 2A2 heavy chain variants. Asterisks represent CDRs as determined by Kabat, and crosses represent CDRs as determined by IMGT.

FIG. 4 shows an alignment of the amino acid sequences of the parental murine mAb (referred to as m2A2) light chain variable region with select human germline acceptor (referred to as hIGKV1D-33/KJ2) and humanized 2A2 light chain variants. Asterisks represent CDRs as determined by Kabat, and crosses represent CDRs as determined by IMGT.

DETAILED DESCRIPTION

I. Definitions

Figure 1:
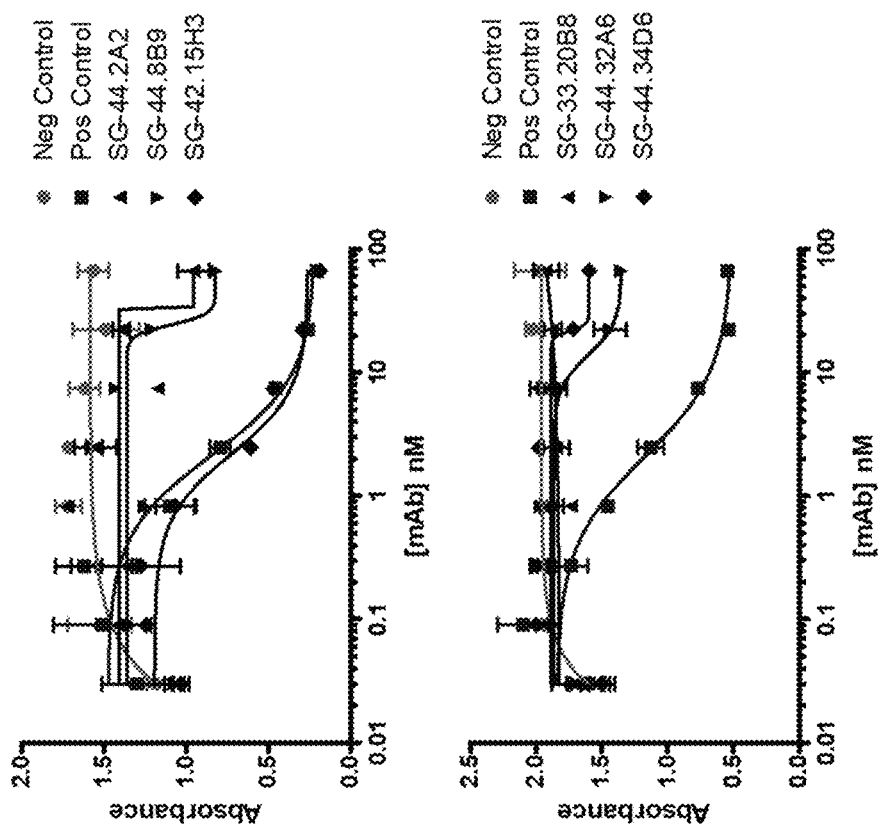
FIG. 1 shows the results of a LAP blockade ELISA assay with various anti-αvβ6 antibodies.

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that aspects and embodiments of the invention described herein include "comprising," "consisting," and "consisting essentially of" aspects and embodiments.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The terms "αvβ6," "αvb6," "alpha-v beta-6," or "P6" are used interchangeably herein, and, unless specified otherwise, include any variants, isoforms and species homologs of human αvβ6 which are generally expressed by cells or expressed on cells transfected with the αvβ6 gene.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region ($C_H$ or CH). The heavy chain constant region typically is comprised of three domains, $C_H1$, $C_H2$, and $C_H3$. The heavy chains are generally inter-connected via disulfide bonds in the so-called "hinge region." Each light chain typically is comprised of a light chain variable region (abbreviated herein as $V_L$ or VL) and a light chain constant region ($C_L$ or CL). The light chain constant region typically is comprised of one domain, $C_L$. The CL can be of κ (kappa) or λ, (lambda) isotype. The terms "constant domain" and "constant region" are used interchangeably herein. An immunoglobulin can derive from any of the commonly known isotypes, including but not limited to IgA, secretory IgA, IgG, and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody may be further subdivided into regions of hypervariability (or hypervariable regions, which may be hypervariable in sequence and/or form of structurally defined loops), also termed complementarity-determining regions (CDRs), interspersed with regions that are more conserved, termed framework regions (FRs). The terms "complementarity determining regions" and "CDRs," synonymous with "hypervariable regions" or "HVRs" are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). Within each $V_H$ and $V_L$, three CDRs and four FRs are typically arranged from amino-terminus to carboxy-terminus in the following order: FR1, CDR1, FR2, CDR2, FR3, CDR3, FR4 (See also Chothia and Lesk *J. Mot. Biol.*, 195, 901-917 (1987)).

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 min, at least about 45 min, at least about one hour (h), at least about two hours, at least about four hours, at least about eight hours, at least about 12 hours (h), about 24 hours or more, about 48 hours or more, about three, four, five, six, seven or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. An antibody may also be a bispecific antibody, diabody, multispecific antibody or similar molecule.

The term "monoclonal antibody" as used herein refers to a preparation of antibody molecules that are recombinantly produced with a single primary amino acid sequence, are produced from mouse B-cell fusions. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

An "isolated antibody" refers to an antibody that is substantially free of other antibodies having different antigenic specificities (e.g., an isolated antibody that binds specifically to αvβ6 is substantially free of antibodies that bind specifically to antigens other than αvβ6). An isolated antibody that binds specifically to αvβ6 can, however, have cross-reactivity to other antigens, such as αvβ6 molecules from different species. Moreover, an isolated antibody can be substantially free of other cellular material and/or chemicals. In one embodiment, an isolated antibody includes an antibody conjugate attached to another agent (e.g., small molecule drug). In some embodiments, an isolated anti-αvβ6 antibody includes a conjugate of an anti-αvβ6 antibody with a small molecule drug (e.g., MMAE or MMAF).

A "human antibody" (HuMAb) refers to an antibody having variable regions in which both the FRs and CDRs are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human antibodies" and "fully human antibodies" and are used synonymously.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

An "anti-antigen antibody" refers to an antibody that binds to the antigen. For example, an anti-αvβ6 antibody is an antibody that binds to the antigen αvβ6.

An "antigen-binding portion" or antigen-binding fragment" of an antibody refers to one or more fragments of an antibody that retain the ability to bind specifically to the antigen bound by the whole antibody. Examples of antibody fragments (e.g., antigen-binding fragment) include but are not limited to Fv, Fab, Fab', Fab'-SH, F(ab')$_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Percent (%) sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, SnapGene Align, or ClustalW BioEdit software. Those skilled in the art can determine appropriate parameters for aligning sequences, including any algorithms needed to achieve maximal alignment over the full length of the sequences being compared. For example, the % sequence identity of a given amino acid sequence A to, with, or against a given amino acid sequence B (which can alternatively be phrased as a given amino acid sequence A that has or comprises a certain % sequence identity to, with, or against a given amino acid sequence B) is calculated as follows:

100 times the fraction X/Y where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % sequence identity of A to B will not equal the % sequence identity of B to A.

As used herein, the terms "binding", "binds" or "specifically binds" in the context of the binding of an antibody to a pre-determined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (that is, the antibody is highly specific).

The term "$K_D$" (M), as used herein, refers to the dissociation equilibrium constant of a particular antibody-antigen interaction. Affinity, as used herein, and $K_D$ are inversely related, that is that higher affinity is intended to refer to lower $K_D$, and lower affinity is intended to refer to higher $K_D$.

The term "ADC" refers to an antibody-drug conjugate, which in the context of the present invention refers to an anti-αvβ6 antibody, which is coupled to a drug moiety (e.g., MMAE or MMAF) as described in the present application.

The abbreviations "vc" and "val-cit" refer to the dipeptide valine-citrulline.

The abbreviation VKG refers to the tripeptide linker valine-lysine-glycine.

The abbreviation "PAB" refers to the self-immolative spacer:

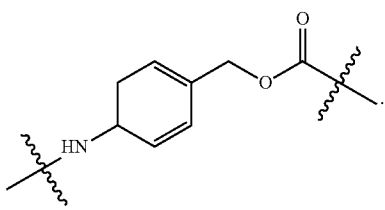 [SMILES: *NC1C=CC(COC(*)=O)=CC1]

The abbreviation "MC" refers to the stretcher maleimidocaproyl:

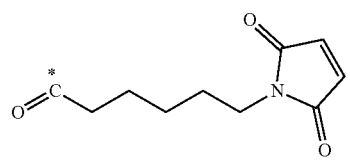 [SMILES: O=CCCCCCN1C(=O)C=CC1=O]

The abbreviation "MP" refers to the stretcher maleimidopropionyl:

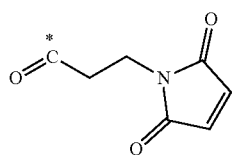 [SMILES: O=CCCN1C(=O)C=CC1=O]

"PEG Unit" as used herein is an organic moiety comprised of repeating ethylene-oxy subunits (PEGs or PEG subunits) and may be polydisperse, monodisperse or discrete (i.e., having discrete number of ethylene-oxy subunits). Polydisperse PEGs are a heterogeneous mixture of sizes and molecular weights whereas monodisperse PEGs are typically purified from heterogeneous mixtures and are therefore provide a single chain length and molecular weight. Preferred PEG Units comprises discrete PEGs, compounds that are synthesized in step-wise fashion and not via a polymerization process. Discrete PEGs provide a single molecule with defined and specified chain length.

The PEG Unit provided herein comprises one or multiple polyethylene glycol chains, each comprised of one or more ethyleneoxy subunits, covalently attached to each other. The polyethylene glycol chains can be linked together, for example, in a linear, branched or star shaped configuration. Typically, at least one of the polyethylene glycol chains prior to incorporation into a camptothecin conjugate is derivatized at one end with an alkyl moiety substituted with an electrophilic group for covalent attachment to the carbamate nitrogen of a methylene carbamate unit (i.e., represents an instance of R). Typically, the terminal ethyleneoxy subunit in each polyethylene glycol chains not involved in covalent attachment to the remainder of the Linker Unit is modified with a PEG Capping Unit, typically an optionally substituted alkyl such as —$CH_3$, $CH_2CH_3$ or $CH_2CH_2CO_2H$. A preferred PEG Unit has a single polyethylene glycol chain with 2 to 24 —$CH_2CH_2O$— subunits covalently attached in series and terminated at one end with a PEG Capping Unit.

A "cancer" refers to a broad group of various diseases characterized by the uncontrolled growth of abnormal cells in the body. A "cancer" or "cancer tissue" can include a tumor. Unregulated cell division and growth results in the formation of malignant tumors that invade neighboring tissues and can also metastasize to distant parts of the body through the lymphatic system or bloodstream. Following metastasis, the distal tumors can be said to be "derived from" the pre-metastasis tumor.

The term "antibody-dependent cellular cytotoxicity" ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fe effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fe effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component Clq which in turn activates the complement cascade leading to target cell death. Activation of complement may also result in deposition of complement components on the target cell surface that facilitate ADCC by binding complement receptors (e.g., CR3) on leukocytes.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

"Treatment" or "therapy" of a subject refers to any type of intervention or process performed on, or the administration of an active agent to, the subject with the objective of reversing, alleviating, ameliorating, inhibiting, slowing down, or preventing the onset, progression, development, severity, or recurrence of a symptom, complication, condition, or biochemical indicia associated with a disease. In some embodiments, the disease is cancer.

A "subject" includes any human or non-human animal. The term "non-human animal" includes, but is not limited to, vertebrates such as non-human primates, sheep, dogs, and rodents such as mice, rats, and guinea pigs. In some embodiments, the subject is a human. The terms "subject" and "patient" and "individual" are used interchangeably herein.

An "effective amount" or "therapeutically effective amount" or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example for the treatment of tumors, a therapeutically effective amount of an anti-cancer agent inhibits cell growth or tumor growth by at least about 10%, by at least about 20%, by at least about 30%, by at least about 40%, by at least about 50%, by at least about 60%, by at least about 70%, or by at least about 80%, by at least about 90%, by at least about 95%, by at least about 96%, by at least about 97%, by at least about 98%, or by at least about 99% in a treated subject(s) (e.g., one or more treated subjects) relative to an untreated subject(s) (e.g., one or more untreated subjects). In some embodiments, a therapeutically effective amount of an anti-cancer agent inhibits cell growth or tumor growth by 100% in a treated subject(s) (e.g., one or more treated subjects) relative to an untreated subject(s) (e.g., one or more untreated subjects).

In other embodiments of the disclosure, tumor regression can be observed and continue for a period of at least about 20 days, at least about 30 days, at least about 40 days, at least about 50 days, or at least about 60 days.

A therapeutically effective amount of a drug (e.g., anti-αvβ6 antibody-drug conjugate) includes a "prophylactically effective amount," which is any amount of the drug that, when administered alone or in combination with an anti-cancer agent to a subject at risk of developing a cancer (e.g., a subject having a pre-malignant condition) or of suffering a recurrence of cancer, inhibits the development or recurrence of the cancer. In some embodiments, the prophylactically effective amount prevents the development or recurrence of the cancer entirely. "Inhibiting" the development or recurrence of a cancer means either lessening the likelihood of the cancer's development or recurrence, or preventing the development or recurrence of the cancer entirely.

As used herein, "subtherapeutic dose" means a dose of a therapeutic compound (e.g., an anti-αvβ6 antibody-drug conjugate) that is lower than the usual or typical dose of the therapeutic compound when administered alone for the treatment of a hyperproliferative disease (e.g., cancer).

An "immune-related response pattern" refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

By way of example, an "anti-cancer agent" promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-cancer agent, results in a reduction in tumor growth or size, necrosis of the tumor, a decrease in severity of at least one disease symptom, an increase in frequency and duration of disease symptom-free periods, or a prevention of impairment or disability due to the disease affliction. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity or other adverse physiological effects at the cellular, organ and/or organism level (adverse effects) resulting from administration of the drug.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration that is at least the same as the treatment duration, or at least 1.5, 2.0, 2.5, or 3 times longer than the treatment duration.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progression free survival" or "PFS" refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" or "ORR" refers to the sum of complete response (CR) rate and partial response (PR) rate.

As used herein, "overall survival" or "OS" refers to the percentage of individuals in a group who are likely to be alive after a particular duration of time.

The phrase "pharmaceutically acceptable" indicates that the substance or composition must be compatible chemically and/or toxicologically, with the other ingredients comprising a formulation, and/or the mammal being treated therewith.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 4,4'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Administering" or "administration" refer to the physical introduction of a therapeutic agent to a subject, using any of the various methods and delivery systems known to those skilled in the art. Exemplary routes of administration for the anti-αvβ6 antibody-drug conjugate include intravenous, intramuscular, subcutaneous, intraperitoneal, spinal or other parenteral routes of administration, for example by injection or infusion (e.g., intravenous infusion). The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. A therapeutic agent can be administered via a non-parenteral route, or orally. Other non-parenteral routes of administration include a topical, epidermal or mucosal route of administration, for example, intranasally, vaginally, rectally, sublingually or topically. Administration can also be performed, for example, once, a plurality of times, and/or over one or more extended periods.

The terms "baseline" or "baseline value" used interchangeably herein can refer to a measurement or characterization of a symptom before the administration of the therapy (e.g., an anti-αvβ6 antibody-drug conjugate as described herein) or at the beginning of administration of the therapy. The baseline value can be compared to a reference value in order to determine the reduction or improvement of a symptom of a αvβ6-associated disease contemplated herein (e.g., cancer). The terms "reference" or "reference value" used interchangeably herein can refer to a measurement or characterization of a symptom after administration of the therapy (e.g., an anti-αvβ6 antibody-drug conjugate as described). The reference value can be measured one or more times during a dosage regimen or treatment cycle or at the completion of the dosage regimen or treatment cycle. A "reference value" can be an absolute value; a relative value; a value that has an upper and/or lower limit; a range of values; an average value; a median value: a mean value; or a value as compared to a baseline value.

Similarly, a "baseline value" can be an absolute value; a relative value; a value that has an upper and/or lower limit; a range of values; an average value; a median value; a mean value; or a value as compared to a reference value. The reference value and/or baseline value can be obtained from one individual, from two different individuals or from a group of individuals (e.g., a group of two, three, four, five or more individuals).

The term "monotherapy" as used herein means that the anti-αvβ6 antibody-drug conjugate is the only anti-cancer agent administered to the subject during the treatment cycle. Other therapeutic agents, however, can be administered to the subject. For example, anti-inflammatory agents or other agents administered to a subject with cancer to treat symptoms associated with cancer, but not the underlying cancer itself, including, for example inflammation, pain, weight loss, and general malaise, can be administered during the period of monotherapy.

An "adverse event" (AE) as used herein is any unfavorable and generally unintended or undesirable sign (including an abnormal laboratory finding), symptom, or disease associated with the use of a medical treatment. A medical treatment can have one or more associated AEs and each AE can have the same or different level of severity. Reference to methods capable of "altering adverse events" means a treatment regime that decreases the incidence and/or severity of one or more AEs associated with the use of a different treatment regime.

A "serious adverse event" or "SAE" as used herein is an adverse event that meets one of the following criteria:

Is fatal or life-threatening (as used in the definition of a serious adverse event, "life-threatening" refers to an event in which the patient was at risk of death at the time of the event; it does not refer to an event which hypothetically might have caused death if it was more severe.

Results in persistent or significant disability/incapacity

Constitutes a congenital anomaly/birth defect

Is medically significant, i.e., defined as an event that jeopardizes the patient or may require medical or surgical intervention to prevent one of the outcomes listed above. Medical and scientific judgment must be exercised in deciding whether an AE is "medically significant"

Requires inpatient hospitalization or prolongation of existing hospitalization, excluding the following: 1) routine treatment or monitoring of the underlying disease, not associated with any deterioration in condition; 2) elective or pre-planned treatment for a pre-existing condition that is unrelated to the indication under study and has not worsened since signing the informed consent; and 3) social reasons and respite care in the absence of any deterioration in the patient's general condition.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 20%. Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

Reference to "about" a value or parameter herein includes (and describes) embodiments that are directed to that value or parameter per se. For example, description referring to "about X" encompasses and describes "X."

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

II. General

The invention provides antibodies that specifically bind αvβ6. The present invention is based, in part, on the discovery that antibody-drug conjugates, including vcM-MAE antibody-drug conjugates, targeted to αvβ6 are particularly effective at killing αvβ6+ expressing cells. αvβ6 has been shown to be expressed in a variety of cancers, including non-small cell lung cancer (NSCLC) (squamous and adeno), head and neck cancer (including head and neck squamous carcinoma), esophageal cancer, breast cancer (including breast invasive carcinoma), ovarian cancer, bladder cancer (including urothelial carcinoma), skin cancer (squamous cell carcinoma, or SCC), renal cancer (including renal clear cell, renal papillary cell, and kidney chromophobe), cervical cancer, gastric cancer, prostate cancer (including prostate adenocarcinoma), endometrial cancer (including uterine carcinosarcoma and uterine corpus endometrial), rectum adenocarcinoma, thyroid carcinoma, colon adenocarcinoma, stomach adenocarcinoma, and pancreatic cancer (including pancreatic adenocarcinoma).

III. Target Molecules

Unless otherwise indicated, αvβ6 refers to human αvβ6. An exemplary β6 human sequence is assigned GenBank accession number AAA36122. An exemplary αv human sequence is assigned NCBI NP_002201.1.

IV. Antibodies of the Invention

The invention provides the murine 2A2 antibody, and chimeric, humanized, and human 2A2 antibodies.

The affinity of antibodies of the present invention (e.g., chimeric, humanized and human forms of the mouse 2A2 antibody) for human αvβ6 is preferably equivalent to the affinity of mouse 2A2 antibody for human αvβ6, greater than the affinity of mouse 2A2 antibody for human αvβ6 or within a factor of ten, within a factor of five, or within a factor of two weaker than that of the murine antibody 2A2 for human αvβ6. One method of measuring affinity of an antibody for its target antigen is by determining an antibody's apparent dissociation constant. The present invention encompasses antibodies (e.g., chimeric, humanized and human forms of the mouse 2A2 antibody) having an apparent dissociation constant that is essentially the same as that of murine 2A2 (i.e., within experimental error) as well as antibodies having an dissociation constant lower or higher than that of murine antibody 2A2 for human αvβ6. Chimeric, humanized and human 2A2 antibodies specifically bind to human αvβ6 in native form and/or recombinantly expressed from CHO cells as does the mouse 2A2 antibody. Typically, chimeric, humanized and human 2A2 anti-αvβ6 antibodies compete with murine 2A2 for binding to human αvβ6.

Preferred antibodies of the invention inhibit cancer (e.g., growth of cells, metastasis and/or lethality to the organisms) as shown on cancerous cells propagating in culture, in an animal model or clinical trial. Animal models can be formed by implanting αvβ6-expressing human tumor cell lines into appropriate immunodeficient rodent strains, e.g., athymic nude mice or SCID mice. These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-αvβ6 antibodies or conjugated forms thereof as described in the Examples.

Generally, anti-αvβ6 antibodies and/or anti-αvβ6 antibody-drug conjugates of the disclosure bind αvβ6, e.g., human αvβ6, and exert cytostatic and cytotoxic effects on malignant cells, such as cancer cells. Anti-αvβ6 antibodies of the disclosure are preferably monoclonal, and may be multispecific, human, humanized or chimeric antibodies, single chain antibodies, Fab fragments, F(ab') fragments, fragments produced by a Fab expression library, and αvβ6 binding fragments of any of the above. In some embodiments, the anti-αvβ6 antibodies of the disclosure specifically bind αvβ6. The immunoglobulin molecules of the disclosure can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments of the disclosure, the anti-αvβ6 antibodies are antigen-binding fragments (e.g., human antigen-binding fragments) as described herein and include, but are not limited to, Fab, Fab' and F(ab')2, Fd, single-chain Fvs (scFv), single-chain antibodies, disulfide-linked Fvs (sdFv) and fragments comprising either a $V_L$ or $V_H$ domain. Antigen-binding fragments, including single-chain antibodies, may comprise the variable region(s) alone or in combination with the entirety or a portion of the following: hinge region, CH1, CH2, CH3 and CL domains. Also included in the present disclosure are antigen-binding fragments comprising any combination of variable region(s) with a hinge region, CH1, CH2, CH3 and CL domains. In some embodiments, the anti-αvβ6 antibodies or antigen-binding fragments thereof are human, murine (e.g., mouse and rat), donkey, sheep, rabbit, goat, guinea pig, camelid, horse, or chicken.

The anti-αvβ6 antibodies of the present disclosure may be monospecific, bispecific, trispecific or of greater multi specificity. Multispecific antibodies may be specific for different epitopes of αvβ6 or may be specific for both αvβ6 as well as for a heterologous protein.

Anti-αvβ6 antibodies of the present disclosure may be described or specified in terms of the particular CDRs they comprise. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme); Al-Lazikani et al., (1997) JMB 273, 927-948 ("Chothia" numbering scheme); MacCallum et al., J. Mol.

Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme); and Martin et al., "Modeling antibody hypervariable loops: a combined algorithm," PNAS, 1989, 86(23): 9268-9272, ("AbM" numbering scheme). The boundaries of a given CDR may vary depending on the scheme used for identification. In some embodiments, a "CDR" or "complementarity determining region," or individual specified CDRs (e.g., CDR-H1, CDR-H2, CDR-H3), of a given antibody or region thereof (e.g., variable region thereof) should be understood to encompass a (or the specific) CDR as defined by any of the aforementioned schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes. The scheme for identification of a particular CDR or CDRs may be specified, such as the CDR as defined by the Kabat, Chothia, AbM or IMGT method.

In an embodiment, the CDR sequences of the anti-αvβ6 antibodies and of the anti-αvβ6 antibody-drug conjugates described herein are according to the Kabat numbering scheme. In another embodiment, the CDR sequences of the anti-αvβ6 antibodies and of the anti-αvβ6 antibody-drug conjugates described herein are according to the IMGT numbering scheme.

In one aspect, provided herein is an anti-αvβ6 antibody comprising a heavy chain variable region and a light chain variable region, wherein the heavy chain variable region comprises (i) CDR-H1 comprising the amino acid sequence of SEQ ID NO:31, (ii) CDR-H2 comprising the amino acid sequence of SEQ ID NO:32, and (iii) CDR-H3 comprising the amino acid sequence of SEQ ID NO:33; and/or wherein the light chain variable region comprises (i) CDR-L1 comprising the amino acid sequence of SEQ ID NO:37, (ii) CDR-L2 comprising the amino acid sequence of SEQ ID NO:42, and (iii) CDR-L3 comprising the amino acid sequence of SEQ ID NO:39, wherein the CDRs of the anti-αvβ6 antibody are defined by the Kabat numbering scheme. In other embodiments, CDR-L1 comprises the amino acid sequence of SEQ ID NO: 40. In other embodiments, CDR-L2 comprises the amino acid sequence of SEQ ID NO: 38 or 41.

In one aspect, provided herein is an anti-αvβ6 antibody comprising a heavy chain variable region and a light chain variable region, wherein the heavy chain variable region comprises (i) CDR-H1 comprising the amino acid sequence of SEQ ID NO:34, (ii) CDR-H2 comprising the amino acid sequence of SEQ ID NO:35, and (iii) CDR-H3 comprising the amino acid sequence of SEQ ID NO:36; and/or wherein the light chain variable region comprises (i) CDR-L1 comprising the amino acid sequence of SEQ ID NO:43, (ii) CDR-L2 comprising the amino acid sequence of SEQ ID NO:44, and (iii) CDR-L3 comprising the amino acid sequence of SEQ ID NO:45, wherein the CDRs of the anti-αvβ6 antibody are defined by the IMGT numbering scheme.

An anti-αvβ6 antibody described herein may comprise any suitable framework variable domain sequence, provided that the antibody retains the ability to bind αvβ6 (e.g., human αvβ6). In some embodiments of the anti-αvβ6 antibodies described herein, the heavy and the light chain variable domains comprise the amino acid sequences of SEQ ID NO: 6 and SEQ ID NO: 17, respectively. In some embodiments of the anti-αvβ6 antibodies described herein, the heavy and light chains comprise the amino acid sequences of SEQ ID NO: 21 and SEQ ID NO: 29, respectively.

In some embodiments, provided herein is an anti-αvβ6 antibody and/or anti-αvβ6 antibody-drug conjugate comprising a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:6. In certain embodiments, a heavy chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:6 contains substitutions (e.g., conservative substitutions), insertions, or deletions relative to the reference sequence and retains the ability to bind to an αvβ6 (e.g., human αvβ6). In certain embodiments, a total of 1 to 10 amino acids have been substituted, inserted and/or deleted in SEQ ID NO:6. In other embodiments, a total of 3 to 10 amino acids have been substituted, inserted and/or deleted in SEQ ID NO:6. In certain embodiments, substitutions, insertions, or deletions (e.g., 1, 2, 3, 4, or 5 amino acids) occur in regions inside the CDRs. In certain embodiments, substitutions, insertions, or deletions (e.g., 1, 2, 3, 4, or 5 amino acids) occur in regions outside the CDRs (i.e., in the FRs). In some embodiments, the anti-αvβ6 antibody comprises a heavy chain variable domain sequence of SEQ ID NO:6 including post-translational modifications of that sequence.

In some embodiments, provided herein is an anti-αvβ6 antibody and/or anti-αvβ6 antibody-drug conjugate comprising a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:17. In certain embodiments, a light chain variable domain comprising an amino acid sequence having at least 85%, 86%, 87%, 88%, 89%, 90%, 91%, 92%, 93%, 94%, 95%, 96%, 97%, 98%, or 99% sequence identity to the amino acid sequence of SEQ ID NO:17 contains substitutions (e.g., conservative substitutions), insertions, or deletions relative to the reference sequence and retains the ability to bind to an αvβ6 (e.g., human αvβ6). In certain embodiments, a total of 1 to 10 amino acids have been substituted, inserted and/or deleted in SEQ ID NO:17. In other embodiments, a total of 1 to 2 amino acids have been substituted, inserted and/or deleted in SEQ ID NO:17. In certain embodiments, substitutions, insertions, or deletions (e.g., 1, 2, 3, 4, or 5 amino acids) occur in regions outside the CDRs (i.e., in the FRs). In some embodiments, the anti-αvβ6 antibody comprises a light chain variable domain sequence of SEQ ID NO:17 including post-translational modifications of that sequence.

There are five classes of immunoglobulins: IgA, IgD, IgE, IgG and IgM, having heavy chains designated α, δ, ε, γ and μ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. *mAbs* Vol 1 Issue 4 1-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1.

The antibodies of the invention also include derivatives that are modified, i.e., by the covalent attachment of any type of molecule to the antibody such that covalent attachment does not prevent the antibody from binding to αvβ6 or from exerting a cytostatic or cytotoxic effect on HD cells. For example, but not by way of limitation, the antibody derivatives include antibodies that have been modified, e.g., by glycosylation, acetylation, PEGylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Humanized Antibodies

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. A preferred acceptor sequence for the heavy chain is the germline $V_H$ exon IGHV1-46 and for the J exon ($J_H$), exon IGHJ4. For the light chain, a preferred acceptor sequence is exon IGKV1D-33 and for the J exon IGKJ2. Alternative preferred acceptor sequences for the heavy chain include the J exons ($J_H$), IGHJ1, IGHJ2, IGHJ3, IGHJ5 or IGHJ6. Alternative preferred acceptor sequences for the light chain include J exons IGKJ1, IGKJ3, IGKJ4 or IGKJ5. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 60%, 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5) CDRs from a mouse antibody (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly, (2) is adjacent to a CDR region, (3) otherwise interacts with a CDR region (e.g. is within about 6 A of a CDR region); or (4) mediates interaction between the heavy and light chains.

Although the 2A2 antibody was identified as a mouse antibody, the present application also encompasses human 2A2 antibodies. By the term, "human 2A2 antibody" is meant an antibody that is derived from human immunoglobulin gene sequences and that has CDRs that are substantially identical to those of murine 2A2 antibody and displays similar properties, i.e., binding specificity to αvβ6. In some aspects, a human 2A2 antibody comprises a heavy chain variable region that is substantially identical to a heavy chain variable region described herein and/or a light chain variable region that is substantially identical to a light chain variable region described herein. In some embodiments, a 2A2 antibody of the present invention is not a human antibody, e.g., a 2A2 antibody of the present invention is a murine, chimeric, or humanized antibody.

One aspect of the invention provides humanized forms of the mouse antibody 2A2. One such humanized variant of the mouse antibody 2A2 is designated HCLG. HCLG comprises a mature heavy chain variable region comprising the amino acid sequence of SEQ ID NO:6 and a mature light chain variable region comprising the amino acid sequence of SEQ ID NO:17. Humanized antibodies of the invention include variants of the HCLG humanized antibody in which the humanized heavy chain mature variable region shows at least 90%, 95% or 99% identity to SEQ ID NO: 6 and the humanized light chain mature variable region shows at least 90%, 95% or 99% sequence identity to SEQ ID NO:17. Preferably, in such antibodies some or all of the backmutations in HCLG are retained. In other words, at least 1, 2, 3, 4, 5, 6, 7, 8, or preferably all 9 of heavy chain positions H2, H28, H48, H67, H69, H71, H73, H78, and H93 are occupied by F, S, I, A, L, V, K, A, and T, respectively. Likewise, position L69 is preferably occupied by R, and L71 is preferably occupied by Y. The CDR regions can be defined by any conventional definition (e.g., Chothia) but are preferably as defined by Kabat or IMGT. In one embodiment, the humanized antibody comprises a heavy chain comprising the 3 CDRs of SEQ ID NO: 6 and variable region frameworks with at least 95% identity to the variable region frameworks of SEQ ID NO: 6. In another embodiment, the humanized antibody comprises a light chain comprising the 3 CDRs of SEQ ID NO: 17 and variable region frameworks with at least 95% identity to variable region frameworks of SEQ ID NO: 17. In a further embodiment, the humanized antibody comprises a heavy chain comprising the 3 CDRs of SEQ ID NO: 6 and variable region frameworks with at least 98% identity to the variable region frameworks of SEQ ID NO: 6, and a light chain comprising the 3 CDRs of SEQ ID NO: 17, and variable region frameworks with at least 98% identity to the variable region frameworks of SEQ ID NO: 17. In one embodiment, the humanized antibody comprises a heavy chain comprising the 3 CDRs of SEQ ID NO: 6 and variable region frameworks with at least 99% identity to the variable region frameworks of SEQ ID NO: 6. In another embodiment, the humanized antibody comprises a light chain comprising the 3 CDRs of SEQ ID NO: 17 and variable region frameworks with at least 99% identity to variable region frameworks of SEQ ID NO: 17.

One possible variation is to substitute certain residues in the CDRs of the mouse antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, J. Mol. Biol. 196:901, 1987), by molecular modeling and/or empirically, or as described in Gonzales et al., Mol. Immunol. 41: 863 (2004). In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

Although not preferred other amino acid substitutions can be made, for example, in framework residues not in contact with the CDRs, or even some potential CDR-contact residues amino acids within the CDRs. Often the replacements made in the variant humanized sequences are conservative with respect to the replaced HCLG amino acids. Preferably, replacements relative to HCLG (whether or not conservative) have no substantial effect on the binding affinity or potency of the humanized mAb, that is, its ability to bind human αvβ6 and inhibit growth of cancer cells.

Selection of Constant Region

The heavy and light chain variable regions of humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotopes IgG1 and IgG3 have strong complement-dependent cytotoxicity, human isotype IgG2 weak complement-dependent cytotoxicity and human. IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

Exemplary substitution include the amino acid substitution of the native amino acid to a cysteine residue is introduced at amino acid position 234, 235, 237, 239, 267, 298, 299, 326, 330, or 332, preferably an S239C mutation in a human IgG1 isotype (US 20100158909). The presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγRI receptor (see, e.g., U.S. Pat. Nos. 6,624,821, 5,624,821.)

The in vivo half-life of an antibody can also impact on its effector functions. The half-life of an antibody can be increased or decreased to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, Annu. Rev. Immunol. 18:739-766; Ghetie and Ward, 2002, Immunol. Res. 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, Ann. Rev. Immunol. 18:739-766; Ghetie and Ward, 2002, Immunol. Res. 25:97-113). The region on human IgG1 involved in FcRn binding has been mapped (Shields et al, 2001, J. Biol. Chem. 276:6591-604). Alanine substitutions at positions Pro238, Thr256, Thr307, Gln311, Asp312, Glu380, Glu382, or Asn434 of human IgG1 enhance FcRn binding (Shields et al, 2001, J. Biol. Chem. 276:6591-604). IgG1 molecules harboring these substitutions have longer serum half-lives. Consequently, these modified IgG1 molecules may be able to carry out their effector functions, and hence exert their therapeutic efficacies, over a longer period of time compared to unmodified IgG1. Other exemplary substitutions for increasing binding to FcRn include a Gln at position 250 and/or a Leu at position 428. EU numbering is used for all position in the constant region.

Oligosaccharides covalently attached to the conserved Asn297 are involved in the ability of the Fc region of an IgG to bind FcγR (Lund et al, 1996, J. Immunol. 157:4963-69; Wright and Morrison, 1999, Trends Biotechnol. 15:26-31). Engineering of this glycoform on IgG can significantly improve IgG-mediated ADCC. Addition of bisecting N-acetylglucosamine modifications (Umana et al, 1999, Nat. Biotechnol. 17:176-180; Davies et al, 2001, Biotech. Bioeng. 74:288-94) to this glycoform or removal of fucose (Shields et al, 2002, J. Biol. Chem. 277:26733-40; Shinkawa et al, 2003, J. Biol. Chem. 278:6591-604; Niwa et al., 2004, Cancer Res. 64:2127-33) from this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al, 2001, J. Biol. Chem. 276:6591-604). When compared to parental IgG1, a subset of these variants involving substitutions at Thr256/Ser298, Ser298/Glu333, Ser298/Lys334, or Ser298/Glu333 Lys334 to Ala demonstrate increased in both binding affinity toward FcγR and ADCC activity (Shields et al, 2001, J. Biol. Chem. 276:6591-604; Okazaki et al, 2004, J. Mol. Biol. 336:1239-49).

Complement fixation activity of antibodies (both C1q binding and CDC activity) can be improved by substitutions at Lys326 and Glu333 (Idusogie et al., 2001, J. Immunol. 166:2571-2575). The same substitutions on a human IgG2 backbone can convert an antibody isotype that binds poorly to C1q and is severely deficient in complement activation activity to one that can both bind C1q and mediate CDC (Idusogie et al, 2001, J. Immunol. 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al, 1995, J. Immunol. 154:2226-36). Also, substituting Ser444 located close to the carboxy-terminal of IgG 1 heavy chain with Cys induced tail-to-tail dimerization of IgG 1 with a 200-fold increase of CDC activity over monomeric IgG1 (Shopes et al, 1992, J. Immunol. 148:2918-22). In addition, a bispecific diabody construct with specificity for C1q also confers CDC activity (Kontermann et al., 1997, Nat. Biotech. 15:629-31).

Complement activity can be reduced by mutating at least one of the amino acid residues 318, 320, and 322 of the heavy chain to a residue having a different side chain, such as Ala. Other alkyl-substituted non-ionic residues, such as Gly, He, Leu, or Val, or such aromatic non-polar residues as Phe, Tyr, Trp and Pro in place of any one of the three residues also reduce or abolish C1q binding. Ser, Thr, Cys, and Met can be used at residues 320 and 322, but not 318, to reduce or abolish C1q binding activity.

Replacement of the 318 (Glu) residue by a polar residue may modify but not abolish C1q binding activity. Replacing residue 297 (Asn) with Ala results in removal of lytic activity but only slightly reduces (about three fold weaker) affinity for C1q. This alteration destroys the glycosylation site and the presence of carbohydrate that is required for complement activation. Any other substitution at this site also destroys the glycosylation site. The following mutations and any combination thereof also reduce C1q binding: D270A, K322A, P329A, and P31 IS (see WO 06/036291). The L234A/L235A mutation (or LALA mutation) also reduces C1q binding, as well as FcγR binding.

Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fcgamma receptor binding or increase binding to FcRN.

V. Expression of Recombinant Antibodies

Humanized antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Once expressed, antibodies can be purified according to standard procedures of the art, including HPLC purification, column chromatography, gel electrophoresis and the like (see generally, Scopes, Protein Purification (Springer-Verlag, NY, 1982)).

VI. Nucleic Acids

The invention further provides nucleic acids encoding any of the humanized heavy and light chains described above. Typically, the nucleic acids also encode a signal peptide fused to the mature heavy and light chains. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

In some aspects, also provided herein are nucleic acids encoding an anti-αvβ6 antibody or antigen-binding fragment thereof as described herein. Further provided herein are vectors comprising the nucleic acids encoding an anti-αvβ6 antibody or antigen-binding fragment thereof as described herein. Further provided herein are host cells expressing the nucleic acids encoding an anti-αvβ6 antibody or antigen-binding fragment thereof as described herein. Further provided herein are host cells comprising the vectors comprising the nucleic acids encoding an anti-αvβ6 antibody or antigen-binding fragment thereof as described herein.

The anti-αvβ6 antibodies described herein may be prepared by well-known recombinant techniques using well known expression vector systems and host cells. In one embodiment, the antibodies are prepared in a CHO cell using the GS expression vector system as disclosed in De la Cruz Edmunds et al., 2006, *Molecular Biotechnology* 34; 179-190, EP216846, U.S. Pat. No. 5,981,216, WO 87/04462, EP323997, U.S. Pat. Nos. 5,591,639, 5,658,759, EP338841, U.S. Pat. Nos. 5,879,936, and 5,891,693.

Monoclonal anti-αvβ6 antibodies described herein may e.g. be produced by the hybridoma method first described by Kohler et al., *Nature,* 256, 495 (1975), or may be produced by recombinant DNA methods. Monoclonal antibodies may also be isolated from phage antibody libraries using the techniques described in, for example, Clackson et al., *Nature,* 352, 624-628 (1991) and Marks et al., *J Mol, Biol.,* 222(3):581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

VII. Antibody-Drug Conjugates

Anti-αvβ6 antibodies can be conjugated to cytotoxic or cytostatic moieties (including pharmaceutically compatible salts thereof) to form an antibody drug conjugate (ADC). Particularly suitable moieties for conjugation to antibodies are cytotoxic agents (e.g., chemotherapeutic agents), prodrug converting enzymes, radioactive isotopes or compounds, or toxins (these moieties being collectively referred to as a therapeutic agent). For example, an anti-αvβ6 antibody can be conjugated to a cytotoxic agent such as a chemotherapeutic agent, or a toxin (e.g., a cytostatic or cytocidal agent such as, e.g., abrin, ricin A, pseudomonas exotoxin, or diphtheria toxin).

An anti-αvβ6 antibody can be conjugated to a pro-drug converting enzyme. The pro-drug converting enzyme can be recombinantly fused to the antibody or chemically conjugated thereto using known methods. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Arnon et al, "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al, "Antibodies For Drug Delivery," in Controlled Drug Delivery (Robinson et al. eds., Marcel Dekker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al, 1982, Immunol. Rev. 62:119-58. See also, e.g., PCT publication WO 89/12624.)

The therapeutic agent can be conjugated in a manner that reduces its activity unless it is cleaved off the antibody (e.g., by hydrolysis, by antibody degradation or by a cleaving agent). Such therapeutic agent is attached to the antibody with a cleavable linker that is sensitive to cleavage in the intracellular environment of the αvβ6-expressing cancer cell but is not substantially sensitive to the extracellular environment, such that the conjugate is cleaved from the antibody when it is internalized by the αvβ6-expressing cancer cell (e.g., in the endosomal or, for example by virtue of pH sensitivity or protease sensitivity, in the lysosomal environment or in the caveolear environment).

Typically the ADC comprises a linker region between the therapeutic agent and the anti-αvβ6 antibody. As noted supra, typically, the linker is cleavable under intracellular conditions, such that cleavage of the linker releases the therapeutic agent from the antibody in the intracellular environment (e.g., within a lysosome or endosome or caveolea). The linker can be, e.g., a peptidyl linker that is cleaved by an intracellular peptidase or protease enzyme, including a lysosomal or endosomal protease. Typically, the peptidyl linker is at least two amino acids long or at least three amino acids long. Cleaving agents can include cathepsins B and D and plasmin (see, e.g., Dubowchik and Walker, 1999, Pharm. Therapeutics 83:67-123). Most typical are peptidyl linkers that are cleavable by enzymes that are present in αvβ6-expressing cells. For example, a peptidyl linker that is cleavable by the thiol-dependent protease cathepsin-B, which is highly expressed in cancerous tissue, can be used (e.g., a linker comprising a Phe-Leu or a Gly-Phe-Leu-Gly peptide). Other such linkers are described, e.g., in U.S. Pat. No. 6,214,345. In specific embodiments, the peptidyl linker cleavable by an intracellular protease comprises a Val-Cit linker or a Phe-Lys dipeptide (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

The cleavable linker can be pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al, 1989, Biol. Chem. 264: 14653-

14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929)).

Other linkers are cleavable under reducing conditions (e.g., a disulfide linker). Disulfide linkers include those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT. (See, e.g., Thorpe et al, 1987, Cancer Res. 47:5924-5931; Wawrzynczak et al, In Immunoconjugates: Antibody Conjugates in Radioimagery and Therapy of Cancer (C. W. Vogel ed., Oxford U. Press, 1987. See also U.S. Pat. No. 4,880,935.)

The linker can also be a malonate linker (Johnson et al, 1995, Anticancer Res. 15:1387-93), a maleimidobenzoyl linker (Lau et al, 1995, Bioorg-Med-Chem. 3(10):1299-1304), or a 3'-N-amide analog (Lau et al, 1995, Bioorg-Med-Chem. 3(10):1305-12). The linker can also be a malonate linker (Johnson et al, 1995, Anticancer Res. 15:1387-93), a maleimidobenzoyl linker (Lau et al, 1995, Bioorg-Med-Chem. 3(10):1299-1304), or a 3'-N-amide analog (Lau et al, 1995, Bioorg-Med-Chem. 3(10):1305-12).

The linker also can be a non-cleavable linker, such as an maleimido-alkylene- or maleimide-aryl linker that is directly attached to the therapeutic agent (e.g., a drug). An active drug-linker is released by degradation of the antibody.

The linker can promote cellular internalization. The linker can promote cellular internalization when conjugated to the therapeutic agent (i.e., in the milieu of the linker-therapeutic agent moiety of the ADC or ADC derivative as described herein). Alternatively, the linker can promote cellular internalization when conjugated to both the therapeutic agent and the anti-αvβ6 antibody (i.e., in the milieu of the ADC as described herein).

The anti-αvβ6 antibody can be conjugated to the linker via a heteroatom of the antibody. These heteroatoms can be present on the antibody in its natural state or can be introduced into the antibody. In some aspects, the anti-αvβ6 antibody will be conjugated to the linker via a nitrogen atom of a lysine residue. In other aspects, the anti-αvβ6 antibody will be conjugated to the linker via a sulfur atom of a cysteine residue. The cysteine residue can be naturally-occurring or one that is engineered into the antibody. Methods of conjugating linkers and drug-linkers to antibodies via lysine and cysteine residues are known in the art.

Exemplary antibody-drug conjugates include auristatin based antibody-drug conjugates (i.e., the drug component is an auristatin drug). Auristatins bind tubulin, have been shown to interfere with microtubule dynamics and nuclear and cellular division, and have anticancer activity. Typically the auristatin based antibody-drug conjugate comprises a linker between the auristatin drug and the anti-αvβ6 antibody. The linker can be, for example, a cleavable linker (e.g., a peptidyl linker, a carbohydrate linker) or a non-cleavable linker (e.g., linker released by degradation of the antibody). Auristatins include (but are not limited to) auristatin T, MMAF, and MMAE. The synthesis and structure of exemplary auristatins are described in U.S. Pat. Nos. 7,659,241, 7,498,298, 2009-0111756, 2009-0018086, and U.S. Pat. No. 7,968,687 each of which is incorporated herein by reference in its entirety and for all purposes.

Exemplary auristatin based antibody drug conjugates include vcMMAE (or 1006), vcMMAF and mcMMAF antibody drug conjugates as shown below wherein p represents the drug load, Ab is an anti-αvβ6 antibody as described herein and val-cit or "vc" represents the valine-citrulline dipeptide:

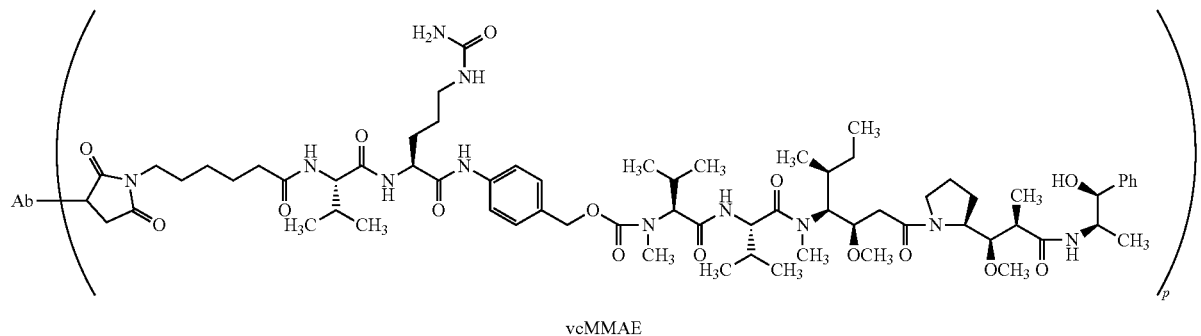

vcMMAE

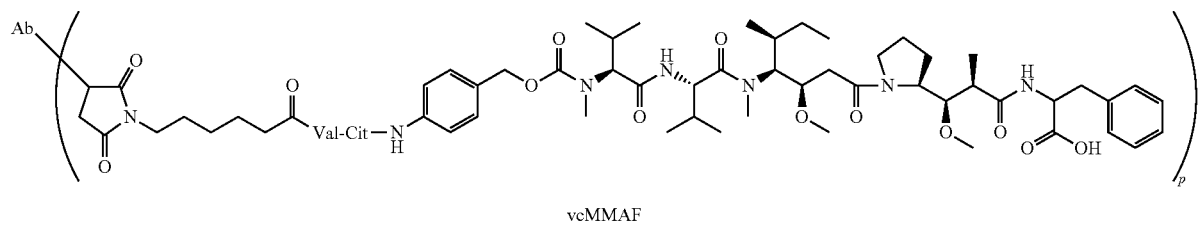

vcMMAF

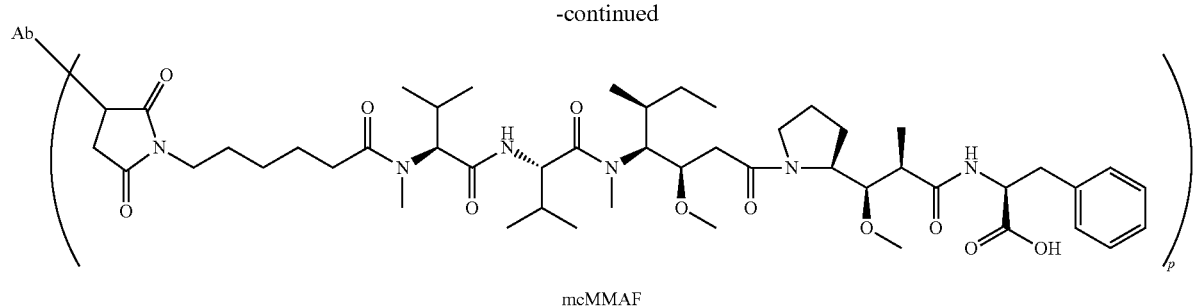

mcMMAF or a pharmaceutically acceptable salt thereof. The drug loading is represented by p, the number of drug-linker molecules per antibody. Referring to the αvβ6 targeted antibody-drug conjugates, the subscript p represents the drug load and, depending on the context, can represent the number of molecules of drug-linker molecules attached to an individual antibody molecule and as such, is an integer value, or can represent an average drug load and, as such, can be an integer or non-integer value but is typically a non-integer value. An average drug load represents the average number of drug-linker molecules per antibody in a population. Often, but not always, when we refer to an antibody, e.g., a monoclonal antibody, we are referring to a population of antibody molecules. In a composition comprising a population of antibody-drug conjugate molecules, the average drug load is an important quality attribute as it determines the amount of drug that can be delivered to a target cell. The percentage of unconjugated antibody molecules in the composition is included in the average drug load value.

In preferred aspects of the present invention, the average drug load when referring to a composition comprising a population of antibody-drug conjugate compounds is from 1 to about 16, preferably about 2 to about 14, more preferably about 2 to about 10. In an embodiment, the DAR is from about 2 to about 5. In a further embodiment, the DAR is 4. In another embodiment, the DAR is from about 6 to about 10. In a further embodiment, the DAR is 8. The average number of drugs per antibody in a preparation may be characterized by conventional means such as mass spectroscopy, HIC, ELISA assay, and HPLC. In some aspects, the anti-αvβ6 antibody is attached to the drug-linker through a cysteine residue of the antibody. In some aspects, the cysteine residue is one that is engineered into the antibody. In other aspects, the cysteine residue is an interchain disulfide cysteine residue.

In some embodiments, incorporation of a polyethylene glycol polymer as a side chain into a cleavable β-glucuronide MMAE drug-linker provides antibody drug-conjugates with decreased plasma clearance and increased antitumor activity in xenograft models as compared to a non-PEGylated control. Accordingly, particularly advantageous drug-linkers for attachment to the antibodies of the present invention are as follows in formula V:

(V)

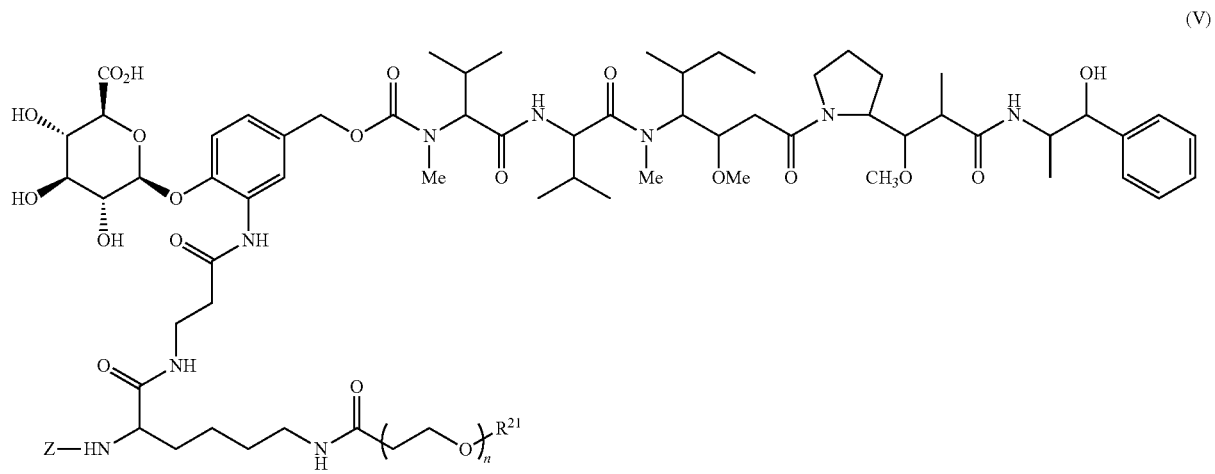

or a pharmaceutically acceptable salt thereof.

A preferred stereochemistry for such drug-linker is shown below in formula Va:

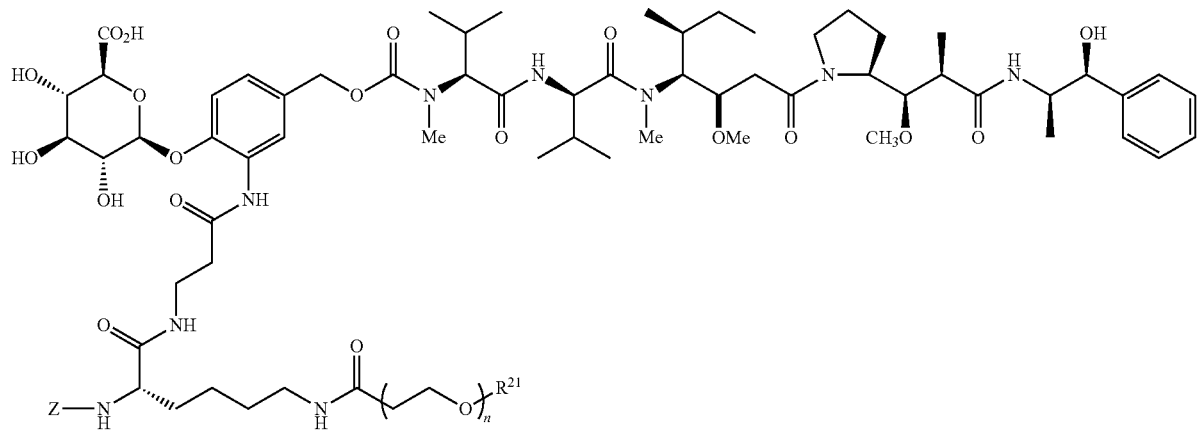

(Va)

or a pharmaceutically acceptable salt thereof wherein for formulas V and Va, Z represents an organic moiety having a reactive site capable of reacting with a functional group on the antibody to form a covalent attachment thereto, n ranges from 8 to 36 and most preferably ranges from 8 to 14 (most preferably 12), $R^{21}$ is a capping unit for the polyethylene glycol moiety; preferably —$CH_3$ or —$CH_2CH_2CO_2H$.

A preferred Z moiety is a maleimido-containing moiety. Particularly preferred Z moieties are shown in the drug-linkers below:

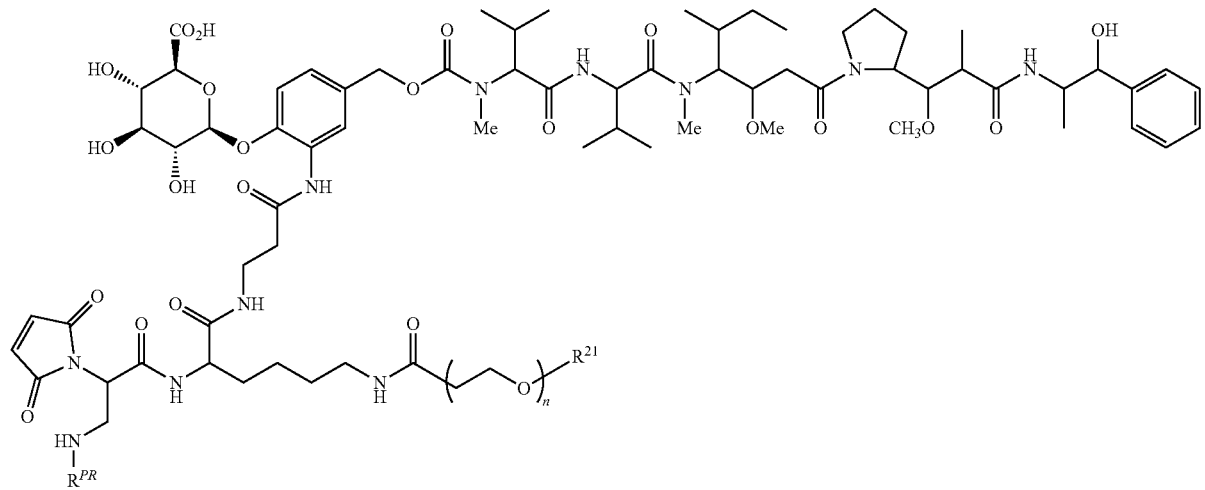

(VI)

(VII)

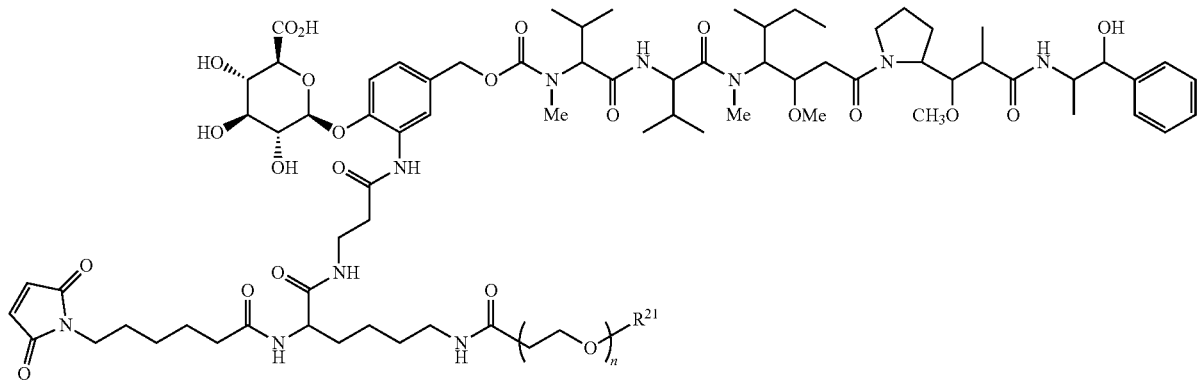

or a pharmaceutically acceptable salt thereof.

A preferred stereochemistry for such drug-linkers is shown below:

(VIa)

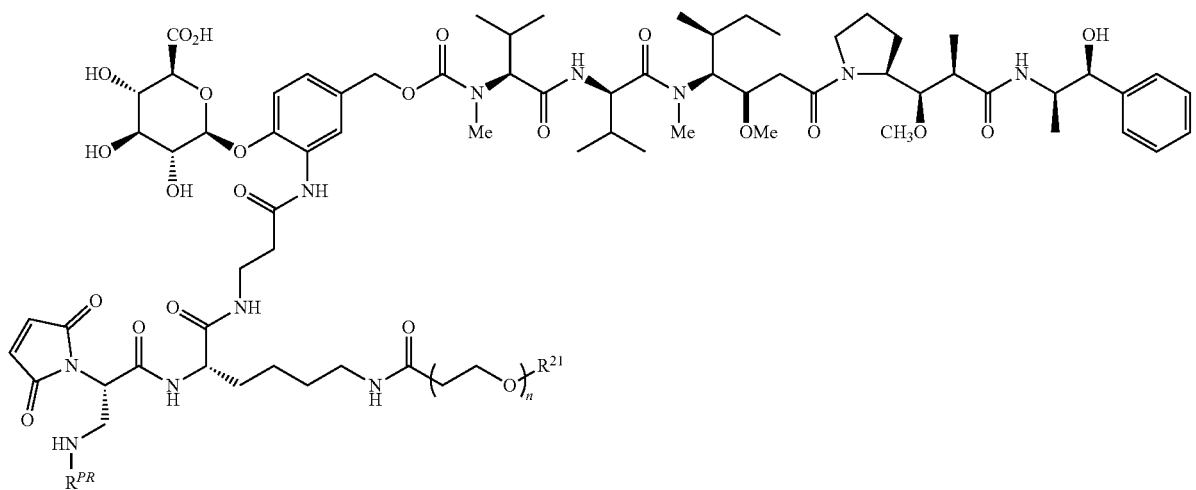

(VIIa)

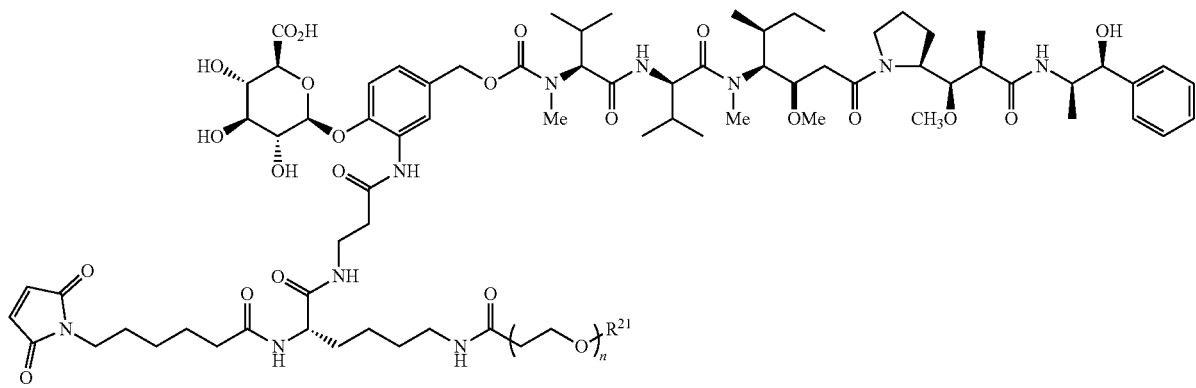

or a pharmaceutically acceptable salt thereof wherein for formulas VI, VIa, VII and VIIa, n ranges from 8 to 36 and most preferably ranges from 8 to 14 (most preferably 12), $R^{PR}$ is hydrogen or a protecting group, e.g., acid labile protecting group, e.g., BOC. $R^{21}$ is a capping unit for the polyethylene glycol moiety, preferably —$CH_3$ or —$CH_2CH_2CO_2H$.

As noted above, $R^{PR}$ can be hydrogen or a protecting group. Protective groups as used herein refer to groups which selectively block, either temporarily or permanently, a reactive site in a multifunctional compound. A protecting group is a suitable protecting group when it is capable of preventing or avoiding unwanted side-reactions or premature loss of the protecting group under reaction conditions required to effect desired chemical transformation elsewhere in the molecule and during purification of the newly formed molecule when desired, and can be removed under conditions that do not adversely affect the structure or stereochemical integrity of that newly formed molecule. Suitable amine protecting groups include acid-labile nitrogen protecting groups, including those provided by Isidro-Llobel et al. "Amino acid-protecting groups" Chem. Rev. (2009) 109: 2455-2504. Typically, an acid-labile nitrogen-protecting group transforms a primary or secondary amino group to its corresponding carbamate and includes t-butyl, allyl, and benzyl carbamates.

As noted above, $R^{21}$ is a capping unit for the polyethylene glycol moiety. As will be appreciated by the skilled artisan, polyethylene glycol units can be terminally capped with a wide diversity of organic moieties, typically those that are relatively non-reactive. Alkyl and substituted alkyl groups are preferred.

For the MMAE PEGylated ADCs, such as those exemplified herein, a particularly preferred average drug load is about 8. In exemplary embodiments, the drug-linkers are conjugated to the cysteine residues of the reduced interchain disulfides. In some aspects, the actual drug load for individual antibody molecules in the population of antibody-drug conjugate compounds is from 1 to 10 (or from 6 to 10 or from 6 to 8) with a predominant drug loading of 8. A higher drug load can be achieved, for example, if, in addition to the interchain disulfides, drug-linker is conjugated to introduced cysteine residues (such as a cysteine residue introduced at position 239, according to the EU index).

Exemplary ADCs include the following:

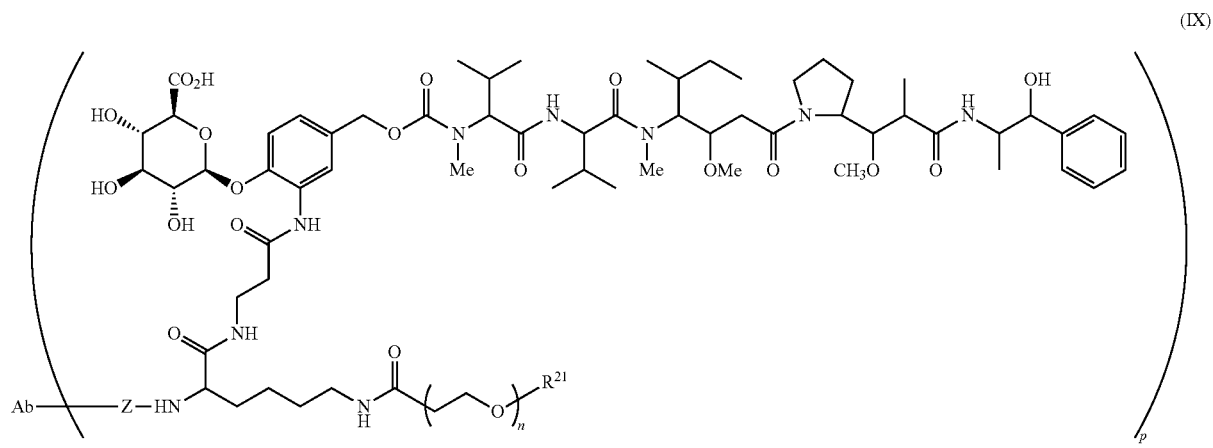

(IX)

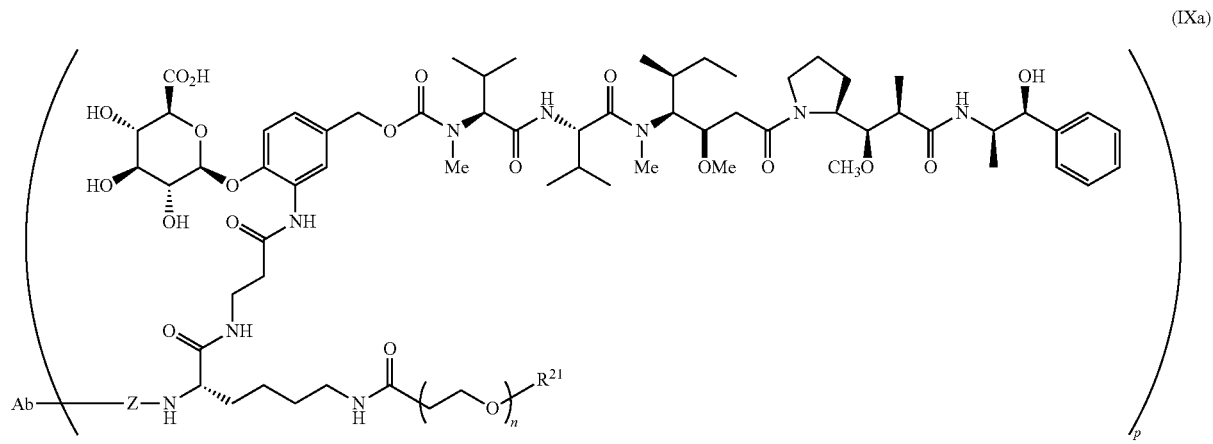

(IXa)

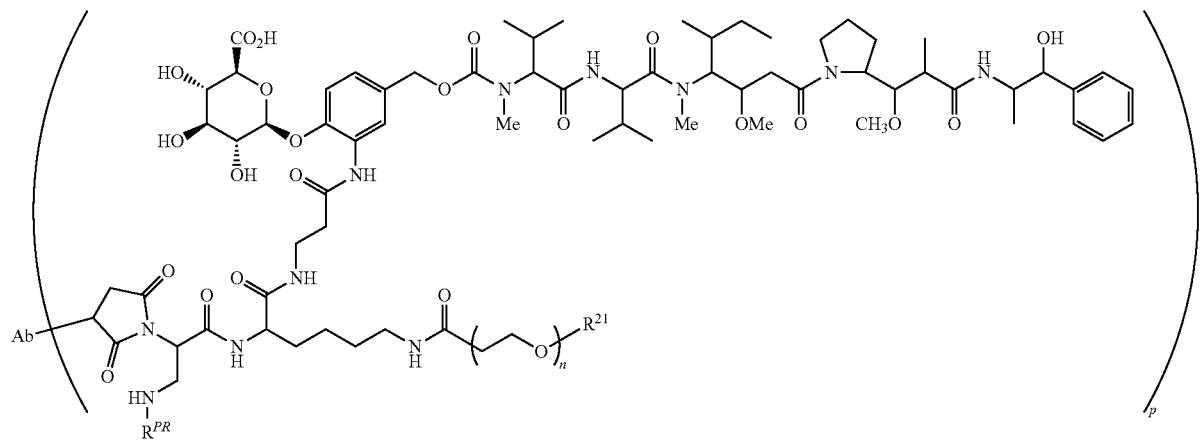
(X)
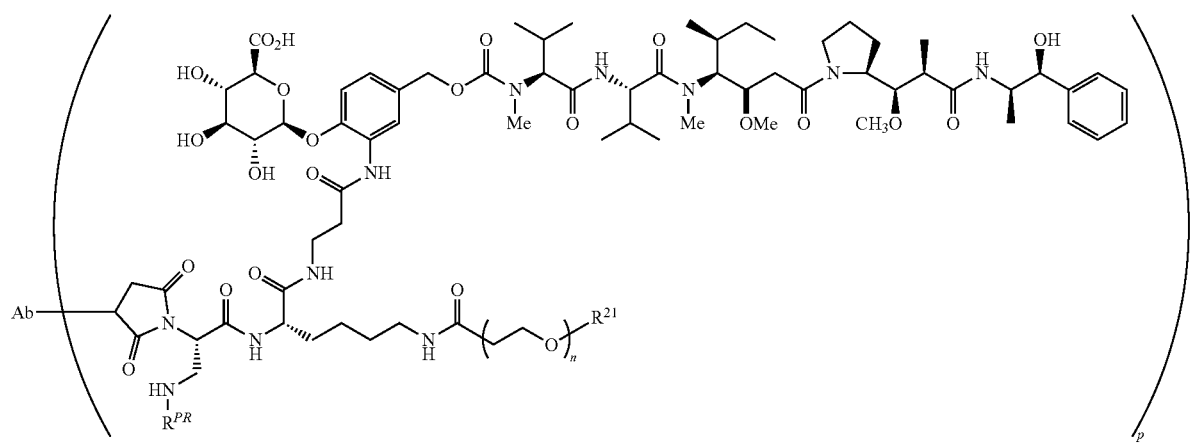
(Xa)
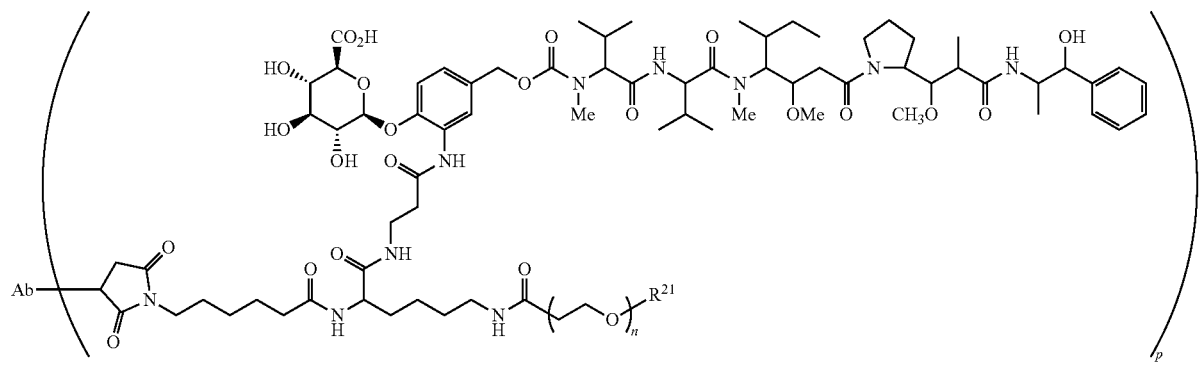
(XI)

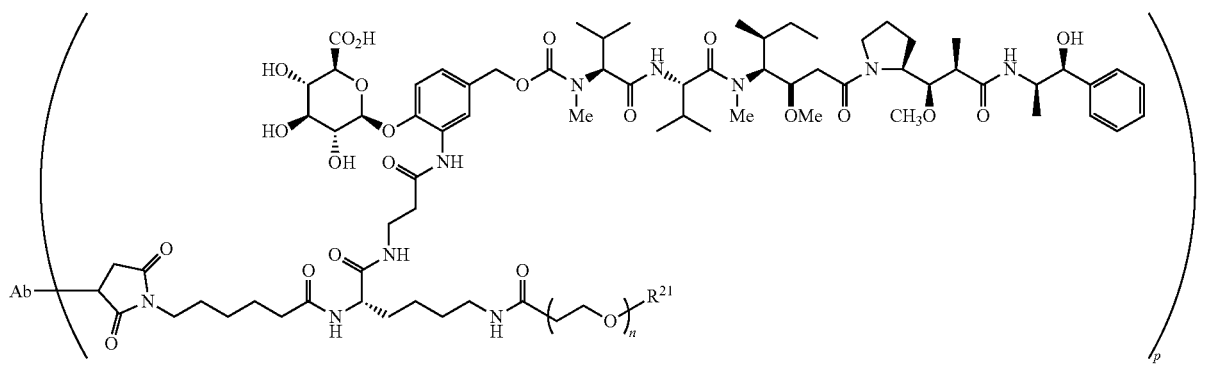

or a pharmaceutically acceptable salt thereof wherein n ranges from 8 to 36 and most preferably ranges from 8 to 14 (most preferably 12), $R^{PR}$ is hydrogen or a protecting group, e.g., acid labile protecting group, e.g., BOC, $R^{21}$ is a capping unit for the polyethylene glycol moiety, preferably -$CH_3$ or -$CH_2CH_2COH$, Ab represents an anti-αVβ6 antibody and p represents an integer ranging from 1 to 16, preferably 1 to 14, 6 to 12, 6 to 10, or 8 to 10 when referring to individual antibody molecules or to an average drug load of from about 4 or about 6 to about 14, preferably about 8 when referring to a population of antibody molecules.

As noted above, the PEG (polyethylene glycol) portion of the drug linker can range from 8 to 36, however, it has been found that a PEG of 12 ethylene oxide units is particularly preferably. It has been found that longer PEG chains can result in slower clearance whereas shorter PEG chains can result in diminished activity. Accordingly, the subscript n in all of the embodiments above is preferably 8 to 14, 8 to 12, 10 to 12 or 10 to 14 and is most preferably 12.

Polydisperse PEGS, monodisperse PEGS and discrete PEGs can be used to make the PEGylated antibody drug conjugates of the present invention. Polydisperse PEGs are a heterogenous mixture of sizes and molecular weights whereas monodisperse PEGs are typically purified from heterogenous mixtures and are therefore provide a single chain length and molecular weight. Preferred PEG Units are discrete PEGs, compounds that are synthesized in step-wise fashion and not via a polymerization process. Discrete PEGs provide a single molecule with defined and specified chain length. As with the subscript "p", when referring to populations of antibody-drug conjugates, the value for the subscript "n" can be an average number and can be an integer or non-integer number.

In preferred embodiments, covalent attachment of the antibody to the drug-linker is accomplished through a sulfhydryl functional group of the antibody interacting with a maleimide functional group of a drug linker to form a thio-substituted succinimide. The sulfhydryl functional group can be present on the Ligand Unit in the Ligand's natural state, for example, in a naturally-occurring residue (inter-chain disulfide resides), or can be introduced into the Ligand via chemical modification or by biological engineering, or a combination of the two. It will be understood that an antibody-substituted succinimide may exist in hydrolyzed form(s). For example, in preferred embodiments, an ADC is comprised of a succinimide moiety that when bonded to the antibody is represented by the structure of:

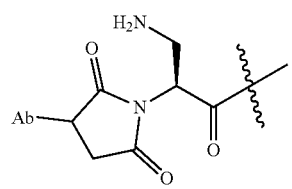

or is comprised of its corresponding acid-amide moiety that when bonded to the antibody is represented by the structure of:

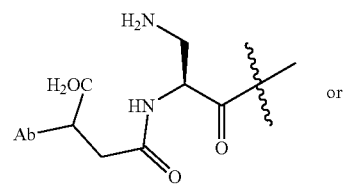

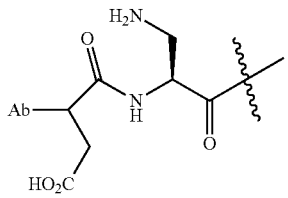

The wavy line indicates linkage to the remainder of the drug-linker.

In some embodiments, an anti-αvβ6 antibody of the invention is conjugated to monomethyl auristatin E via a MDpr-PEG(12)-gluc linker forming an antibody-drug conjugate having the structure:

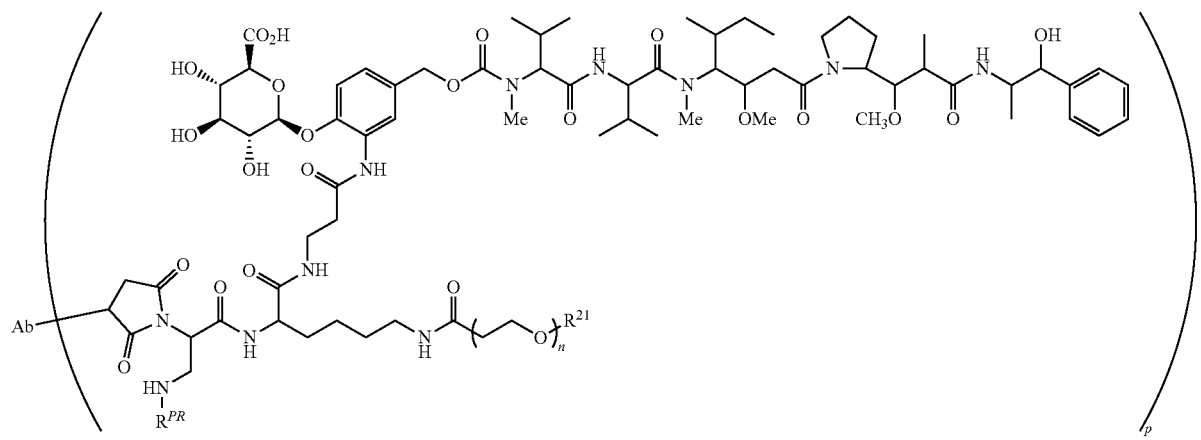

or a pharmaceutically acceptable salt thereof wherein n ranges from 8 to 36 and most preferably ranges from 8 to 14 (most preferably 12), $R^{PR}$ is hydrogen or a protecting group, e.g., acid labile protecting group, e.g., BOC. $R^{21}$ is a capping unit for the polyethylene glycol moiety, preferably-$CH_3$ or —$CH_2CH_2CO_2H$, Ab represents an anti-αVβ6 antibody and p represents an integer ranging from 1 to 16, preferably 1 to 14, 6 to 12, 6 to 10, or 8 to 10 when referring to individual antibody molecules or to an average drug load of from about 4 or about 6 to about 1.4, preferably about 8 when referring to a population of antibody molecules.

Exemplary antibody-drug conjugates also include camptothecin based antibody-drug conjugates (i.e., the drug component is a camptothecin drug). Camptothecins are topoisomerase inhibitors that have been shown to have anticancer activity. Typically the camptothecin based antibody-drug conjugate comprises a linker between the camptothecin drug and the anti-αvβ6 antibody. The linker can be, for example, a cleavable linker (e.g., a peptidyl linker, a carbohydrate linker) or a non-cleavable linker (e.g., linker released by degradation of the antibody). The synthesis and structure of exemplary camptothecin drug-linkers is described in PCT/US19/025968 (filed Apr. 5, 2019), which is incorporated herein by reference in its entirety and for all purposes.

Exemplary anti-αvβ6 antibody drug conjugates include camptothecin antibody drug conjugates as follows wherein p represents the drug load and Ab represents the anti-αvβ6 antibody:

In some embodiments, the camptothecin ADC has the formula (IC):

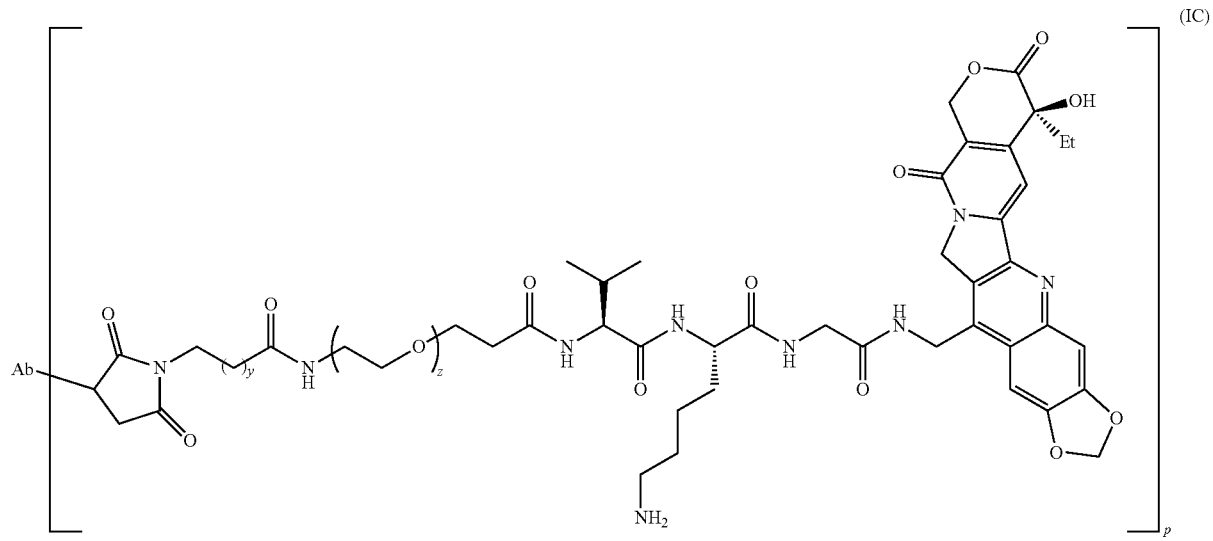

or a pharmaceutically acceptable salt thereof;
wherein
Ab is an anti-αvβ6 antibody;
y is 1, 2, 3, or 4, or is 1 or 4; and
z is an integer from 2 to 12, or is 2, 4, 8, or 12; and p is 1-16.

In some aspect of these embodiments, p is 2, 3, 4, 5, 6, 7, 8, 9, or 10. In some aspect, p is 2, 4 or 8.

In some embodiments, the camptothecin ADC has the formula:

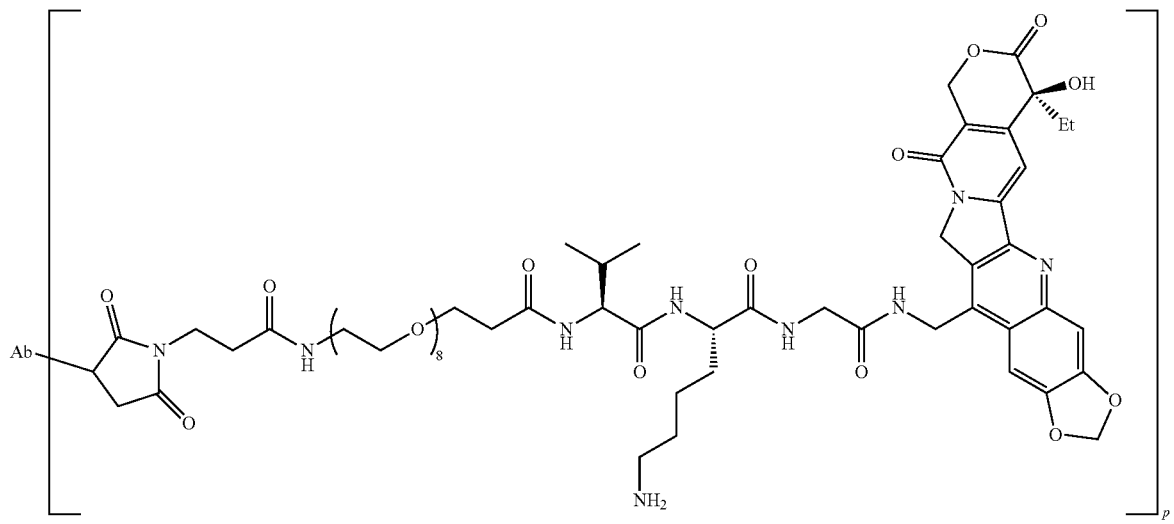

or a pharmaceutically acceptable salt thereof;
wherein p is 2, 4, or 8, preferably p is 8.

In some embodiments, the camptothecin ADC has the formula:

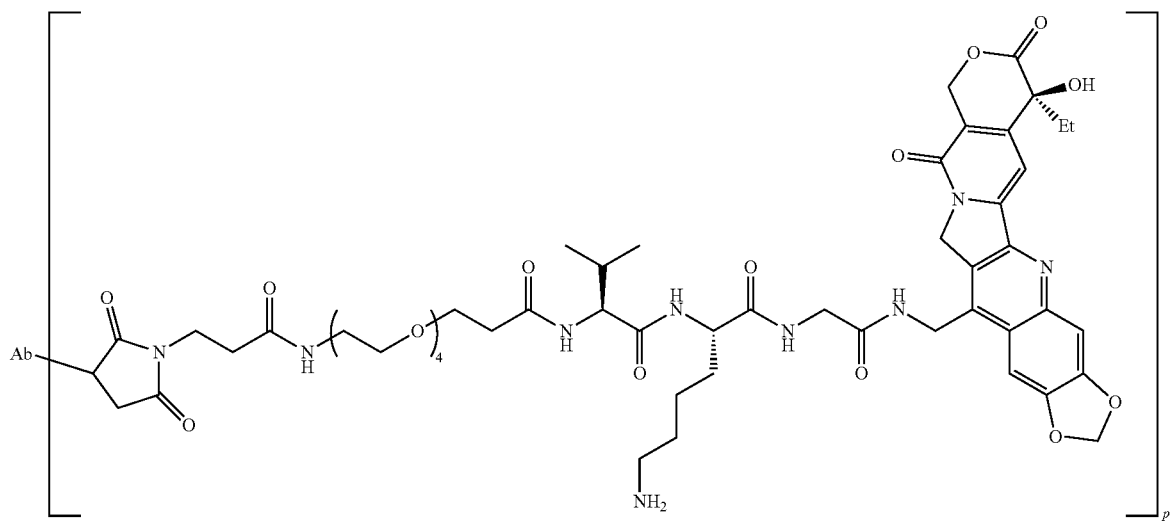

or a pharmaceutically acceptable salt thereof;
wherein p is 2, 4, or 8, preferably p is 8.

In some embodiments, the camptothecin drug-linker has the formula:
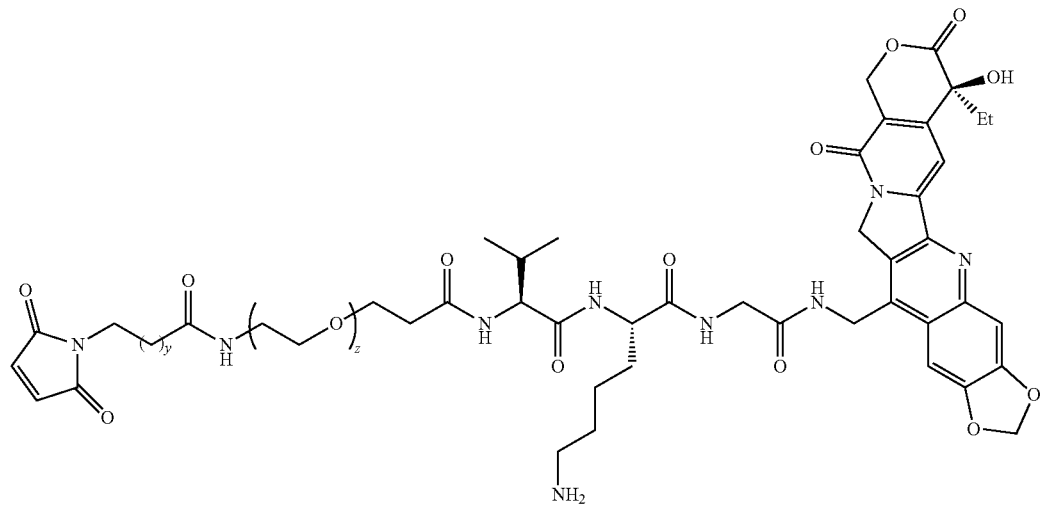
or a pharmaceutically acceptable salt thereof;
wherein
y is 1, 2, 3, or 4, or is 1 or 4; and
z is an integer from 2 to 12, or is 2, 4, 8, or 12.
In some embodiments, the camptothecin drug-linker has the formula:
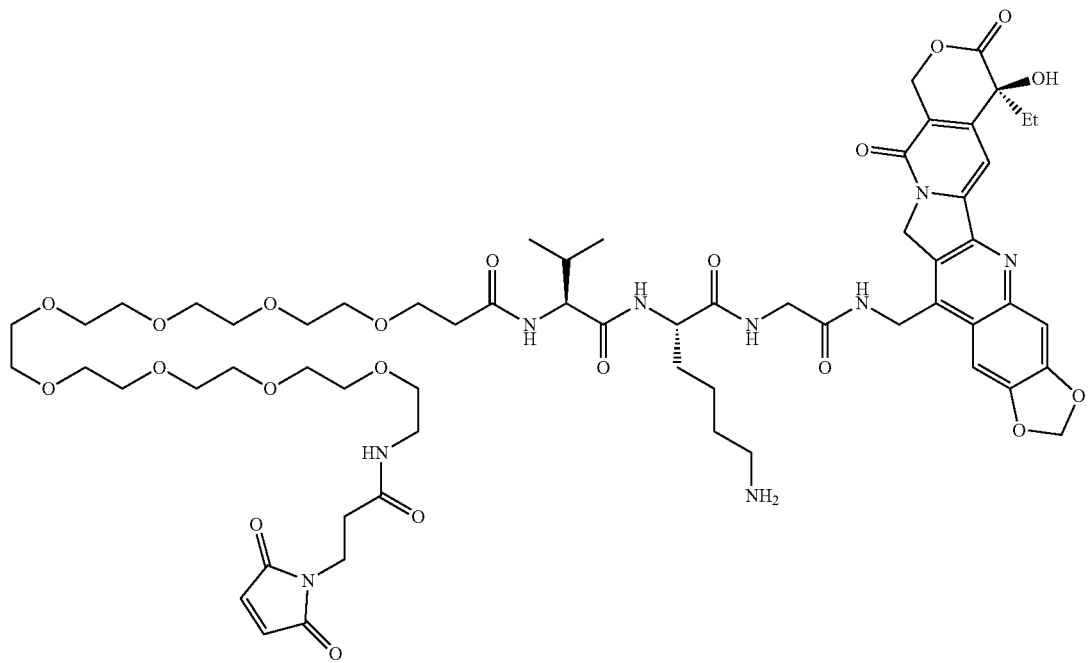
MP-PEG8-VKG-CAMPTOTHECIN

MP-PEG8-VKG-CAMPTOTHECIN

In some embodiments, the camptothecin drug-linker has the formula:

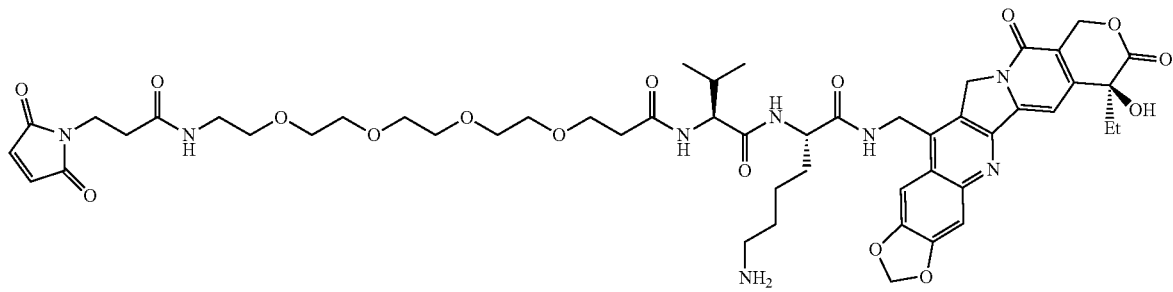

MP-PEG4-VKG-CAMPTOTHECIN

MP-PEG4-VKG-CAMPTOTHECIN

In some embodiments, the camptothecin drug-linker has the formula:

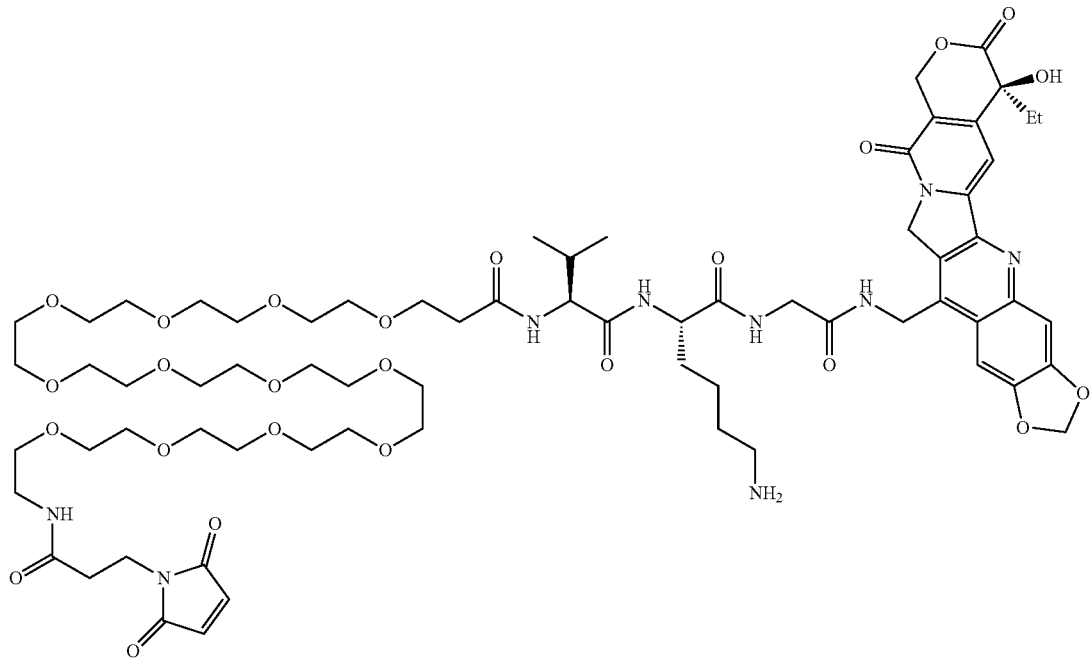

MP-PEG12-VKG-CAMPTOTHECIN

MP-PEG12-VKG-CAMPTOTHECIN

Other exemplary antibody-drug conjugates include maytansinoid antibody-drug conjugates (i.e., the drug component is a maytansinoid drug), and benzodiazepine antibody drug conjugates (i.e., the drug component is a benzodiazepine (e.g., pyrrolo[1,4]benzodiazepine dimers (PBD dimer), indolinobenzodiazepine dimers, and oxazolidinobenzodiazepine dimers)).

In some embodiments, a PBD dimer for use in the present invention is represented by formula I. The preferred stereochemistry of the PBD dimer is as shown in formula Ia:

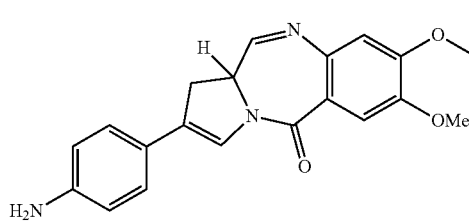
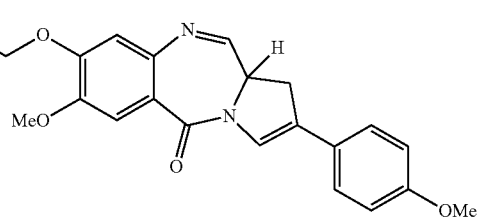

(I)

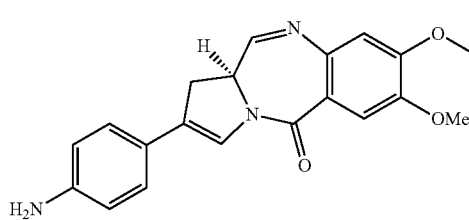
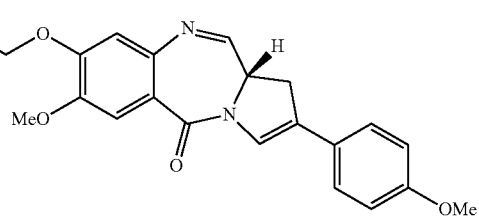

(Ia)

or a pharmaceutically salt, solvate, or solvate of the salt; wherein the subscript n is 1, or 3.

Solvates of formula (I) and (Ia) are typically formed from addition of water or alcoholic solvent across the imine functional group of one or both PBD monomers to form carbinolamine(s) and/or carbinolamine ethers. For example, at the N10-C11 position, there can be an imine (N=C), a carbinolamine(NH—CH(OH)), or a carbinolamine ether (NH—CH(OMe)) as represented by formulas I' and Ia' below:

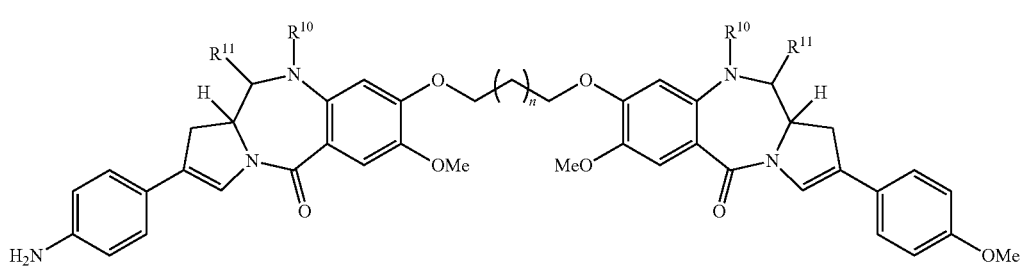

(I')

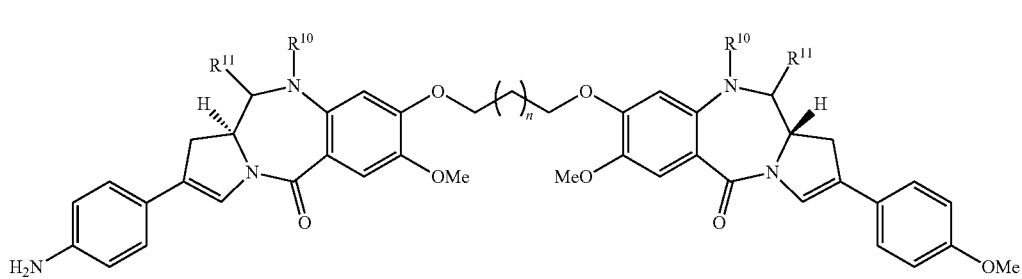

(Ia')

wherein either:
(a) $R^{10}$ is H, and $R^{11}$ is OH or $OR^A$, where $R^A$ is saturated $C_{1-4}$ alkyl (preferably methyl); or
(b) $R^{10}$ and $R^{11}$ form a nitrogen-carbon double bond between the nitrogen and carbon atoms to which they are bound; or
c) one of $R^{10}$ is H, and $R^{11}$ is OH or $OR^A$, where $R^A$ is saturated $C_{1-4}$ alkyl (preferably methyl); and the other of $R^{10}$ and $R^{11}$ form a nitrogen-carbon double bond between the nitrogen and carbon atoms to which they are bound.

The PBD dimer of formula I or 1a (or a pharmaceutically salt, solvate, or solvate of the salt thereof) is typically linked to the antibody via a Linker Unit, LU. The Linker Unit acts to release the PBD dimer of formula I or 1a (or a pharmaceutically salt, solvate, or solvate of the salt thereof) at the target site (e.g., inside the cancer cell). A PBD drug-linker compound for use in the present invention is represented below by formula II (preferred stereochemistry as shown in IIa) wherein LU is a Linker Unit. The Linker Unit can be, for example, a cleavable peptide Linker Unit (e.g., a linker comprising the valine-alanine peptide) or a cleavable disulfide Linker Unit:

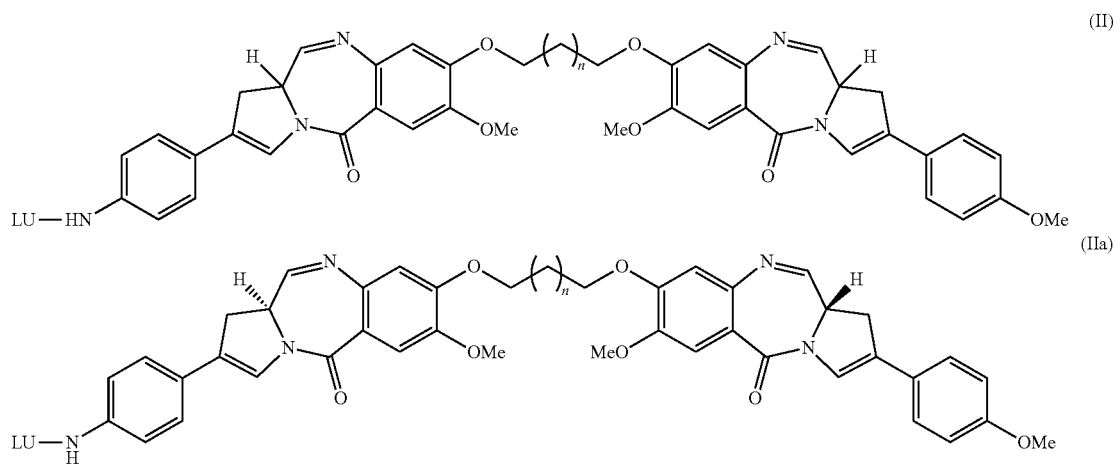

(II)

(IIa)

or a pharmaceutically salt, solvate, or solvate of the salt; wherein the subscript n is 1 or 3.

A preferred PBD drug-linker compound for use in the present invention is represented by Formula III below:

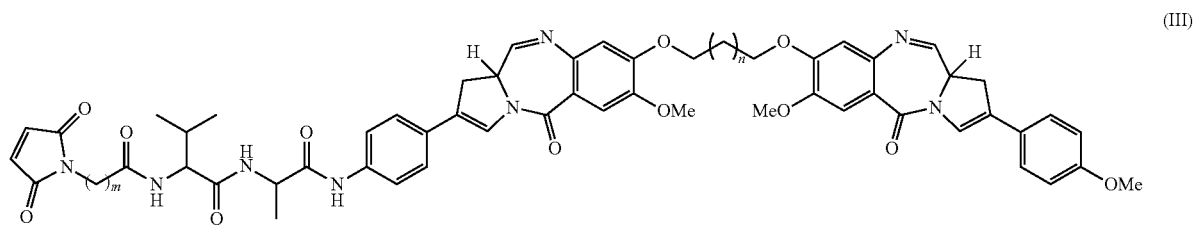

(III)

or a pharmaceutically salt, solvate or solvate of the salt; wherein the subscript n is 1 or 3 and the subscript m is an integer from 2 to 5.

The PBD drug-linker is conjugated to an anti-αvβ6 antibody to produce a αvβ6 targeted antibody-drug conjugate. For example, the antibody can be conjugated to a drug-linker of formula II or formula III. An exemplary αvβ6 targeted antibody-drug conjugate is shown below in formulas IV, IVa, and IVb:

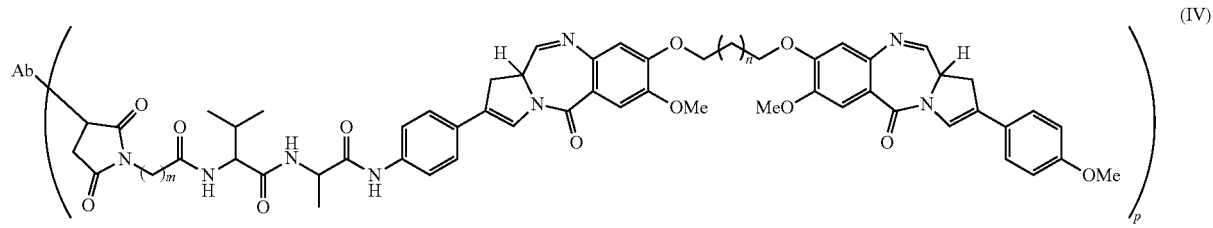

(IV)

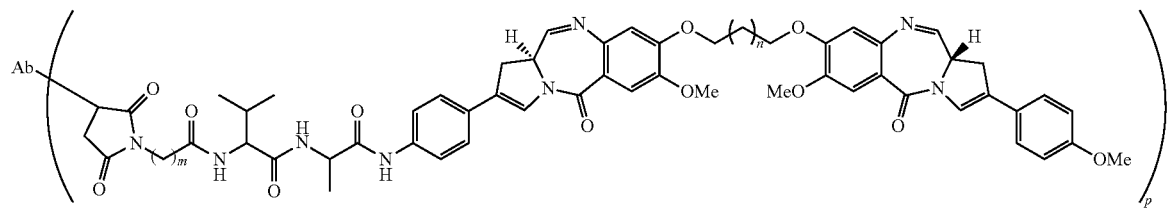

(IVa)

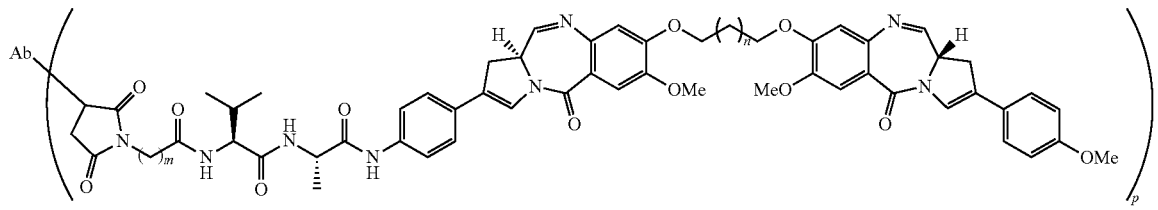

(IVb)

or a pharmaceutically salt, solvate, or solvate of the salt; wherein the subscript n is 1 or 3; the subscript m is an integer from 2 to 5; and the subscript p is from 1 to 4.

Useful classes of cytotoxic agents to conjugate to anti-αvβ6 antibodies include, for example, antitubulin agents, DNA minor groove binding agents, DNA replication inhibitors, chemotherapy sensitizers, or the like. Other exemplary classes of cytotoxic agents include anthracyclines, auristatins, camptothecins, duocarmycins, etoposides, maytansinoids and vinca alkaloids. Some exemplary cytotoxic agents include auristatins (e.g., auristatin T, auristatin E, AFP, monomethyl auristatin F (MMAF), lipophilic monomethyl aurstatin F, monomethyl auristatin E (MMAE)), DNA minor groove binders (e.g., enediynes and lexitropsins), duocarmycins, taxanes (e.g., paclitaxel and docetaxel), vinca alkaloids, nicotinamide phosphoribosyltranferase inhibitor (NAMPTi), tubulysin M, doxorubicin, morpholino-doxorubicin, and cyanomorpholino-doxorubicin.

The cytotoxic agent can be a chemotherapeutic such as, for example, doxorubicin, paclitaxel, melphalan, vinca alkaloids, methotrexate, mitomycin C or etoposide. The agent can also be a CC-1065 analogue, calicheamicin, maytansine, an analog of dolastatin 10, rhizoxin, or palytoxin.

The cytotoxic agent can also be an auristatin. The auristatin can be an auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatins include auristatin T, AFP, MMAF, and MMAE. The synthesis and structure of various auristatins are described in, for example, US 2005-0238649 and US2006-0074008.

The cytotoxic agent can be a DNA minor groove binding agent. (See, e.g., U.S. Pat. No. 6,130,237.) For example, the minor groove binding agent can be a CBI compound or an enediyne (e.g., calicheamicin).

The cytotoxic or cytostatic agent can be an anti-tubulin agent. Examples of anti-tubulin agents include taxanes (e.g., Taxol® (paclitaxel), Taxotere® (docetaxel)), T67 (Tularik), vinca alkyloids (e.g., vincristine, vinblastine, vindesine, and vinorelbine), and auristatins (e.g., auristatin E, AFP, MMAF, MMAE, AEB, AEVB). Exemplary auristatins are shown below in formulae III-XIII Other suitable antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermoide and eleuthrobin.

The cytotoxic agent can be a maytansinoid, another group of anti-tubulin agents (e.g., DM1, DM2, DM3, DM4). For example, the maytansinoid can be maytansine or a maytansine containing drug linker such as DM-1 or DM-4 (ImmunoGen, Inc.; see also Chari et al., 1992, Cancer Res.)

VIII. Therapeutic Applications

The antibodies of the invention, alone or as anti-αvβ6 antibody-drug conjugates thereof, can be used to treat cancer. Some such cancers show detectable levels of αvβ6 measured at either the protein (e.g., by immunoassay using one of the exemplified antibodies) or mRNA level. Some such cancers show elevated levels of αvβ6 relative to noncancerous tissue of the same type, preferably from the same patient. An exemplary level of αvβ6 on cancer cells amenable to treatment is 5000-500,000 αvβ6 molecules per cell, although higher or lower levels can be treated. Optionally, a level of αvβ6 in a cancer is measured before performing treatment.

Examples of cancers associated with αvβ6 expression and amenable to treatment include non-small cell lung cancer (NSCLC) (squamous and adeno), head and neck cancer (including head and neck squamous carcinoma), esophageal cancer, breast cancer (including breast invasive carcinoma), ovarian cancer, bladder cancer (including urothelial carcinoma), skin cancer (squamous cell carcinoma, or SCC), renal cancer (including renal clear cell, renal papillary cell, and kidney chromophobe), cervical cancer, gastric cancer, prostate cancer (including prostate adenocarcinoma), endometrial cancer (including uterine carcinosarcoma and uterine corpus endometrial), rectum adenocarcinoma, thyroid carcinoma, colon adenocarcinoma, stomach adenocarcinoma, and pancreatic cancer (including pancreatic adenocarcinoma). In some embodiments, the antibodies or antibody-drug conjugates of the invention are used in methods of treating NSCLC. In some embodiments, the antibodies or antibody-drug conjugates of the invention are used in methods of treating head and neck cancer. In some embodiments, the antibodies or antibody-drug conjugates of the invention are used in methods of treating skin cancer. In some embodiments, the antibodies or antibody-drug conjugates of the invention are used in methods of treating esophageal cancer. In some embodiments, the antibodies or antibody-drug conjugates of the invention are used in methods of treating breast cancer. In some embodiments, the antibodies or antibody-drug conjugates of the invention are used in methods of treating ovarian cancer. In some embodiments, the antibodies or antibody-drug conjugates of the invention are used in methods of treating bladder cancer. In some embodiments, the antibodies or antibody-drug conjugates of the invention are used in methods of treating cervical cancer. In some embodiments, the antibodies or antibody-drug conjugates of the invention are used in methods of treating gastric cancer. In some embodiments, the antibodies or antibody-drug conjugates of the invention are used in methods of treating renal cancer. In some embodiments, the antibodies or antibody-drug conjugates of the invention are used in methods of treating endometrial cancer. In some embodiments, the antibodies or antibody-drug conjugates of the invention are used in methods of treating stomach cancer. In some embodiments, the antibodies or antibody-drug conjugates of the invention are used in methods of treating pancreatic cancer. The treatment can be applied to patients having primary or metastatic tumors of these kinds. The treatment can also be applied to patients who are refractory to conventional treatments, or who have relapsed following a response to such treatments.

Antibodies of the present invention, such as humanized antibodies, alone or as conjugates thereof, are administered in an effective regime meaning a dosage, route of administration and frequency of administration that delays the onset, reduces the severity, inhibits further deterioration, and/or ameliorates at least one sign or symptom of cancer. If a patient is already suffering from cancer, the regime can be referred to as a therapeutically effective regime. If the patient is at elevated risk of the caner relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for a monoclonal antibody are 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kg 1, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg. Exemplary dosages for a monoclonal antibody or antibody drug conjugates thereof are 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. In some methods, the patient is administered a dose of at least 1.5 mg/kg, at least 2 mg/kg or at least 3 mg/kg, administered once every three weeks or greater. The dosage depends on the frequency of administration, condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody or conjugate in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between weekly or three out of every four weeks over a continuous course of treatment, although more or less frequent dosing is also possible. For subcutaneous administration, an exemplary dosing frequency is daily to monthly, although more or less frequent dosing is also possible.

The number of dosages administered depends on the nature of the cancer (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 1-100 mg/ml, such as 10 mg/ml.

Treatment with antibodies of the invention can be combined with chemotherapy, radiation, stem cell treatment, surgery other treatments effective against the disorder being treated. Useful classes of other agents that can be administered with antibodies and antibody-drug conjugates to αvβ6 as described herein include, for example, antibodies to other receptors expressed on cancerous cells, antitubulin agents (e.g., auristatins), DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Treatment with the anti-αvβ6 antibody or antibody-drug conjugate, optionally in combination with any of the other agents or regimes described above alone or as an antibody drug conjugate, can increase the median progression-free survival or overall survival time of patients with tumors (e.g., non-small cell lung cancer (NSCLC) (squamous and adeno), head and neck cancer (including head and neck squamous carcinoma), esophageal cancer, breast cancer (including breast invasive carcinoma), ovarian cancer, bladder cancer (including urothelial carcinoma), skin cancer (squamous cell carcinoma, or SCC), renal cancer (including renal clear cell, renal papillary cell, and kidney chromophobe), cervical cancer, gastric cancer, prostate cancer (including prostate adenocarcinoma), endometrial cancer (including uterine carcinosarcoma and uterine corpus endometrial), rectum adenocarcinoma, thyroid carcinoma, colon adenocarcinoma, stomach adenocarcinoma, and pancreatic cancer (including pancreatic adenocarcinoma)), especially when relapsed or refractory, by at least 30% or 40% but preferably 50%, 60% to 70% or even 100% or longer, compared to the same treatment (e.g., chemotherapy) but without an anti-αvβ6 antibody alone or as a conjugate. In addition or alternatively, treatment (e.g., standard chemotherapy) including the anti-αvβ6 antibody alone or as a conjugate can increase the complete response rate, partial response rate, or objective response rate (complete+partial) of patients with tumors by at least 30% or 40% but preferably 50%, 60% to 70% or even 100% compared to the same treatment (e.g., chemotherapy) but without the anti-αvβ6 antibody alone or as a conjugate.

Typically, in a clinical trial (e.g., a phase II, phase or phase III trial), the aforementioned increases in median progression-free survival and/or response rate of the patients treated with standard therapy plus the anti-αvβ6 antibody alone or as conjugate, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

IX. Articles of Manufacture and Kits

In another aspect, an article of manufacture or kit is provided which comprises an anti-αvβ6 antibody or anti-αvβ6 antibody-drug conjugate described herein. The article of manufacture or kit may further comprise instructions for use of the anti-αvβ6 antibody or anti-αvβ6 antibody-drug conjugate described herein in the methods of the invention. Thus, in certain embodiments, the article of manufacture or kit comprises instructions for the use of an anti-αvβ6 antibody or anti-αvβ6 antibody-drug conjugate described herein in methods for treating cancer (e.g., non-small cell lung cancer (NSCLC) (squamous and adeno), head and neck cancer (including head and neck squamous carcinoma), esophageal cancer, breast cancer (including breast invasive carcinoma), ovarian cancer, bladder cancer (including urothelial carcinoma), skin cancer (squamous cell carcinoma, or SCC), renal cancer (including renal clear cell, renal papillary cell, and kidney chromophobe), cervical cancer, gastric cancer, prostate cancer (including prostate adenocarcinoma), endometrial cancer (including uterine carcinosarcoma and uterine corpus endometrial), rectum adenocarcinoma, thyroid carcinoma, colon adenocarcinoma, stomach adenocarcinoma, and pancreatic cancer (including pancreatic adenocarcinoma)) in a subject comprising administering to the subject an effective amount of an anti-αvβ6 antibody or anti-αvβ6 antibody-drug conjugate described herein. In some embodiments, the cancer is NSCLC. In some embodiments, the cancer is head and neck cancer. In some embodiments, the cancer is esophageal cancer. In some embodiments, the cancer is breast cancer. In some embodiments, the cancer is ovarian cancer. In some embodiments, the antibodies or antibody-drug conjugates of the invention are used in methods of treating renal cancer. In some embodiments, the antibodies or antibody-drug conjugates of the invention are used in methods of treating endometrial cancer. In some embodiments, the antibodies or antibody-drug conjugates of the invention are used in methods of treating stomach cancer. In some embodiments, the cancer is bladder cancer. In some embodiments, the cancer is skin cancer. In some embodiments, the cancer is cervical cancer. In some embodiments, the cancer is gastric cancer. In some embodiments, the cancer is pancreatic cancer. In some embodiments, the subject is a human.

The article of manufacture or kit may further comprise a container. Suitable containers include, for example, bottles, vials (e.g., dual chamber vials), syringes (such as single or dual chamber syringes) and test tubes. In some embodiments, the container is a vial. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous (e.g., intravenous infusion), or other modes of administration for treating cancer in a subject (e.g., non-small cell lung cancer (NSCLC) (squamous and adeno), head and neck cancer (including head and neck squamous carcinoma), esophageal cancer, breast cancer (including breast invasive carcinoma), ovarian cancer, bladder cancer (including urothelial carcinoma), skin cancer (squamous cell carcinoma, or SCC), renal cancer (including renal clear cell, renal papillary cell, and kidney chromophobe), cervical cancer, gastric cancer, prostate cancer (including prostate adenocarcinoma), endometrial cancer (including uterine carcinosarcoma and uterine corpus endometrial), rectum adenocarcinoma, thyroid carcinoma, colon adenocarcinoma, stomach adenocarcinoma, and pancreatic cancer (including pancreatic adenocarcinoma)). The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

The article of manufacture or kit herein optionally further comprises a container comprising a second medicament, wherein the anti-αvβ6 antibody or anti-αvβ6 antibody-drug conjugate is a first medicament, and which article or kit further comprises instructions on the label or package insert for treating the subject with the second medicament, in an effective amount. In some embodiments, the second medicament is for eliminating or reducing the severity of one or more adverse events.

In some embodiments, the anti-αvβ6 antibody or anti-αvβ6 antibody-drug conjugate is present in the container as a lyophilized powder. In some embodiments, the lyophilized powder is in a hermetically sealed container, such as a vial, an ampoule or sachette, indicating the quantity of the active agent. Where the pharmaceutical is administered by injection, an ampoule of sterile water for injection or saline can be, for example, provided, optionally as part of the kit, so that the ingredients can be mixed prior to administration. Such kits can further include, if desired, one or more of various conventional pharmaceutical components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components can also be included in the kit.

X. Other Applications

The anti-αvβ6 antibodies described herein, such as humanized anti-αvβ6, antibodies can be used for detecting αvβ6 in the context of clinical diagnosis or treatment or in research. Expression of αvβ6 on a cancer provides an indication that the cancer is amenable to treatment with the antibodies of the present invention. The antibodies can also be sold as research reagents for laboratory research in detecting cells bearing αvβ6 and their response to various stimuli. In such uses, monoclonal antibodies can be labeled with fluorescent molecules, spin-labeled molecules, enzymes or radioisotopes, and can be provided in the form of kit with all the necessary reagents to perform the assay for αvβ6. The antibodies described herein, can be used to detect αvβ6 protein expression and determine whether a cancer is amenable to treatment with αvβ6 ADCs.

All patent filings, website, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Materials

Cell lines described in the following examples were maintained in culture according to the conditions specified by the American Type Culture Collection (ATCC), the National Cancer Institute (NCI) or the Deutsche Sammlung von Mikroorganismen and Zellkulturen GmbH, Braunschweig, Germany (DMSZ). SW780 cell lines, Detroit 562 cell lines, HPAFII cell lines, and BxPC3 cell lines were obtained from ATCC. FreeStyle™ 293-F (InVitrogen Corp) human epithelial kidney cells and corresponding transfectants were maintained as described by the manufacterer. Cell culture reagents were obtained from Invitrogen Corp. (Carlsbad, Calif.), Molecular Devices (Sunnydale, Calif.) and other suppliers. Secondary antibody reagents were purchased from Jackson ImmunoResearch Laboratories (West Grove, Pa.). Recombinant αvβ1, αvβ3 αvβ5, αvβ6, and αvβ8 were purchased from R&D Systems (Minneapolis, Minn.). FreeStyle™ 293-F cells express endogenous integrin αv and they were stably transfected with a full length cDNA encoding human, cynomolgus or murine integrin β6 to generate HEK293F:huβ6, HEK293F:cynoβ6 and HEK293F:muβ6 cell lines, respectively. HEK293F cells transfected with the empty vector (HEK293F:vector) were used as a negative control. Mouse 3T3 and FDC-P1 cells that express endogenous mouse integrin αv were transfected with a full-length cDNA clone for human and mouse integrin β6 to generate 3T3:huβ6 and FDC-P1:muβ6, respectively.

Methodologies:
Generation of 2A2 Antibody

ICR (CD-1) mice were immunized three times with intraperitoneal injections of ~5×10$^6$ 3T3:huβ6 transfectants. Three days prior to fusion, mice received a final injection of purified recombinant human αvβ6 that was given intravenously (6 ug) and intraperitoneally (30 ug). Lymphocytes harvested from spleen and lymph nodes were fused to P3X63Ag8.653 myeloma cells using polyethylene glycol. Fused cells were recovered overnight in hybridoma growth media (IMDM containing 4 mM glutamine, 10% Fetal Clone I, 10% Cloning Factor and Penicillin/Streptomycin). Following recovery, cells were spun down and then plated in semi-solid media. Semi-solid media consisted of CloneMatrix media supplemented with hybridoma growth media plus HAT for hybridoma selection and CloneDetect for IgG-production. Hybridomas were incubated for 10 days at 37° C. At day 10, IgG producing hybridoma clones were picked using a ClonePixFL (Molecular Devices) and transferred to 96-well plates containing IgG-depleted hybridoma growth media plus HT. Hybridoma culture supernatants were screened on 293F:huβ6 transfectants and positive clones were identified using an Alexifluor-647 labeled secondary antibody for detection. The plates were read in an FMAT 8200 (Applied Biosystems). Hybridomas that bound to 293F:huβ6 and 293F:cynoβ6 but not 293F:vector were expanded for direct conjugation to drug-linkers. The directly conjugated antibody panel was tested in binding and cytotoxicity assays.

LAP Blockade ELISA 96-well microtiter plates (Nunc) were coated overnight at 4° C. with 0.3 ug/mL recombinant human latency-associated peptide (rhuLAP) (made in-house; Lot 09-19-09DS) in 1×PBS. Following removal of coating solution, plates were blocked with 3% BSA in Tris-buffered saline (TBS) for one hour room at temperature and then washed 5× with PBS+ 0.05% Tween-20 (PBST) prior to use. In a separate conical bottom 96-well plate, 0.25 ug/mL of recombinant human (rhu) αvβ6-biotin (made in-house rhuαvβ6-biotin, Lot #171030A) was pre-incubated for 1 hour at room temperature with increasing concentrations of purified antibody in TBS buffer containing 1 mM $CaCl_2$, 1 mM $MgCl_2$ and 1 mg/mL BSA for 1 hour at room temperature. The antibody/αvβ6-biotin mixture was then transferred to the LAP-coated plate and incubated at room temperature for 1 hour. Plates were washed as above and incubated with 50 uL/well of peroxidase conjugated strepatvidin (Jackson ImmunoResearch #016-030-084) diluted 1:1000 in TBS+1 mg/mL BSA at room temperature for 1 hour. Bound protein and signal was detected using TMB (Invitrogen #00-2023) incubated for 5.5 minutes and then quenched with 1N $H_2SO_4$ (Fisher #SA212-1). Plates were immediately read on plate reader (Molecular Devices Vmax Kinetic Microplate Reader) at 450 nm wavelength. Data were exported into Microsoft Excel and analyzed using GraphPad Prism v5.03.

Competition Binding Assays—Humanized 2A2 Antibody Variants

Competition binding assays were done using the 293F:huβ6 cell line. 0.1×10$^6$ antigen expressing cells were aliquoted in each well of a 96-well v-bottom plate on ice. The cells were incubated for 1 hour with 2 nM AlexaFluor-647 labeled m2A2 and increasing concentrations (from 0.03-500 nM) of unlabeled humanized 2A2 variant antibodies in FACS buffer (Tris-buffered saline, 2% fetal bovine serum, 0.5 mM $MnCl_2$, 0.02% NaN3). Cells were pelleted and washed 3 times with TBS/FBS. The cells were pelleted and resuspended in 125 uL of TBS/FBS. Fluorescent signal of binding was detected using a Becton Dickinson Biosciences LSR II (San Jose, Calif.). Percent of saturated fluorescent signal was used to determine percent labeled humanized 2A2 antibody bound and to subsequently extrapolate the EC50 by fitting the data to a sigmoidal dose-response curve with variable slope using GraphPad Software (LaJolla, Calif.).

Competition Binding Assays—Human and Cyno Δvβ6

Competition binding assays were done using the 293F:huβ6 and HEK293F:cynoβ6 cell lines. $0.1 \times 10^6$ antigen expressing cells were aliquoted in each well of a 96-well v-bottom plate on ice. The cells were incubated for 1 hour with 2 nM AlexaFluor-647 labeled humanized 2A2 HCLG and increasing concentrations (from 4 pM-1 uM) of unlabeled humanized 2A2 HCLG antibody and h2A2-Mdpr-PEG(12)-gluc-MMAE(8) in buffer (Tris-buffered saline, 2% fetal bovine serum, 0.5 mM $MnCl_2$, 0.02% NaN3). Cells were pelleted and washed 3 times with TBS/FBS. The cells were pelleted and resuspended in 125 uL of TBS/FBS. Fluorescent signal of binding was detected using a Becton Dickinson Biosciences LSR II (San Jose, Calif.). Percent of saturated fluorescent signal was used to determine percent labeled humanized 2A2 antibody bound to cells and to subsequently extrapolate the EC50 by fitting the data to a sigmoidal dose-response curve with variable slope using GraphPad Software (LaJolla, Calif.).

αvβ6 Saturation Binding Assays—Human and Cyno αvβ6

Saturation binding studies were done using the following antigen expressing cell lines: 293F:huβ6 and 293F:cynoβ6. $0.1 \times 10^6$ antigen expressing cells were aliquoted per well into a 96-well v-bottom plate. m2A2 and h2A2 HCLG were directly labeled with AlexaFluor-647 and added to cells at concentrations ranging from 6 pM-340 nM in buffer (Tris-buffered saline, 2% fetal bovine serum, 0.5 mM $MnCl_2$, 0.02% NaN3). Cell were incubated for 1 hour then pelleted and washed 3 times with TBS. The cells were pelleted and resuspended in 120 uL of TBS. Fluorescent signal of binding was detected using a Becton Dickinson Biosciences LSR II (San Jose, Calif.). The EC50 was calculated using GraphPad Software (LaJolla, Calif.).

ELISA 96-well Maxisorb plates (Nunc) were coated overnight at 4° C. with 1 ug/ml of recombinant human αvβ1, αvβ3, αvβ5, αvβ6 and αvβ8 (R&D Systems, MN) diluted in 50 mM carbonate buffer (Sigma, MO). Plates were washed with PBS+0.05% Tween 20 (PBS-T). Wash buffer was removed and plates were blocked for 2 hours at room temperature in TBS blocking buffer (TBS, 0.05% Tween 20, 1% BSA). Plates were washed and then incubated for 2 hours with humanized 2A2 antibody diluted in TBS binding buffer (TBS, 0.05% Tween 20, 1% BSA, 1 mM $MnCl_2$) at concentrations that ranged from 1 pM-67 nM (10 ug/ml). Plates were washed, incubated for 1 hour with 1:5000 dilution of anti-human Fc-HRP (Jackson ImmunoResearch, PA), washed, and then incubated with TMB substrate for 5 minutes. The reaction was stopped with 1 M HCl. Absorbance at 450 nm was read using a Fusion HT plate reader (Perkin Elmer, Waltham, Mass.).

Quantitative Flow Cytometric Analysis

Quantification of αvβ6 copy number on the cell surfaces was determined using murine αvβ6 mAb as primary antibody and the DAKO QiFiKit flow cytometric indirect assay as described by the manufacturer (DAKO A/S, Glostrup, Denmark) and evaluated with a Becton Dickinson FACScan flow cytometer.

In Vitro Cytotoxicity Assay

Tumor cells were incubated with anti-αvβ6 antibody drug conjugates for 96 hours at 37° C. Cell viability was determined using the CellTiter-Glo® luminescent assay (Promega Corporation, Madison, Wis.) and results were measured on an EnVision Multilabel plate reader (Perkin Elmer, Waltham, Mass.). Results are reported as IC50, defined as the concentration that results in half maximal growth inhibition over the course of the titration curve.

Production of Antibody-Drug Conjugates

Antibody drug conjugates of the anti-αvβ6 antibodies were prepared as described in US20050238649 and WO2015/057699. The drug linkers vcMMAE (also known as 1006) and mcMMAF are both described in US20050238649, which is incorporated herein by reference for all purposes. The drug linker MDpr-Lys(PEGx)-glucuronide-MMAE linker is described in WO2015/057699, which is incorporated herein by reference for all purposes.

In Vivo Activity Study

For therapy experiments in cell-line derived xenografts, $5 \times 10^6$ cells (ATCC) were injected subcutaneously into 5-8 female nude (nu/nu) mice (Envigo) for the BxPC3, Detroit 562, HPAF-II, and SW780 studies. Mice were randomly divided into study groups and dosed with test article via intraperitoneal injection once the tumors reached approximately 100 $mm^3$. Animals were euthanized when tumor volumes reached 500-1000 $mm^3$. Tumor volume was calculated with the formula (volume=½×length×width×width). Mice showing durable regressions were terminated around day 40-65 after implant. In all xenograft studies, no weight loss or treatment-related toxicities were observed for mice treated with any of the test articles. All animal procedures were performed under a protocol approved by the Institutional Animal Care and Use Committee in a facility accredited by the Association for Assessment and Accreditation of Laboratory Animal Care.

In addition to the cell-line derived xenografts, the antitumor activity of an h2A2 vcMMAE ADC against patient-derived xenograft (PDX) models of non-small cell lung cancer (NSCLC) was studied using models maintained by Champions Oncology (Hackensack N.J.). These PDX models include NSCLC samples of both adeno and squamous histology. These models were established by implantation in immunocompromised mice and allowed to grow to a tumor volume of 150-300 $mm^3$, then mice were randomized into treatment and control groups and dosed with the h2A2 vcMMAE or non-binding control h00 vcMMAE ADCs. Mice were dosed with 3 mg/kg of ADC weekly for a total of three doses. Tumor volumes were measured twice weekly for 28 days after the first dose, or until tumors reach a volume of 1500 $mm^3$.

The antitumor activity of h2A2 vcMMAE ADC was further evaluated in PDX models of ovarian carcinoma models maintained by Champions Oncology (Hackensack N.J.). These models were established by implantation in immunocompromised mice and allowed to grow to a tumor volume of 150-300 $mm^3$, then mice were randomized into treatment and control groups and dosed with the ADC. Mice were dosed with 5 mg/kg of ADC weekly for a total of three doses. Tumor volumes were measured twice weekly for 28 days after the first dose, or until tumors reach a volume of 1500 $mm^3$ up to a maximum of 60 days.

Results

The murine clone m2A2 was selected from the hybridoma panel because it showed cytotoxic activity as an ADC on multiple αvβ6-positive tumor cell lines and it had comparable affinity to human and cynomolgus forms of the antigen. The specificity of mouse 2A2 was confirmed in FMAT and flow cytometry binding studies where the antibodies were shown to bind to 293F:huβ6 transfectants but not to the αvβ5-positive parental line (293F:vector). Integrin αvβ6 has been shown to be a receptor for RGD sites in fibronectin (Weinacker et al., 1994), tenascin (Prieto et al., 1993), vitronectin (Huang et al. 1998) and latency-associated peptide (LAP) (Munger et al. 1999). Binding of integrin αvβ6 to LAP can induce the spatially restricted activation of transforming growth factor beta1 (TGFβ) (Munger et al. 1999). A latency-associated peptide (LAP) blockade assay was performed (FIG. 1), showing that m2A2 (SG-44.2A2) does not block LAP, in contrast to anti-αvβ6 antibodies m15H3 (SG-42.15H3) (see WO2013/123152) and positive control 10D5. This suggests that the 2A2 antibody can be delivered independent of ligand binding. The negative control was a non-binding IgG control, and SG-44.8B9, SG-33.20B8, SG-44.32A6, and SG-44.34D6 were other clones selected from the hybridoma panel.

Binding of Mouse Antibody

Figure 2:
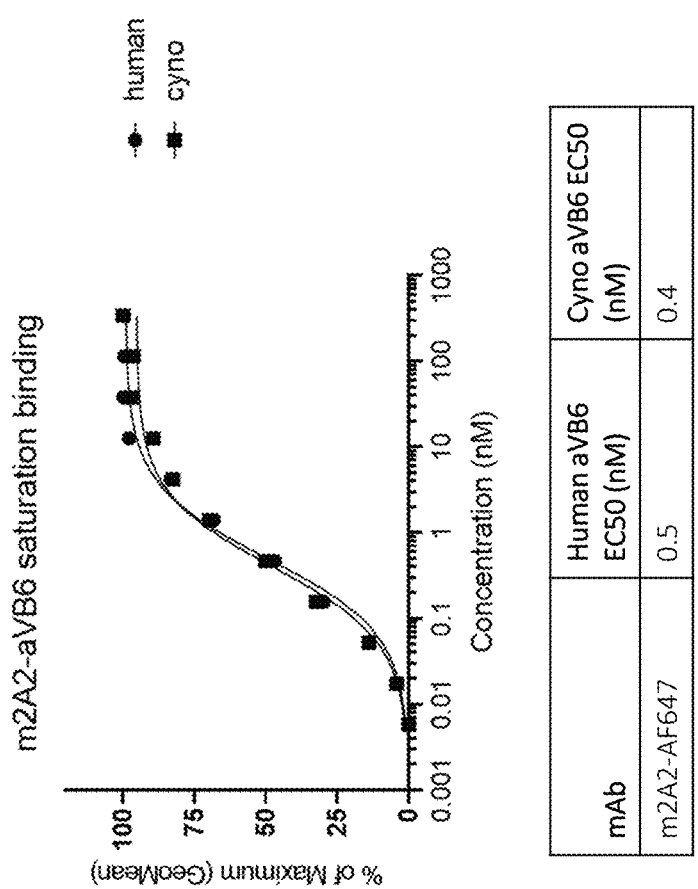
FIG. 2 shows the results of saturation binding studies on 293F cells expressing human and cyno αvβ6 with the murine antibody clone 2A2 (referred to as m2A2).

The EC50 for binding of the murine monoclonal antibody 2A2 was determined for human and cyno αvβ6 by saturation binding studies using genetically engineered cell lines (293F:huβ6, 293F:cynoβ6) (FIG. 2). The genetically engineered cell lines express endogenous αv which pairs with the recombinant β6 chain to produce a heterodimeric receptor composed of endogenous αv and recombinant β6.

Design and Selection of Humanized Antibodies

The starting point or donor antibody for humanization in this example is the murine 2A2 antibody. Genomic sequences provided by IGHV1-46 and IGHJ4 for the heavy chain and by IGKV1D-33 and IGKJ2 for the light chain were used.

In humanization, ten positions were identified in the heavy chain framework (H2, H28, H48, H67, H69, H71, H73, H74, H78, H93; FIG. 3) and two positions were identified in the light chain framework (L69 and L71; FIG. 4) at which the human acceptor sequence differed from the donor sequence and that may affect antibody binding as a result of contacting antigen directly, affecting conformation of CDRs or affecting packing between heavy and light chains. Four humanized heavy chain variants (vHA, vHB, vHC, vHD; FIG. 3) and eight humanized light chain variants (vLA, vLB, vLC, vLD, vLE, vLF, vLG, vLH; FIG. 4) were made incorporating back mutations at different permutations of these positions. These back mutations are specified in Tables 1-4. The remainder of the framework positions are occupied by the residues from the human acceptor sequence.

TABLE 1

Humanizing Mutations in h2A2 Heavy Chain Variants

| vH Variant | HV Exon Acceptor Sequence | Murine Donor Framework Residues | Human Acceptor CDR Residues |
|---|---|---|---|
| hvHA | IGHV1-46/HJ4 | H2, H28, H93 | none |
| hvHB | IGHV1-46/HJ4 | H2, H28, H74, H93 | none |
| hvHC | IGHV1-46/HJ4 | H2, H28, H48, H67, H69, H71, H73, H78, H93 | none |
| hvHD | IGHV1-46/HJ4 | H2, H28, H48, H67, H69, H71, H73, H74, H78, H93 | none |

TABLE 2

Specific Murine Framework Mutations in h2A2 Heavy Chain Variants

| Variant | 2 | 28 | 48 | 67 | 69 | 71 | 73 | 74 | 78 | 93 | % Human |
|---|---|---|---|---|---|---|---|---|---|---|---|
| hvHA | F | S | | | | | | | | T | 85.7 |
| hvHB | F | S | | | | | | P | | T | 84.7 |
| hvHC | F | S | I | A | L | V | K | | A | T | 79.6 |
| hvHD | F | S | I | A | L | V | K | P | A | T | 78.6 |

TABLE 3

Humanizing Mutations in h2A2 Kappa Light Chain Variants

| vK Variant | KV Exon Acceptor Sequence | Murine Donor Framework Residues | Human Acceptor CDR Residues |
|---|---|---|---|
| hvLA | IGKV1D-33/KJ2 | none | none |
| hvLB | IGKV1D-33/KJ2 | L69, L71 | none |
| hvLC | IGKV1D-33/KJ2 | L69, L71 | L56 |
| hvLD | IGKV1D-33/KJ2 | L71 | none |
| hvLE | IGKV1D-33/KJ2 | L69, L71 | L24 |
| hvLF | IGKV1D-33/KJ2 | L71 | L24, L56 |
| hvLG | IGKV1D-33/KJ2 | L69, L71 | L55 |
| hvLH | IGKV1D-33/KJ2 | L69 | none |

TABLE 4

Specific Murine Framework Mutations in h2A2 Kappa Light Chain Variants

| Variant | 69 | 71 | % Human |
|---|---|---|---|
| hvLA | | | 84.2 |
| hvLB | R | Y | 82.1 |
| hvLC | R | Y | 83.2 |
| hvLD | | Y | 83.2 |
| hvLE | R | Y | 83.2 |
| hvLF | | Y | 85.3 |
| hvLG | R | Y | 83.2 |
| hvLH | R | | 83.2 |

Figure 5:
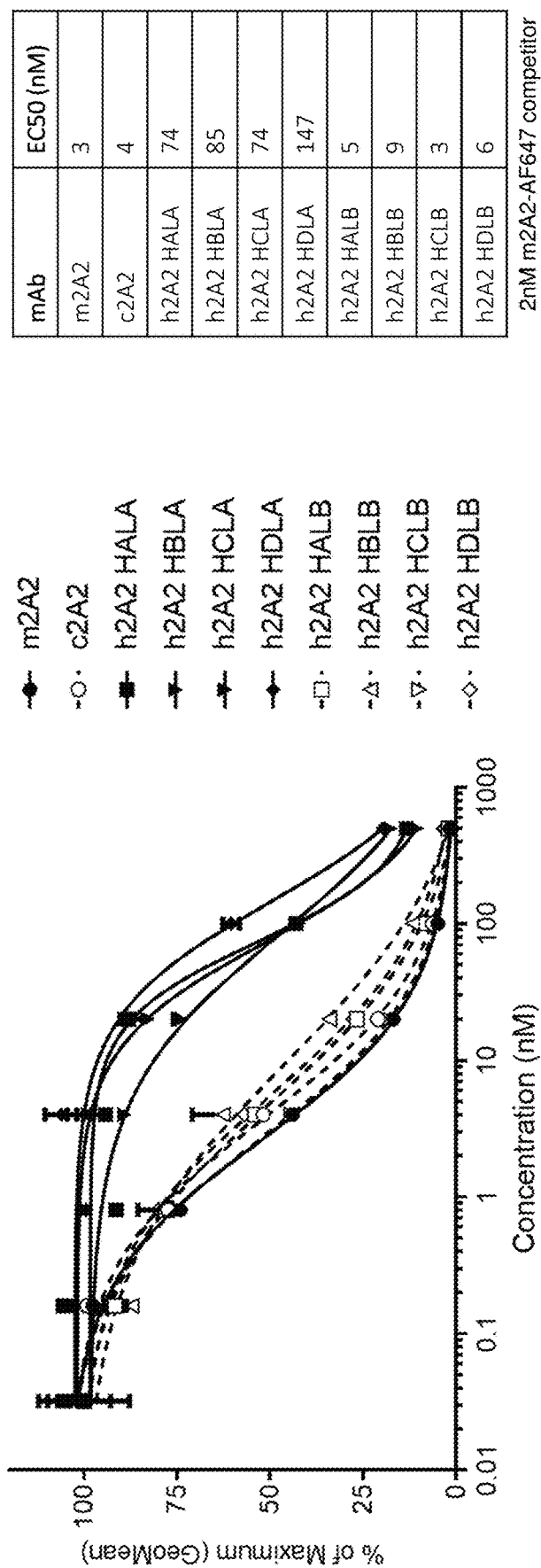
FIG. 5 shows the results of competition binding studies on 293F cells expressing human αvβ6 with humanized antibodies having the LA and LB light chains and the parental murine and chimeric antibodies (referred to as m2A2 and c2A2, respectively).
Figure 6:
FIG. 6 shows the results of competition binding studies on 293F cells expressing human αvβ6 with humanized antibodies having the HA and HC heavy chains and the parental murine and chimeric antibodies (referred to as m2A2 and c2A2, respectively).
Figure 7:
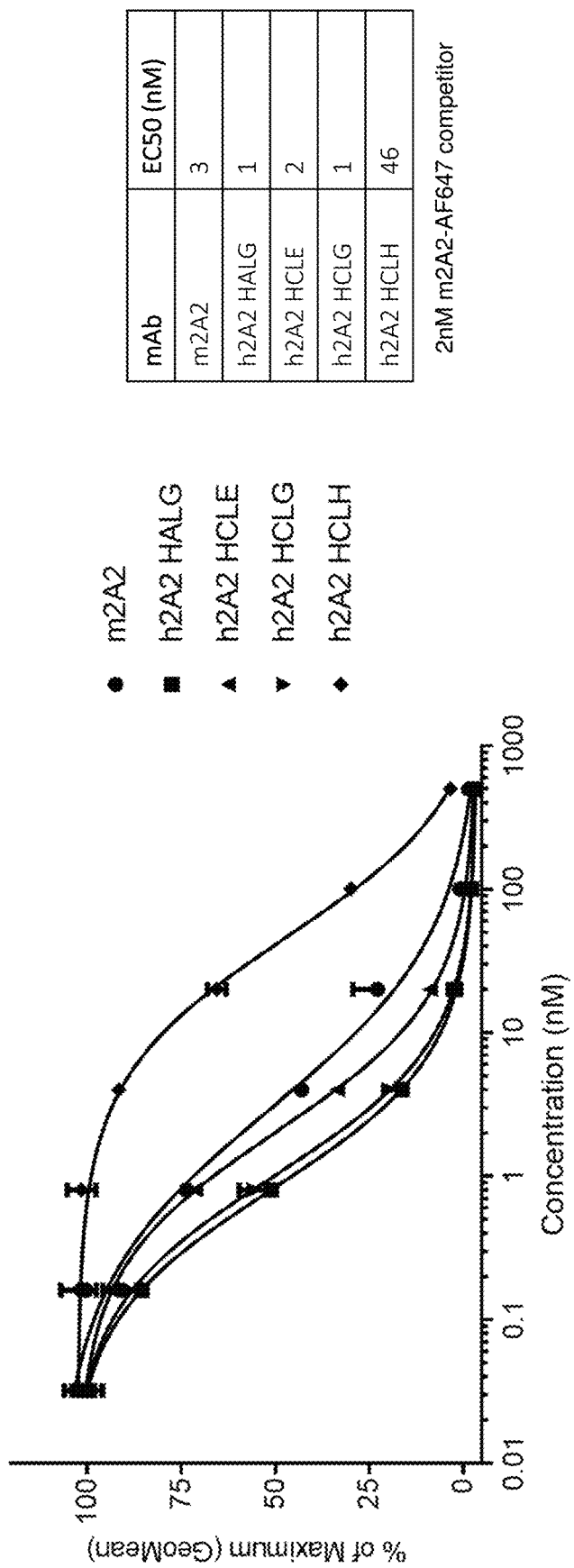
FIG. 7 shows the repeated results of competition binding studies on 293F cells expressing human αvβ6 with a subset of humanized antibodies and the parental murine antibody (referred to as m2A2).

Humanized antibodies were then expressed representing combinatorial permutations of these humanized heavy and light chain variants. The competition binding curves of the resulting humanized antibody variants (alongside the murine 2A2 antibody and a human-murine chimeric antibody) to human αvβ6 are shown in FIGS. 5-7. Four humanized variants were selected for further analysis in an in vitro activity assay. In vitro anticancer activity of humanized variants HCLE, HCLG, HCLH, HALG, and humanized anti-αvβ6 antibody 15H3-HTLC (each conjugated to a drug-linker. Via, n=12, $R^{PR}$=H, $R^{21}$=$CH_3$) was measured using cytotoxicity assays in four cell lines expressing αvβ6 at a variety of levels based on quantitative flow cytometry analysis (pancreatic cancer HPAFII and BxPC-3 cells, head and neck cancer Detroit 562 cells, and bladder cancer SW780 cells). The results are shown in Table 5.

TABLE 5

In vitro activity assay (x50, nM)

| | BxPC3 | Detroit-562 | HAPF-II | SW780 |
|---|---|---|---|---|
| HCLE | 6 | 17.6 | 14.8 | 7.9 |
| HCLG | 5.1 | 13.2 | 10 | 5.2 |
| HCLH | 15.5 | 28.4 | 28.7 | 11.6 |
| HALG | 8.2 | 21.2 | 17.9 | 19.6 |

TABLE 5-continued

| | In vitro activity assay (×50, nM) | | | |
|---|---|---|---|---|
| | BxPC3 | Detroit-562 | HAPF-II | SW780 |
| m2A2 | 11.1 | 19.4 | 15.6 | 11.7 |
| h15H3-HTLC | 8.4 | 305 | 8.9 | 13.8 |

The humanized variant comprising heavy chain variant hvHC and light chain variant hvLG (h2A2 HCLG) was selected for further study.

Figure 8:
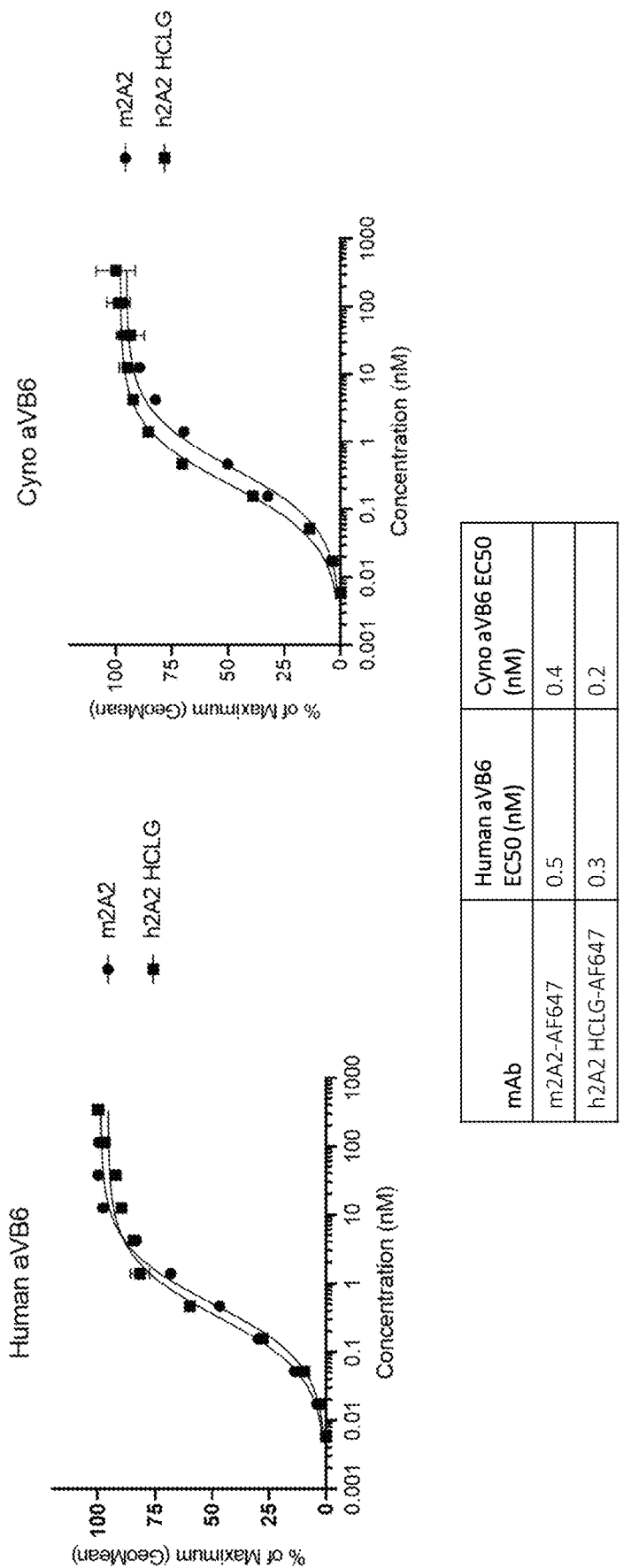
FIG. 8 shows the results of saturation binding studies on 293F cells expressing human and cyno αvβ6 with the h2A2 HCLG humanized antibody and the parental murine antibody (referred to as m2A2).
Figure 9:
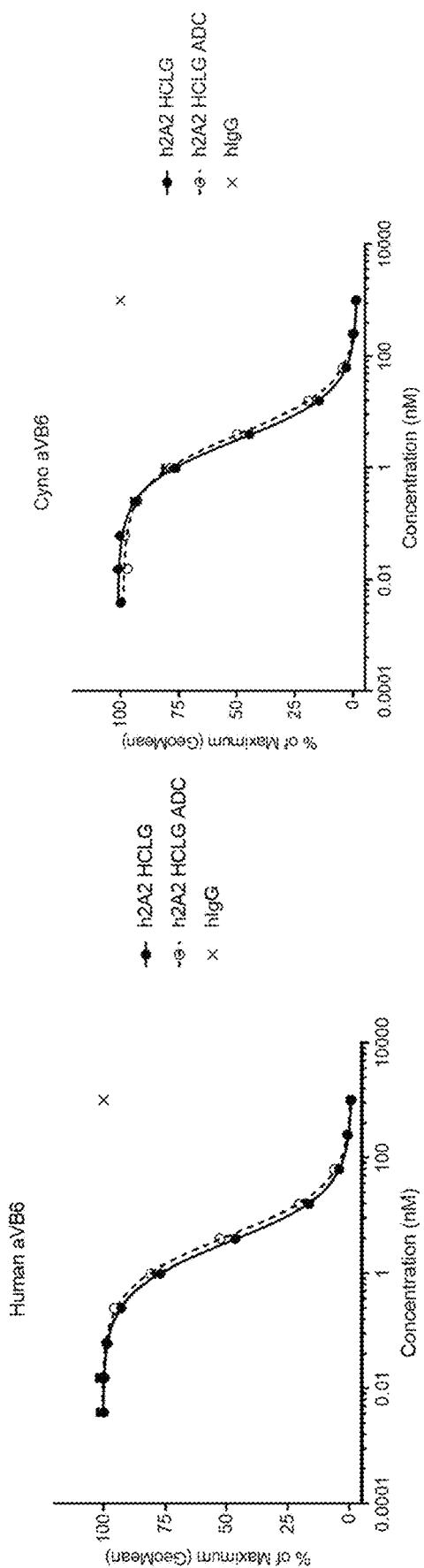
FIG. 9 shows the results of competition binding studies on 293F cells expressing human and cyno αvβ6 with HCLG humanized antibody and ADC.
Figure 10:
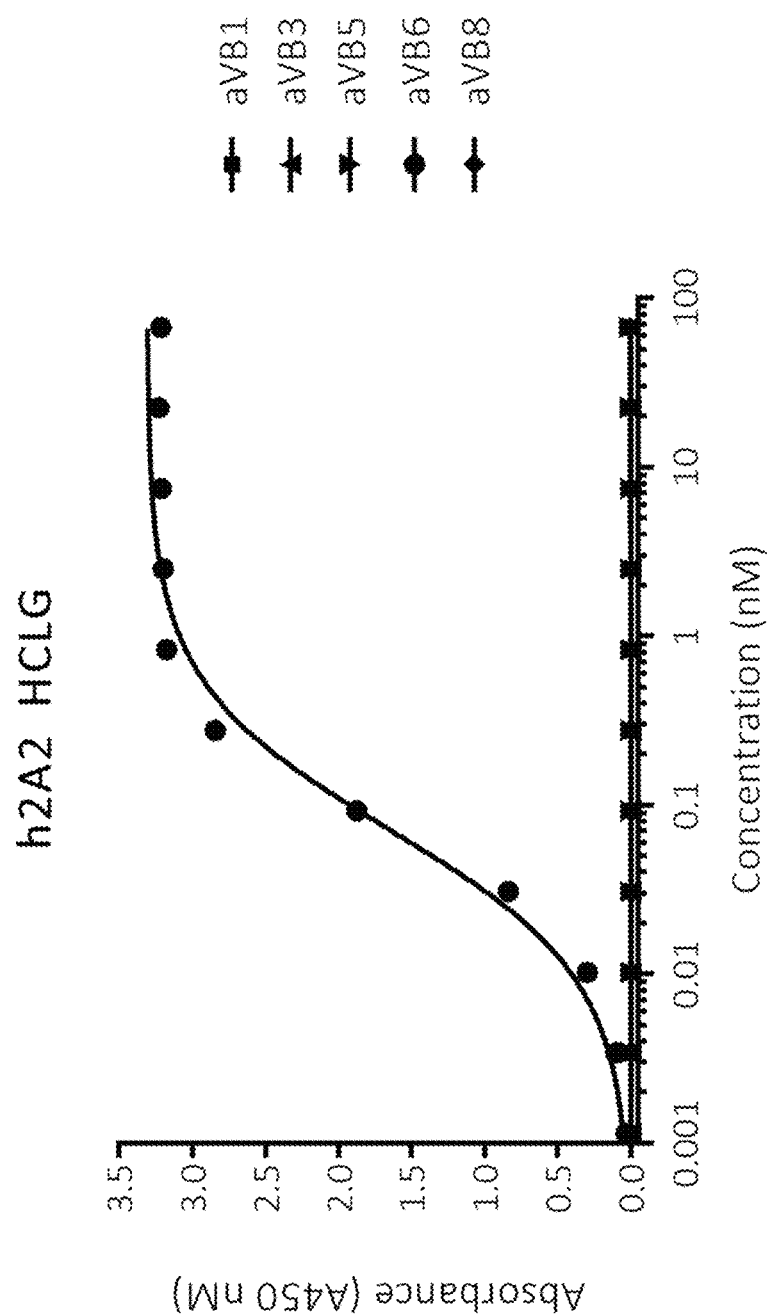
FIG. 10 shows the results of αvβ6 specific binding studies by ELISA to human αvβ1, αvβ3, αvβ5, αvβ6, and αvβ8 with the h2A2 HCLG humanized antibody.

Binding of h2A2 HCLG to both human and cyno αvβ6 was confirmed by saturation binding (FIG. 8) that included the parental murine 2A2 as a reference to demonstrate comparable binding between it and the humanized variant. Binding of h2A2 HCLG to both human and cyno αvβ6 was also confirmed by competition binding against fluorescently labeled murine 2A2 (FIG. 9). This assay also included binding of an ADC prepared with h2A2 HCLG and the SGD-5088 drug-linker by reducing the antibody interchain disulfides and conjugation with eight copies of drug-linker. The conjugation process had no impact on binding to αvβ6 from either human or cyno. Binding specificity of h2A2 HCLG was also confirmed by ELISA in which the antibody bound to recombinant human αvβ6 but not αvβ1, αvβ3, αvβ5, or αvβ8 (FIG. 10).

In Vitro Anticancer Activity of h2A2 ADC

Figure 11:
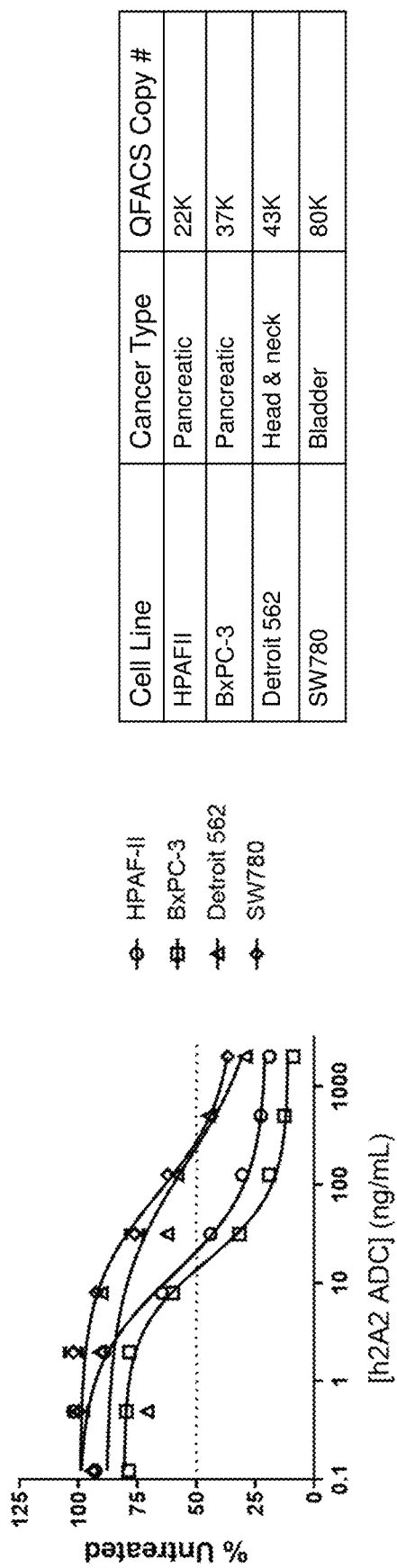
FIG. 11 shows that h2A2 HCLG anti-αvβ6 vcMMAE ADC exhibits in vitro cytotoxicity against αvβ6 expressing cancer cell lines.
Figure 12:
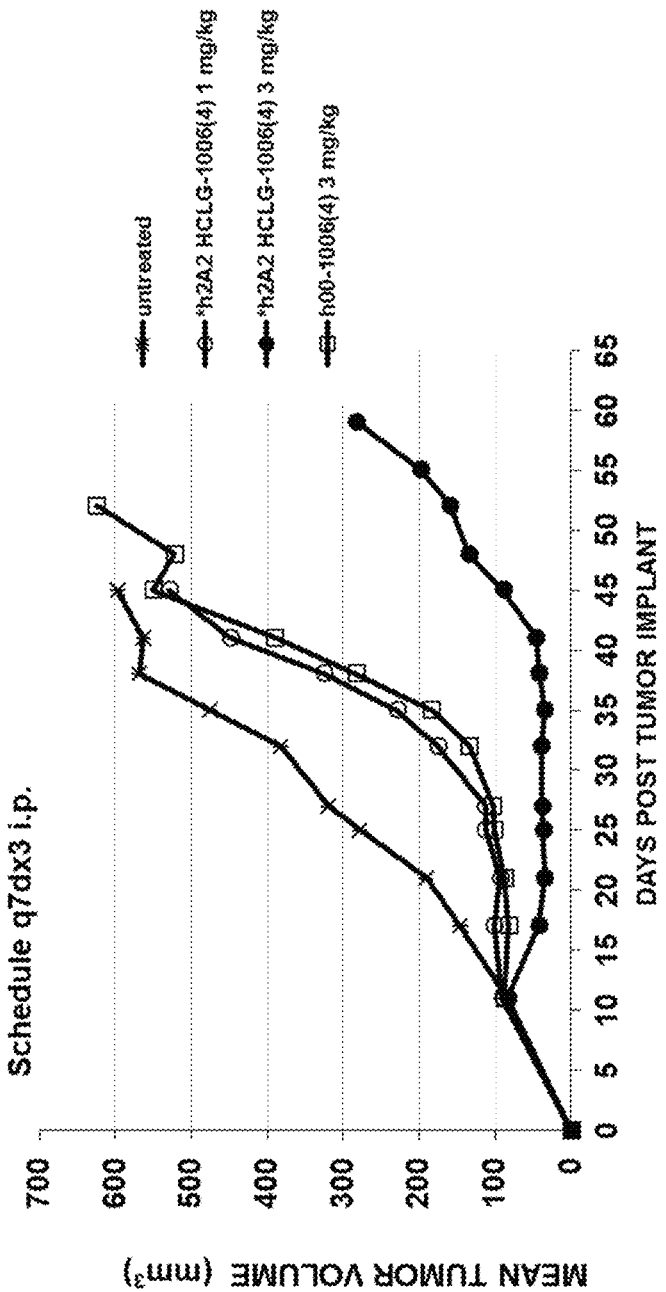
FIG. 12 shows the results of a xenograft study of the Detroit 562 head and neck cancer cell line in nude mice. The dose and schedule are indicated on the figure.
Figure 13:
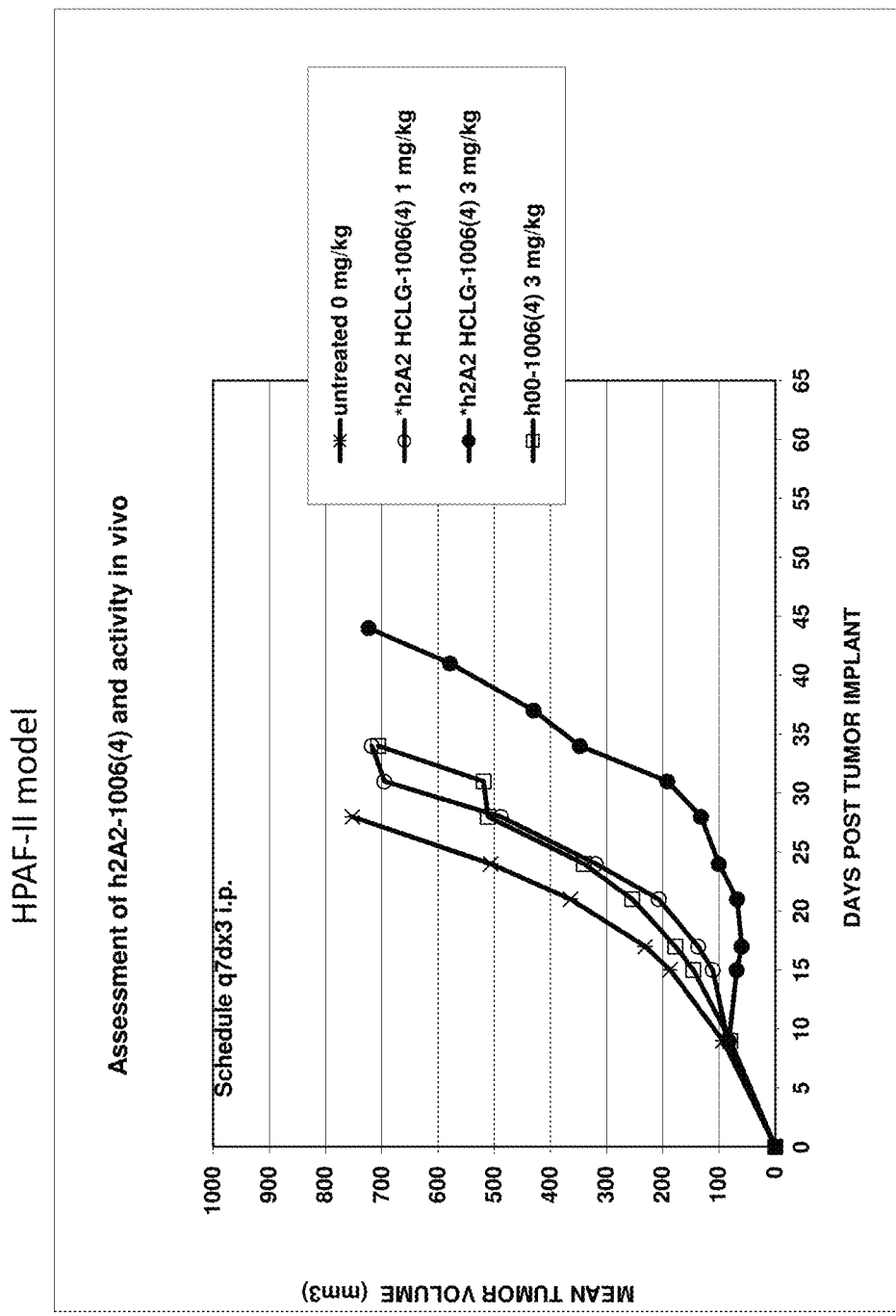
FIG. 13 shows the results of a xenograft study of the HPAFII pancreatic cancer cell line in nude mice. The dose and schedule are indicated on the figure.
Figure 14:
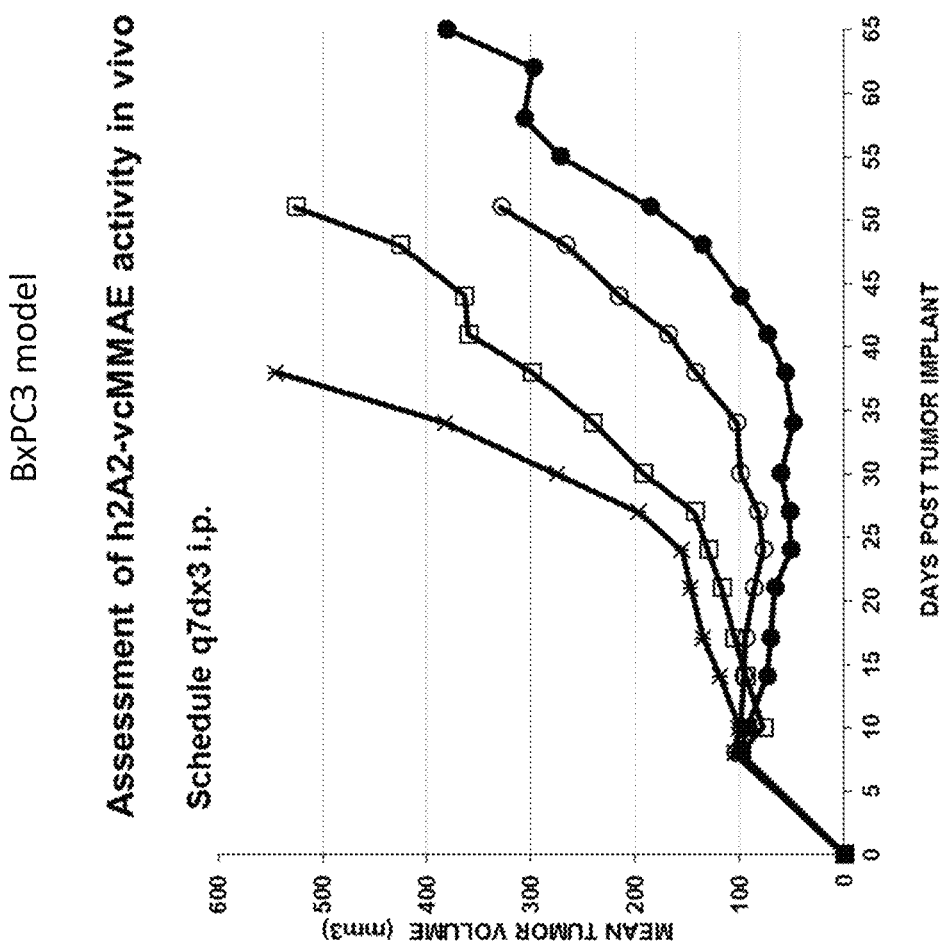
FIG. 14 shows the results of a xenograft study of the BxPC-3 pancreatic cancer cell line in nude mice. The dose and schedule are indicated on the figure.
Figure 15:
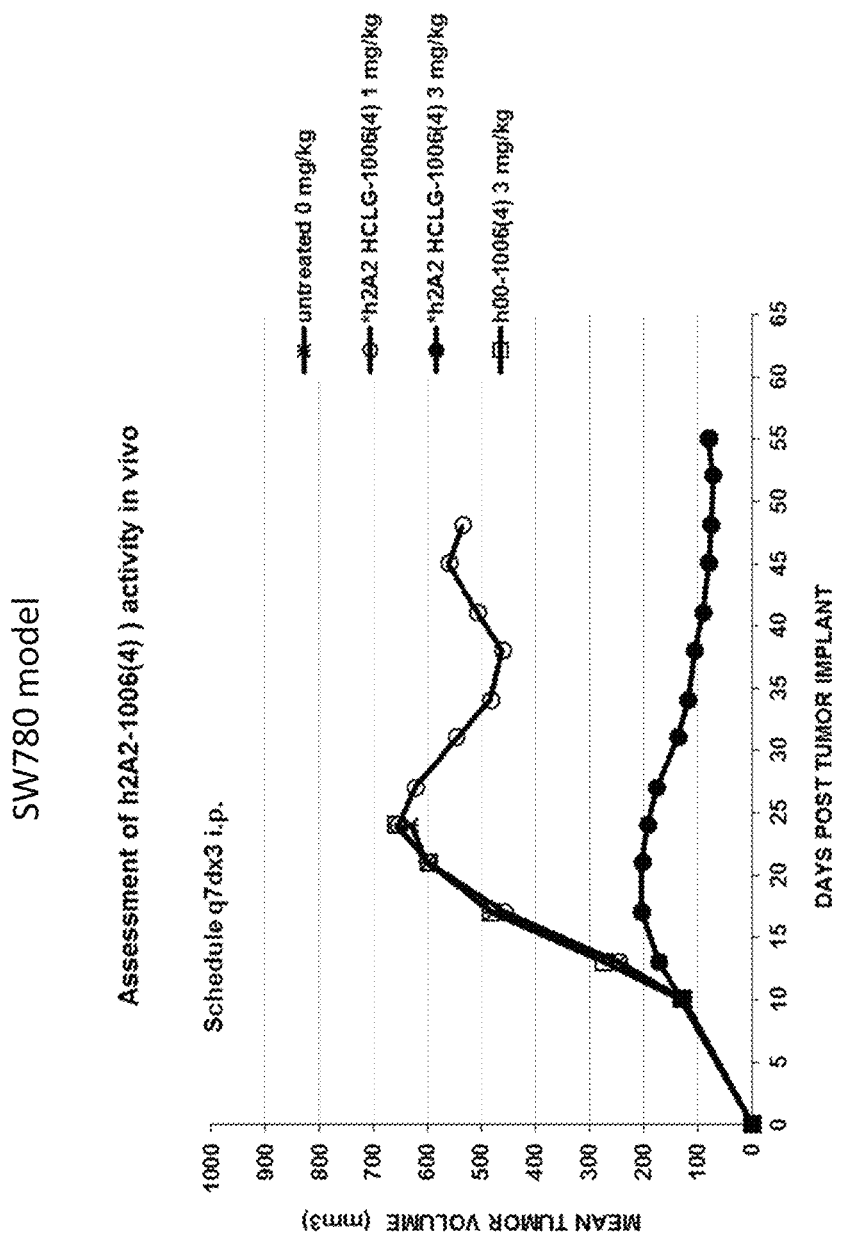
FIG. 15 shows the results of a xenograft study of the SW780 bladder cancer cell line in nude mice. The dose and schedule are indicated on the figure.

In vitro anticancer activity of humanized variant HCLG when conjugated to vcMMAE was measured using cytotoxicity assays in four cell lines expressing αvβ6 at a variety of levels based on quantitative flow cytometry analysis (pancreatic cancer HPAFII and BxPC-3 cells, head and neck cancer Detroit 562 cells, and bladder cancer SW780 cells). FIG. 11 shows that the humanized 2A2 anti-αvβ6 ADC exhibited cell killing behavior in these assays.

In Vivo Anticancer Activity of h2A2 ADCs

Using the same four cell lines tested in vitro, the antitumor activity of humanized 2A2 HCLG antibody conjugated with vcMMAE (average of 4 drugs per antibody) in vivo (Figures. 12-15) was demonstrated. Significant tumor growth delay or tumor regression compared to untreated and non-binding control ADC was observed. h2A2 HCLG-1006 (4) refers to antibody drug conjugates of the HCLG humanized form of the parental murine antibody 2A2 having an average of 4 vcMMAE drug linker molecules per antibody. h00-1006 (4) refers to an antibody drug conjugate of a nonbinding control antibody having an average of 4 vcMMAE drug linker molecules per antibody.

Figure 16:
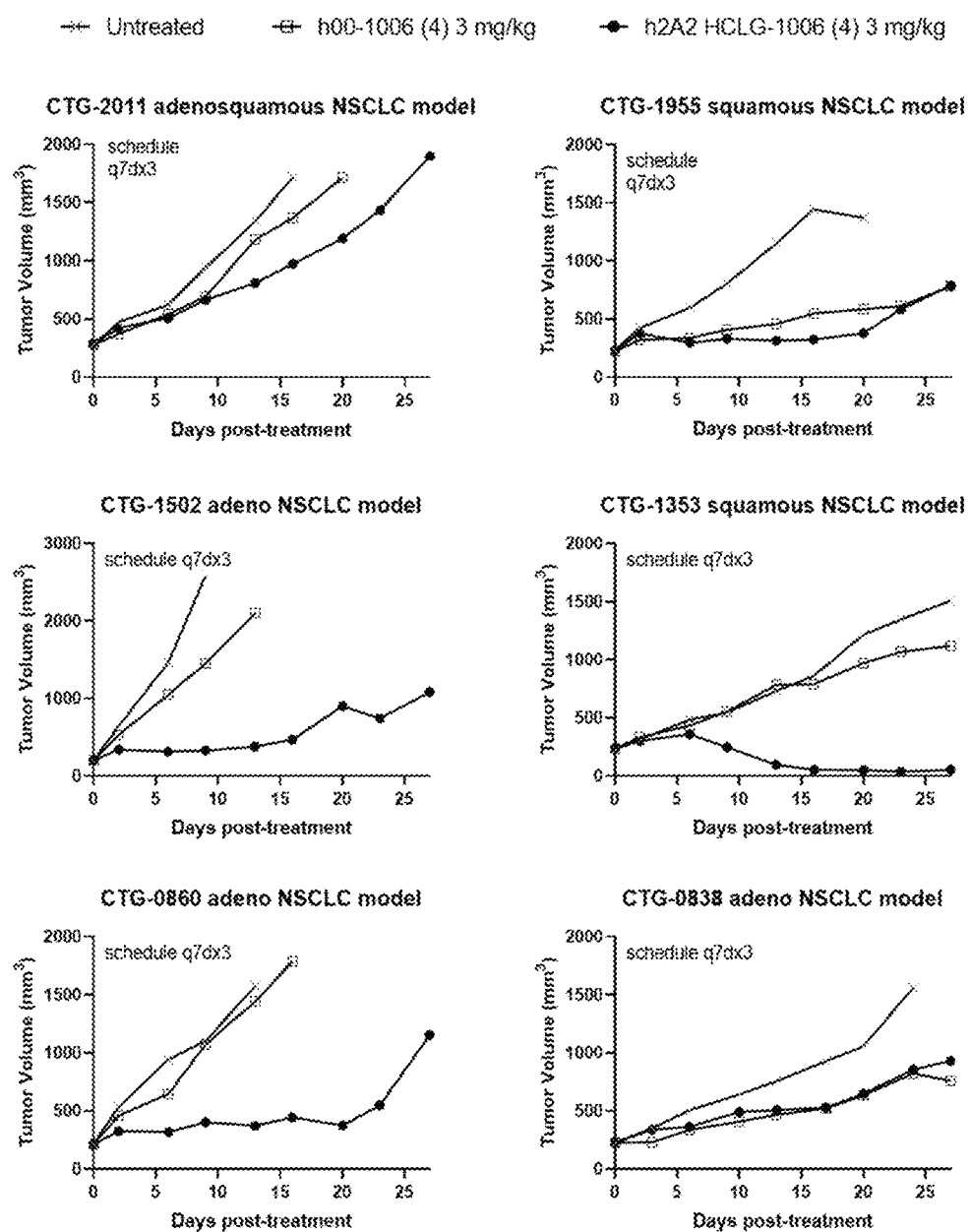
FIG. 16 shows the results of a PDX study in six NSCLC cell lines in nude mice. ADCs were dosed at 3 mg/kg q7dx3.

In PDX models of NSCLC, humanized 2A2 HCLG antibody conjugated with vcMMAE (average of 4 drugs per antibody) also showed anti-tumor activity (FIG. 16). Significant tumor growth delays or tumor regressions compared to untreated and non-binding control ADC were observed. h2A2 HCLG-1006 (4) refers to antibody drug conjugates of the HCLG humanized form of the parental murine antibody 2A2 having an average of 4 vcMMAE drug linker molecules per antibody. h00-1006 (4) refers to an antibody drug conjugate of a nonbinding control antibody having an average of 4 vcMMAE drug linker molecules per antibody.

Figure 17:
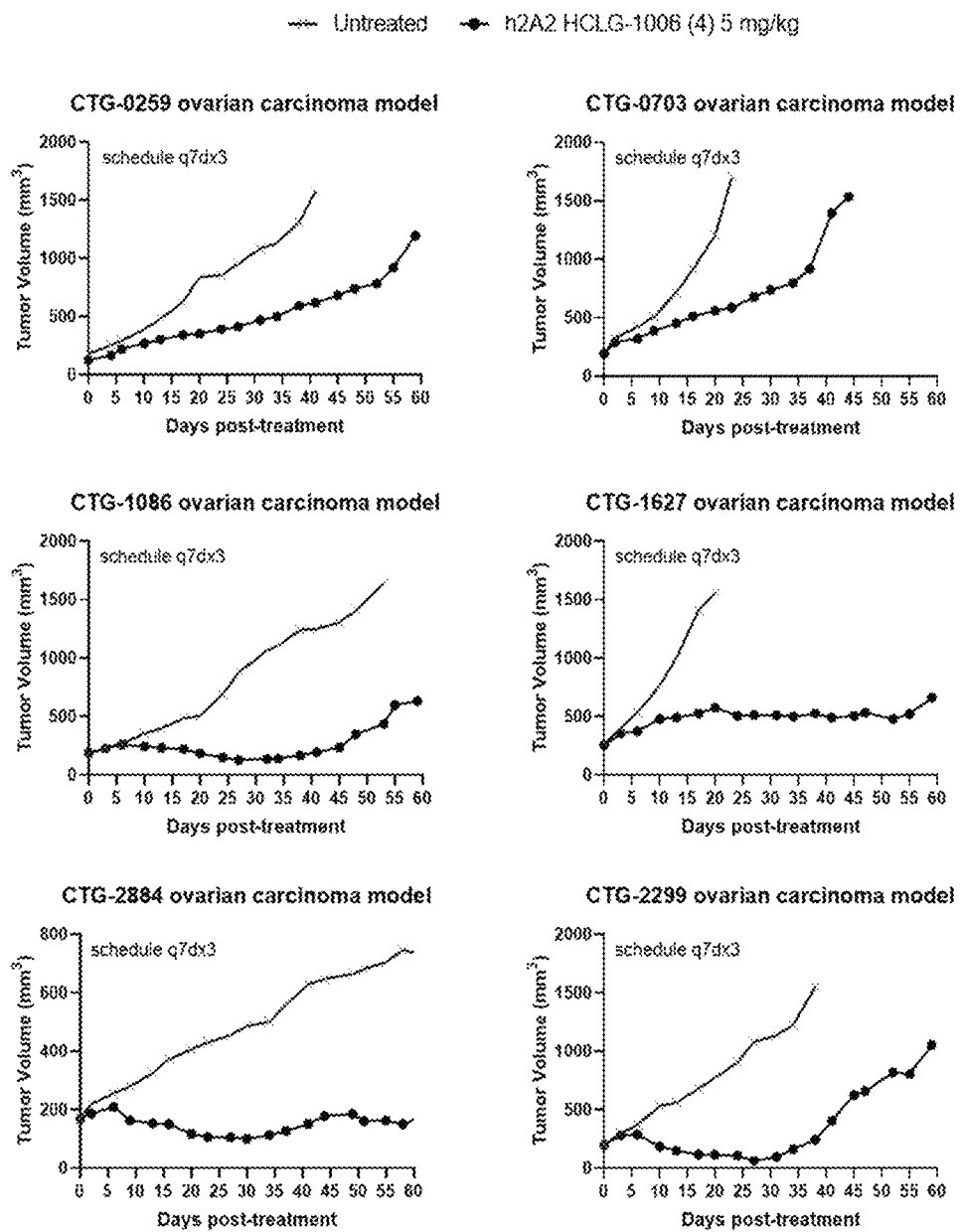
FIG. 17 shows the results of a PDX study in six ovarian carcinoma cell lines in nude mice. ADCs were dosed at 5 mg/kg q7dx3.

In PDX models of ovarian carcinoma, humanized 2A2 HCLG antibody conjugated with vcMMAE (average of 4 drugs per antibody) also showed anti-tumor activity (FIG. 17). Significant tumor growth delays or slight tumor reductions compared to untreated tumors were observed. h2A2 HCLG-1006 (4) refers to antibody drug conjugates of the HCLG humanized form of the parental murine antibody 2A2 having an average of 4 vcMMAE drug linker molecules per antibody.

Figure 18:
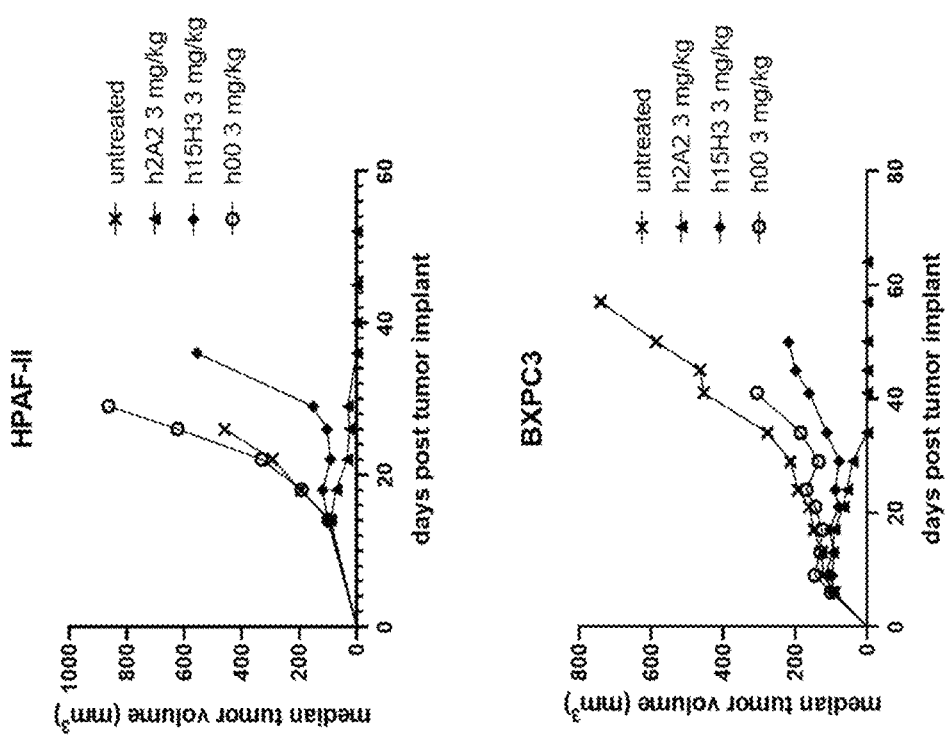
FIG. 18 shows the results of a comparison between h2A2 HCLG and h15H3 in two cell line xenograft models. ADCs were dosed once at 3 mg/kg.

The antitumor activity of h2A2 HCLG was compared with h15H3 when conjugated with drug-linker VIa (n=12, $R^{PR}$=H, $R^{21}$=CH$_3$) with a DAR of 8. The study protocol was the same as described above for cell line-derived xenograft models, using the HPAFII and BxPC3 cell lines. Animals were dosed once at 3 mg/kg with either h2A2 HCLG, h15H3, or non-targeted control (h00) ADCs (FIG. 18). In both models the h2A2 HCLG ADCs exhibited durable regressions of the implanted tumors, while the h15H3 ADCs exhibited growth delay.

SEQUENCES

```
SEQ ID NO: 1 - m2A2 vH
EFQLQQSGPELVKPGASVKISCKASGYSFTDYNVNWVKQSNGKSLEWIGVINPKYGTTR
YNQKFKGKATLTVDKPSSTAYMQLNSLTSEDSAVYYCTRGLNAWDYWGQGASVTVSS

SEQ ID NO: 2 - mIGHV1-39 (closest murine germline V-gene)
EFQLQQSGPELVKPGASVKISCKASGYSFTDYNMNWVKQSNGKSLEWIGVINPNYGTTS
YNQKFKGKATLTVDQSSSTAYMQLNSLTSEDSAVYYCAR SEQ ID NO: 3 - hIGHV1-46/HJ4
QVQLVQSGAEVKKPGASVKVSCKASGYTFTSYYMHWVRQAPGQGLEWMGIINPSGGS
TSYAQKFQGRVTMTRDTSTSTVYMELSSLRSEDTAVYYCARYFDYWGQGTLVTVSS SEQ ID NO: 4 - h2A2 vHA
QFQLVQSGAEVKKPGASVKVSCKASGYSFTDYNVNWVRQAPGQGLEWMGVINPKYGT
TRYNQKFKGRVTMTRDTSTSTVYMELSSLRSEDTAVYYCTRGLNAWDYWGQGTLVTV
SS SEQ ID NO: 5 - h2A2 vHB
QFQLVQSGAEVKKPGASVKVSCKASGYSFTDYNVNWVRQAPGQGLEWMGVINPKYGT
TRYNQKFKGRVTMTRDTPTSTVYMELSSLRSEDTAVYYCTRGLNAWDYWGQGTLVTV
SS SEQ ID NO: 6 - h2A2 vHC
QFQLVQSGAEVKKPGASVKVSCKASGYSFTDYNVNWVRQAPGQGLEWIGVINPKYGT
TRYNQKFKGRATLTVDKSTSTAYMELSSLRSEDTAVYYCTRGLNAWDYWGQGTLVTV
SS
```

-continued

SEQUENCES

SEQ ID NO: 7 - h2A2 vHD
QFQLVQSGAEVKKPGASVKVSCKASGYSFT<u>DYNVN</u>WVRQAPGQGLEWIG<u>VINPKYGT
TRYNQKFK</u>GRATLTVDKPTSTAYMELSSLRSEDTAVYYCT<u>RGLNAWDY</u>WGQGTLVTV
SS

SEQ ID NO: 8 - m2A2 vL
DIQMTQSPASLSASVGETVTITC<u>GASENIYGALN</u>WYQRKQGKSPQLLIY<u>GATNLAD</u>GMS
SRFSGSGSGRQYSFKISSLHPDDVATYYC<u>QNVLTTPYT</u>FGGGTKLEIK

SEQ ID NO: 9 - mIGKV12-89 (closest murine germline V-gene)
DIQMTQSPASLSASVGETVTITC<u>GASENIYGALN</u>WYQRKQGKSPQLLIY<u>GATNLAD</u>GMS
SRFSGSGSGRQYSLKISSLHPDDVATYYCQNVLSTP SEQ ID NO: 10 - hIGKV1D-33/KJ2
DIQMTQSPSSLSASVGDRVTITC<u>QASQDISNYLN</u>WYQQKPGKAPKLLIY<u>DASNLET</u>GVPS
RFSGSGSGTDFTFTISSLQPEDIATYYCQQYDNLP YTFGQGTKLEIK SEQ ID NO: 11 - h2A2 vLA
DIQMTQSPSSLSASVGDRVTITC<u>GASENIYGALN</u>WYQQKPGKAPKLLIY<u>GATNLAD</u>GVP
SRFSGSGSGTDFTFTISSLQPEDIATYYC<u>QNVLTTPYT</u>FGQGTKLEIK SEQ ID NO: 12 - h2A2 vLB
DIQMTQSPSSLSASVGDRVTITC<u>GASENIYGALN</u>WYQQKPGKAPKLLIY<u>GATNLAD</u>GVP
SRFSGSGSGRDYTFTISSLQPEDIATYYC<u>QNVLTTPYT</u>FGQGTKLEIK SEQ ID NO: 13 - h2A2 vLC
DIQMTQSPSSLSASVGDRVTITC<u>GASENIYGALN</u>WYQQKPGKAPKLLIY<u>GATNLAT</u>GVP
SRFSGSGSGRDYTFTISSLQPEDIATYYC<u>QNVLTTPYT</u>FGQGTKLEIK SEQ ID NO: 14 - h2A2 vLD
DIQMTQSPSSLSASVGDRVTITC<u>GASENIYGALN</u>WYQQKPGKAPKLLIY<u>GATNLAD</u>GVP
SRFSGSGSGTDYTFTISSLQPEDIATYYC<u>QNVLTTPYT</u>FGQGTKLEIK SEQ ID NO: 15 - h2A2 vLE
DIQMTQSPSSLSASVGDRVTITC<u>QASENIYGALN</u>WYQQKPGKAPKLLIY<u>GATNLAD</u>GVP
SRFSGSGSGRDYTFTISSLQPEDIATYYC<u>QNVLTTPYT</u>FGQGTKLEIK SEQ ID NO: 16 - h2A2 vLF
DIQMTQSPSSLSASVGDRVTITC<u>QASENIYGALN</u>WYQQKPGKAPKLLIY<u>GATNLAT</u>GVP
SRFSGSGSGTDYTFTISSLQPEDIATYYC<u>QNVLTTPYT</u>FGQGTKLEIK SEQ ID NO: 17 - h2A2 vLG
DIQMTQSPSSLSASVGDRVTITC<u>GASENIYGALN</u>WYQQKPGKAPKLLIY<u>GATNLED</u>GVP
SRFSGSGSGRDYTFTISSLQPEDIATYYC<u>QNVLTTPYT</u>FGQGTKLEIK SEQ ID NO: 18 - h2A2 vLH
DIQMTQSPSSLSASVGDRVTITC<u>GASENIYGALN</u>WYQQKPGKAPKLLIY<u>GATNLAD</u>GVP
SRFSGSGSGRDFTFTISSLQPEDIATYYC<u>QNVLTTPYT</u>FGQGTKLEIK SEQ ID NO: 19 - h2A2 HA heavy chain
QFQLVQSGAEVKKPGASVKVSCKASGYSFT<u>DYNVN</u>WVRQAPGQGLEWMG<u>VINPKYGT
TRYNQKFK</u>GRVTMTRDTSTSTVYMELSSLRSEDTAVYYCT<u>RGLNAWDY</u>WGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFFLYSKLTV
DKSRWQQGNVFSCSVMHEALHNHYTQKSLSLSPGK SEQ ID NO: 20 - h2A2 HB heavy chain
QFQLVQSGAEVKKPGASVKVSCKASGYSFT<u>DYNVN</u>WVRQAPGQGLEWMG<u>VINPKYGT
TRYNQKFK</u>GRVTMTRDTPTSTVYMELSSLRSEDTAVYYCT<u>RGLNAWDY</u>WGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP
SRDELTKNQVSLTCLVKGFYPSDIAVEWESNGQPENNYKTTPPVLDSDGSFFLYSKLTV
DKSRWQQGNVFSCSVMHEALHNHYTQKSLSLSPGK SEQ ID NO: 21 - h2A2 HC heavy chain
QFQLVQSGAEVKKPGASVKVSCKASGYSFT<u>DYNVN</u>WVRQAPGQGLEWIG<u>VINPKYGT
TRYNQKFK</u>GRATLTVDKSTSTAYMELSSLRSEDTAVYYCT<u>RGLNAWDY</u>WGQGTLVTV
SSASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPP

| SEQUENCES |
|---|
| SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK<br><br>SEQ ID NO: 22 - h2A2 HD heavy chain<br>QFQLVQSGAEVKKPGASVKVSCKASGYSFT<u>DYNVN</u>WVRQAPGQGLEWIG<u>VINPKYGT</u><br><u>TRYNQKFKG</u>RATLTVDKPTSTAYMELSSLRSEDTAVYYCTR<u>GLNAWDY</u>WGQGTLVTV<br>SSASTKGPSVFPLAPSSKSTSGGTAALGCLVKDYFPEPVTVSWNSGALTSGVHTFPAVLQ<br>SSGLYSLSSVVTVPSSSLGTQTYICNVNHKPSNTKVDKKVEPKSCDKTHTCPPCPAPELL<br>GGPSVFLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVYTLPP<br>SRDELTKNQVSLTCLVKGFYPSDIAVEWESNGQPENNYKTTPPVLDSDGSFFLYSKLTV<br>DKSRWQQGNVFSCSVMHEALHNHYTQKSLSLSPGK<br><br>SEQ ID NO: 23 - h2A2 LA light chain<br>DIQMTQSPSSLSASVGDRVTITC<u>GASENIYGALN</u>WYQQKPGKAPKLLIY<u>GATNLAD</u>GVP<br>SRFSGSGSGTDFTFTISSLQPEDIATYYC<u>QNVLTTPYT</u>FGQGTKLEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC<br><br>SEQ ID NO: 24 - h2A2 LB light chain<br>DIQMTQSPSSLSASVGDRVTITC<u>GASENIYGALN</u>WYQQKPGKAPKLLIY<u>GATNLAD</u>GVP<br>SRFSGSGSGRDYTFTISSLQPEDIATYYC<u>QNVLTTPYT</u>FGQGTKLEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC<br><br>SEQ ID NO: 25 - h2A2 LC light chain<br>DIQMTQSPSSLSASVGDRVTITC<u>GASENIYGALN</u>WYQQKPGKAPKLLIY<u>GATNLAT</u>GVP<br>SRFSGSGSGRDYTFTISSLQPEDIATYYC<u>QNVLTTPYT</u>FGQGTKLEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC<br><br>SEQ ID NO: 26 - h2A2 LD light chain<br>DIQMTQSPSSLSASVGDRVTITC<u>GASENIYGALN</u>WYQQKPGKAPKLLIY<u>GATNLAD</u>GVP<br>SRFSGSGSGTDYTFTISSLQPEDIATYYC<u>QNVLTTPYT</u>FGQGTKLEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC<br><br>SEQ ID NO: 27 - h2A2 LE light chain<br>DIQMTQSPSSLSASVGDRVTITC<u>QASENIYGALN</u>WYQQKPGKAPKLLIY<u>GATNLAD</u>GVP<br>SRFSGSGSGRDYTFTISSLQPEDIATYYC<u>QNVLTTPYT</u>FGQGTKLEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC<br><br>SEQ ID NO: 28 - h2A2 LF light chain<br>DIQMTQSPSSLSASVGDRVTITC<u>QASENIYGALN</u>WYQQKPGKAPKLLIY<u>GATNLAT</u>GVP<br>SRFSGSGSGTDYTFTISSLQPEDIATYYC<u>QNVLTTPYT</u>FGQGTKLEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC<br><br>SEQ ID NO: 29 - h2A2 LG light chain<br>DIQMTQSPSSLSASVGDRVTITC<u>GASENIYGALN</u>WYQQKPGKAPKLLIY<u>GATNLED</u>GVP<br>SRFSGSGSGRDYTFTISSLQPEDIATYYC<u>QNVLTTPYT</u>FGQGTKLEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC<br><br>SEQ ID NO: 30 - h2A2 LH light chain<br>DIQMTQSPSSLSASVGDRVTITC<u>GASENIYGALN</u>WYQQKPGKAPKLLIY<u>GATNLAD</u>GVP<br>SRFSGSGSGRDFTFTISSLQPEDIATYYC<u>QNVLTTPYT</u>FGQGTKLEIKRTVAAPSVFIFPPS<br>DEQLKSGTASVVCLLNNFYPREAKVQWKVDNALQSGNSQESVTEQDSKDSTYSLSSTL<br>TLSKADYEKHKVYACEVTHQGLSSPVTKSFNRGEC<br><br>SEQ ID NO: 31 - HA, HB, HC, HD CDR1, KABAT<br>DYNVN<br><br>SEQ ID NO: 32 - HA, HB, HC, HD CDR2, KABAT<br>VINPKYGTTRYNQKFKG<br><br>SEQ ID NO: 33 - HA, HB, HC, HD CDR3, KABAT<br>GLNAWDY<br><br>SEQ ID NO: 34 - HA, HB, HC, HD CDR1, IMGT<br>GYSFTDYN<br><br>SEQ ID NO: 35 - HA, HB, HC, HD CDR2, IMGT<br>INPKYGTT |

SEQUENCES

SEQ ID NO: 36 - HA, HB, HC, HD CDR3, IMGT
TRGLNAWDY

SEQ ID NO: 37 - LA, LB, LC, LD, LG, LH CDR1, KABAT
GASENIYGALN

SEQ ID NO: 38 - LA, LB, LD, LE, LH CDR2, KABAT
GATNLAD

SEQ ID NO: 39 - LA, LB, LC, LD, LE, LF, LG, LH CDR3, KABAT
QNVLTTPYT

SEQ ID NO: 40 - LE, LF CDR1, KABAT
QASENIYGALN

SEQ ID NO: 41 - LC, LF CDR2, KABAT
GATNLAT

SEQ ID NO: 42 - LG CDR2, KABAT
GATNLED

SEQ ID NO: 43 - LA, LB, LC, LD, LE, LF, LG, LH CDR1, IMGT
ENIYGA

SEQ ID NO: 44 - LA, LB, LC, LD, LE, LF, LG, LH CDR2, IMGT
GAT

SEQ ID NO: 45 - LA, LB, LC, LD, LE, LF, LG, LH CDR3, IMGT
QNVLTTPYT

The invention claimed is:

1. An isolated anti-αvβ6 antibody, or antigen-binding fragment thereof, comprising a heavy chain variable region and a light chain variable region, wherein the heavy chain variable region comprises:
   (i) a CDR-H1 comprising the amino acid sequence of SEQ ID NO:31;
   (ii) a CDR-H2 comprising the amino acid sequence of SEQ ID NO:32; and
   (iii) a CDR-H3 comprising the amino acid sequence of SEQ ID NO:33; and
wherein the light chain variable region comprises:
   (i) a CDR-L1 comprising the amino acid sequence of SEQ ID NO:37;
   (ii) a CDR-L2 comprising the amino acid sequence of SEQ ID NO:42; and
   (iii) a CDR-L3 comprising the amino acid sequence of SEQ ID NO:39
wherein the CDRs are determined by Kabat.

2. An isolated anti-αvβ6 antibody, or antigen-binding fragment thereof, comprising a heavy chain variable region and a light chain variable region, wherein the heavy chain variable region comprises:
   (i) a CDR-H1 comprising the amino acid sequence of SEQ ID NO:34;
   (ii) a CDR-H2 comprising the amino acid sequence of SEQ ID NO:35; and
   (iii) a CDR-H3 comprising the amino acid sequence of SEQ ID NO:36; and
wherein the light chain variable region comprises:
   (i) a CDR-L1 comprising the amino acid sequence of SEQ ID NO:43;
   (ii) a CDR-L2 comprising the amino acid sequence of SEQ ID NO:44; and
   (iii) a CDR-L3 comprising the amino acid sequence of SEQ ID NO:45
wherein the CDRs are determined by IMGT.

3. The antibody or antigen-binding fragment of claim 1 or claim 2, wherein the antibody is humanized.

4. The antibody or antigen-binding fragment of claim 1 or claim 2, wherein the heavy chain variable region comprises an amino acid sequence having at least 90% sequence identity to the amino acid sequence of SEQ ID NO: 6 and the light chain variable region comprises an amino acid sequence having at least 90% sequence identity to the amino acid sequence of SEQ ID NO: 17.

5. The antibody or antigen-binding fragment of claim 1 or claim 2, wherein the heavy chain variable region comprises an amino acid sequence having at least 95% sequence identity to the amino acid sequence of SEQ ID NO: 6 and the light chain variable region comprises an amino acid sequence having at least 95% sequence identity to the amino acid sequence of SEQ ID NO: 17.

6. The antibody or antigen-binding fragment of claim 1 or claim 2, wherein the heavy chain variable region comprises an amino acid sequence having at least 99% sequence identity to the amino acid sequence of SEQ ID NO: 6 and the light chain variable region comprises an amino acid sequence having at least 99% sequence identity to the amino acid sequence of SEQ ID NO: 17.

7. The antibody or antigen-binding fragment of claim 1 or claim 2, wherein the heavy chain variable region comprises the amino acid sequence of SEQ ID NO: 6 and the light chain variable region comprises the amino acid sequence of SEQ ID NO:17.

8. The antibody or antigen-binding fragment of claim 3, wherein H2 is occupied by F, H28 is occupied by S, H48 is occupied by I, H67 is occupied by A, H69 is occupied by L, H71 is occupied by V, H73 is occupied by K, H78 is occupied by A, H93 is occupied by T, L69 is occupied by R, and L71 is occupied by Y, and wherein the numbering is via the Kabat numbering system.

9. The antibody or antigen-binding fragment of claim 1 or claim 2, wherein the antibody or antigen-binding fragment comprises a heavy chain and a light chain, wherein the heavy chain has an amino acid sequence comprising SEQ ID NO:21 and the light chain has an amino acid sequence comprising SEQ ID NO:29.

10. The antibody or antigen-binding fragment of claim 1 or claim 2, wherein the antibody or antigen-binding fragment is an antigen-binding fragment, and wherein the antigen-binding fragment is selected from the group consisting of Fab, Fab', F(ab')$_2$, Fab'-SH, Fv, diabody, linear antibody, and single-chain antibody fragment.

11. The antibody or antigen-binding fragment of claim 1 or claim 2, wherein the heavy chain variable region of the antibody is fused to a heavy chain constant region and the light chain variable region is fused to a light chain constant region.

12. The antibody or antigen-binding fragment of claim 11, wherein the heavy chain constant region is of the IgG1 isotype.

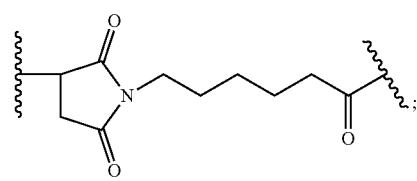

Formula I

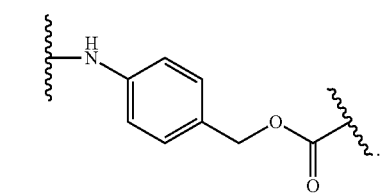

Formula II

21. The antibody-drug conjugate of claim 14, wherein the linker is attached to monomethyl auristatin E and has the structure:

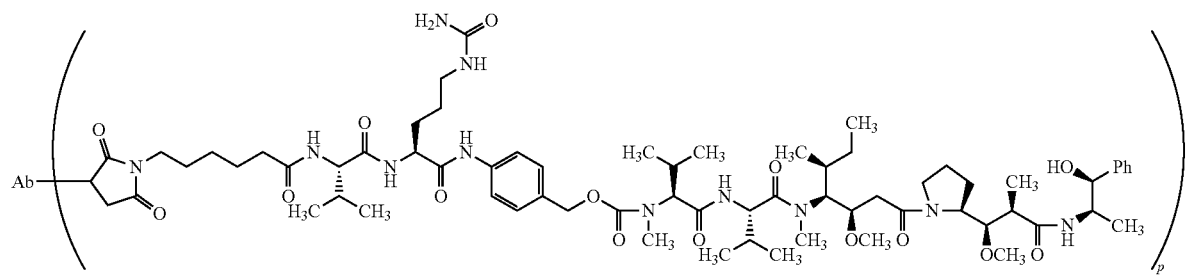

13. An antibody-drug conjugate comprising the antibody or antigen-binding fragment of claim 1 or claim 2 conjugated to a cytotoxic or cytostatic agent.

14. The antibody-drug conjugate of claim 13, wherein the antibody or antigen-binding fragment is conjugated to the cytotoxic or cytostatic agent via a linker.

15. The antibody-drug conjugate of claim 13, wherein the cytotoxic or cytostatic agent is a monomethyl auristatin.

16. The antibody-drug conjugate of claim 15, wherein the monomethyl auristatin is monomethyl auristatin E (MMAE).

17. The antibody-drug conjugate of claim 16, wherein the antibody or antigen binding fragment thereof is conjugated to MMAE via an enzyme-cleavable linker unit.

18. The antibody-drug conjugate of claim 17, wherein the enzyme-cleavable linker unit comprises a Val-Cit linker.

19. The antibody-drug conjugate of claim 18, wherein the antibody or antigen binding fragment thereof is conjugated to MMAE via a linker unit that has the formula: -A$_a$-W$_w$—Y$_y$—; wherein -A- is a stretcher unit, a is 0 or 1; —W— is an amino acid unit, w is an integer ranging from 0 to 12; and —Y— is a spacer unit, y is 0, 1, or 2.

20. The antibody-drug conjugate of claim 19, wherein the stretcher unit has the structure of Formula I below; wherein the amino acid unit is Val-Cit; and wherein the spacer unit is a p-aminobenzyl alcohol (PAB) group having the structure of Formula II below;

wherein Ab is the antibody or antigen-binding fragment and p denotes a number from 1 to 16.

22. The antibody-drug conjugate of claim 21, wherein the average value of p in a population of the antibody-drug conjugate is about 4.

23. A method of treating cancer in a subject, the method comprising administering to the subject the antibody-drug conjugate of claim 13.

24. The method of claim 23, wherein the cancer is selected from the group consisting of non-small cell lung cancer (NSCLC), head and neck cancer, esophageal cancer, breast cancer, ovarian cancer, bladder cancer, skin cancer (SCC), ovarian cancer, cervical cancer, gastric cancer, and pancreatic cancer.

25. The method of claim 23, wherein the cancer is non-small cell lung cancer.

26. The method of claim 23, wherein the cancer is head and neck cancer.

27. The method of claim 23, wherein the antibody or antigen-binding fragment or antibody-drug conjugate is in a pharmaceutical composition comprising the antibody-drug conjugate and a pharmaceutically acceptable carrier.

28. The method of claim 23, wherein the subject is a human.

29. A pharmaceutical composition comprising the antibody-drug conjugate of claim 13 and one or more agents selected from the group consisting of a physiologically acceptable carrier, a diluent, and an excipient.

30. The method of claim 23, wherein the antibody-drug conjugate is administered in combination with radiation or a chemotherapeutic agent.

31. An antibody-drug conjugate comprising an anti-αvβ6 antibody conjugated to vcMMAE, wherein the antibody has a heavy chain variable region comprising the amino acid sequence of SEQ ID NO: 6 and a light chain variable region comprising the amino acid sequence of SEQ ID NO: 17, and wherein the antibody-drug conjugate has the structure:

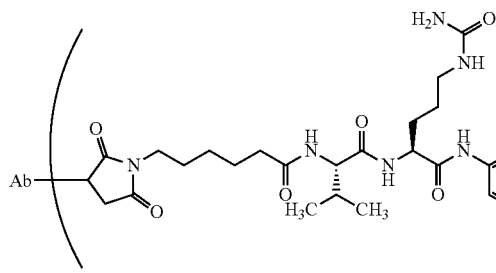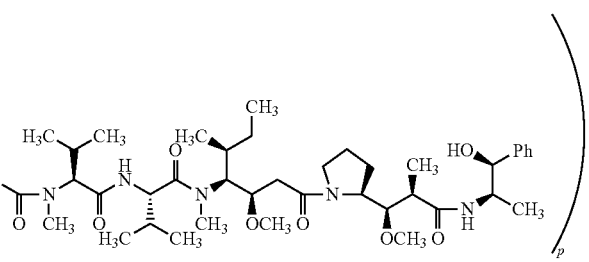

wherein Ab is the antibody and p denotes a number from 1 to 16.

32. An isolated anti-αvβ6 antibody, or antigen-binding fragment thereof, comprising a heavy chain variable region and a light chain variable region, wherein the heavy chain variable region comprises the amino acid sequence of SEQ ID NO: 6 and the light chain variable region comprises the amino acid sequence of SEQ ID NO:17, and wherein the heavy chain variable region of the antibody is fused to a heavy chain constant region and the light chain variable region is fused to a light chain constant region.

33. The antibody or antigen-binding fragment of claim 32, wherein the heavy chain constant region is of the IgG1 isotype.

34. An antibody-drug conjugate comprising an anti-αvβ6 antibody, or antigen-binding fragment thereof, comprising a heavy chain variable region and a light chain variable region, wherein the heavy chain variable region comprises the amino acid sequence of SEQ ID NO: 6 and the light chain variable region comprises the amino acid sequence of SEQ ID NO:17, wherein the antibody or antigen-binding fragment is conjugated to a cytotoxic or cytostatic agent.

35. The antibody-drug conjugate of claim 21, wherein the average value of p in a population of the antibody-drug conjugates is about 2 to about 5.

36. The antibody-drug conjugate of claim 31, wherein the average value of p in a population of the antibody-drug conjugates is about 2 to about 5.

37. The antibody-drug conjugate of claim 31, wherein the average value of p in a population of the antibody-drug conjugates is about 4.

38. The antibody-drug conjugate of claim 34, wherein the antibody or antigen-binding fragment is conjugated to the cytotoxic or cytostatic agent via a linker.

39. The antibody-drug conjugate of claim 34, wherein the cytotoxic or cytostatic agent is a monomethyl auristatin.

40. The antibody-drug conjugate of claim 39, wherein the monomethyl auristatin is monomethyl auristatin E (MMAE).

41. The antibody-drug conjugate of claim 40, wherein the antibody or antigen binding fragment thereof is conjugated to MMAE via an enzyme-cleavable linker unit.

42. The antibody-drug conjugate of claim 41, wherein the enzyme-cleavable linker unit comprises a Val-Cit linker.

43. The antibody-drug conjugate of claim 42, wherein the antibody or antigen binding fragment thereof is conjugated to MMAE via a linker unit that has the formula: -$A_a$-$W_w$—$Y_y$—; wherein -A- is a stretcher unit, a is 0 or 1; —W— is an amino acid unit, w is an integer ranging from 0 to 12; and —Y— is a spacer unit, y is 0, 1, or 2.

44. The antibody-drug conjugate of claim 43, wherein the stretcher unit has the structure of Formula I below; wherein the amino acid unit is Val-Cit; and wherein the spacer unit is a p-aminobenzyl alcohol (PAB) group having the structure of Formula II below;

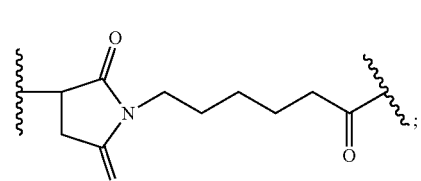

Formula I

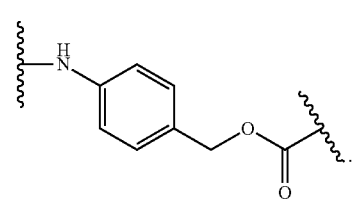

Formula II

45. An antibody-drug conjugate comprising an anti-αvβ6 antibody comprising a heavy chain and a light chain, wherein the heavy chain has an amino acid sequence comprising SEQ ID NO:21 and the light chain has an amino acid sequence comprising SEQ ID NO:29, wherein the antibody is conjugated to a cytotoxic or cytostatic agent.

46. The antibody-drug conjugate of claim 45, wherein the antibody is conjugated to the cytotoxic or cytostatic agent via a linker.

47. The antibody-drug conjugate of claim 45, wherein the cytotoxic or cytostatic agent is a monomethyl auristatin.

48. The antibody-drug conjugate of claim 47, wherein the monomethyl auristatin is monomethyl auristatin E (MMAE).

49. The antibody-drug conjugate of claim 48, wherein the antibody is conjugated to MMAE via an enzyme-cleavable linker unit.

50. The antibody-drug conjugate of claim 49, wherein the enzyme-cleavable linker unit comprises a Val-Cit linker.

51. The antibody-drug conjugate of claim 50, wherein the antibody is conjugated to MMAE via a linker unit that has the formula: -$A_a$-$W_w$—$Y_y$—; wherein -A- is a stretcher unit, a is 0 or 1; —W— is an amino acid unit, w is an integer ranging from 0 to 12; and —Y— is a spacer unit, y is 0, 1, or 2.

52. The antibody-drug conjugate of claim 51, wherein the stretcher unit has the structure of Formula I below; wherein the amino acid unit is Val-Cit; and wherein the spacer unit is a p-aminobenzyl alcohol (PAB) group having the structure of Formula II below;

Formula I

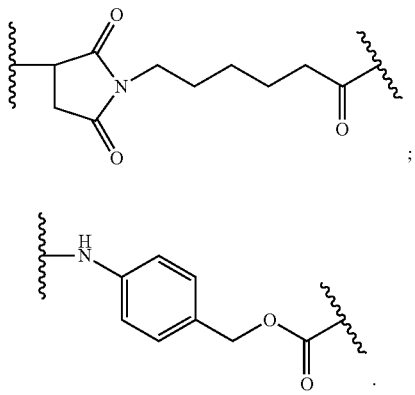

Formula II

53. The antibody-drug conjugate of claim 46, wherein the linker is attached to monomethyl auristatin E and has the structure:

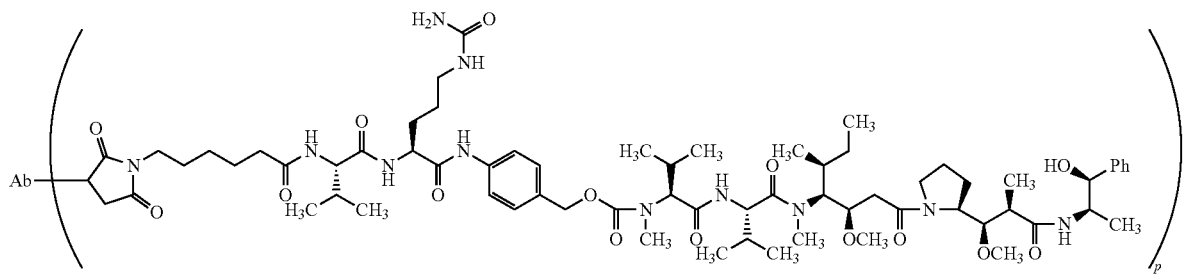

wherein Ab is the antibody and p denotes a number from 1 to 16.

54. The antibody-drug conjugate of claim 53, wherein the average value of p in a population of the antibody-drug conjugates is about 2 to about 5.

55. The antibody-drug conjugate of claim 53, wherein the average value of p in a population of the antibody-drug conjugate is about 4.

56. The method of claim 23, wherein the cancer is esophageal cancer.

57. A method of treating cancer in a subject, the method comprising administering to the subject the antibody-drug conjugate of claim 31.

58. The method of claim 57, wherein the cancer is selected from the group consisting of non-small cell lung cancer (NSCLC), head and neck cancer, esophageal cancer, breast cancer, ovarian cancer, bladder cancer, skin cancer (SCC), ovarian cancer, cervical cancer, gastric cancer, and pancreatic cancer.

59. The method of claim 57, wherein the cancer is non-small cell lung cancer.

60. The method of claim 57, wherein the cancer is head and neck cancer.

61. The method of claim 57, wherein the cancer is esophageal cancer.

62. The method of claim 57, wherein the antibody or antigen-binding fragment or antibody-drug conjugate is in a pharmaceutical composition comprising the antibody-drug conjugate and a pharmaceutically acceptable carrier.

63. The method of claim 57, wherein the subject is a human.

64. The method of claim 57, wherein the antibody-drug conjugate is administered in combination with radiation or a chemotherapeutic agent.

65. A pharmaceutical composition comprising the antibody-drug conjugate of claim 31 and one or more agents selected from the group consisting of a physiologically acceptable carrier, a diluent, and an excipient.

66. A method of treating cancer in a subject, the method comprising administering to the subject the antibody-drug conjugate of claim 34.

67. The method of claim 66, wherein the cancer is selected from the group consisting of non-small cell lung cancer (NSCLC), head and neck cancer, esophageal cancer, breast cancer, ovarian cancer, bladder cancer, skin cancer (SCC), ovarian cancer, cervical cancer, gastric cancer, and pancreatic cancer.

68. The method of claim 66, wherein the cancer is non-small cell lung cancer.

69. The method of claim 66, wherein the cancer is head and neck cancer.

70. The method of claim 66, wherein the cancer is esophageal cancer.

71. The method of claim 66, wherein the antibody or antigen-binding fragment or antibody-drug conjugate is in a pharmaceutical composition comprising the antibody-drug conjugate and a pharmaceutically acceptable carrier.

72. The method of claim 66, wherein the subject is a human.

73. The method of claim 66, wherein the antibody-drug conjugate is administered in combination with radiation or a chemotherapeutic agent.

74. A pharmaceutical composition comprising the antibody-drug conjugate of claim 34 and one or more agents selected from the group consisting of a physiologically acceptable carrier, a diluent, and an excipient.

75. A method of treating cancer in a subject, the method comprising administering to the subject the antibody-drug conjugate of claim 45.

76. The method of claim 75, wherein the cancer is selected from the group consisting of non-small cell lung cancer (NSCLC), head and neck cancer, esophageal cancer, breast cancer, ovarian cancer, bladder cancer, skin cancer (SCC), ovarian cancer, cervical cancer, gastric cancer, and pancreatic cancer.

77. The method of claim 75, wherein the cancer is non-small cell lung cancer.

78. The method of claim 75, wherein the cancer is head and neck cancer.

79. The method of claim 75, wherein the cancer is esophageal cancer.

80. The method of claim 75, wherein the antibody or antigen-binding fragment or antibody-drug conjugate is in a pharmaceutical composition comprising the antibody-drug conjugate and a pharmaceutically acceptable carrier.

81. The method of claim 75, wherein the subject is a human.

82. The method of claim 75, wherein the antibody-drug conjugate is administered in combination with radiation or a chemotherapeutic agent.

83. A pharmaceutical composition comprising the antibody-drug conjugate of claim 45 and one or more agents selected from the group consisting of a physiologically acceptable carrier, a diluent, and an excipient.

84. A method of treating cancer in a subject, the method comprising administering to the subject the antibody-drug conjugate of claim 53.

85. The method of claim 84, wherein the cancer is selected from the group consisting of non-small cell lung cancer (NSCLC), head and neck cancer, esophageal cancer, breast cancer, ovarian cancer, bladder cancer, skin cancer (SCC), ovarian cancer, cervical cancer, gastric cancer, and pancreatic cancer.

86. The method of claim 84, wherein the cancer is non-small cell lung cancer.

87. The method of claim 84, wherein the cancer is head and neck cancer.

88. The method of claim 84, wherein the cancer is esophageal cancer.

89. The method of claim 84, wherein the antibody or antigen-binding fragment or antibody-drug conjugate is in a pharmaceutical composition comprising the antibody-drug conjugate and a pharmaceutically acceptable carrier.

90. The method of claim 84, wherein the subject is a human.

91. The method of claim 84, wherein the antibody-drug conjugate is administered in combination with radiation or a chemotherapeutic agent.

92. A pharmaceutical composition comprising the antibody-drug conjugate of claim 53 and one or more agents selected from the group consisting of a physiologically acceptable carrier, a diluent, and an excipient.

93. An antibody-drug conjugate comprising an anti-αvβ6 antibody, or antigen-binding fragment thereof, comprising a heavy chain variable region and a light chain variable region, wherein the heavy chain variable region comprises:
   (i) a CDR-H1 comprising the amino acid sequence of SEQ ID NO:31;
   (ii) a CDR-H2 comprising the amino acid sequence of SEQ ID NO:32; and
   (iii) a CDR-H3 comprising the amino acid sequence of SEQ ID NO:33; and
wherein the light chain variable region comprises:
   (i) a CDR-L1 comprising the amino acid sequence of SEQ ID NO:37;
   (ii) a CDR-L2 comprising the amino acid sequence of SEQ ID NO:42; and
   (iii) a CDR-L3 comprising the amino acid sequence of SEQ ID NO:39
wherein the CDRs are determined by Kabat, conjugated to a cytotoxic or cytostatic agent via a linker, wherein the linker is attached to monomethyl auristatin E, and the antibody-drug conjugate has the structure:

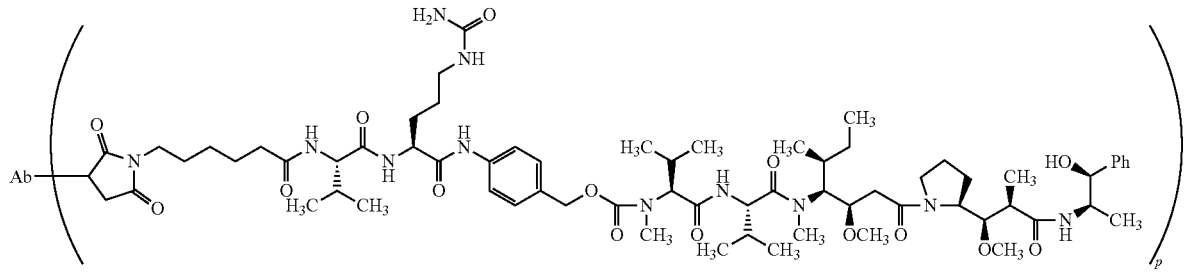

wherein Ab is the antibody or antigen-binding fragment and the average value of p in a population of the antibody-drug conjugate is about 2 to about 5.

94. An antibody-drug conjugate comprising an anti-αvβ6 antibody, or antigen-binding fragment thereof, comprising a heavy chain variable region and a light chain variable region, wherein the heavy chain variable region comprises the amino acid sequence of SEQ ID NO: 6 and the light chain variable region comprises the amino acid sequence of SEQ ID NO:17, conjugated to a cytotoxic or cytostatic agent via a linker, wherein the linker is attached to monomethyl auristatin E and the antibody-drug conjugate has the structure:

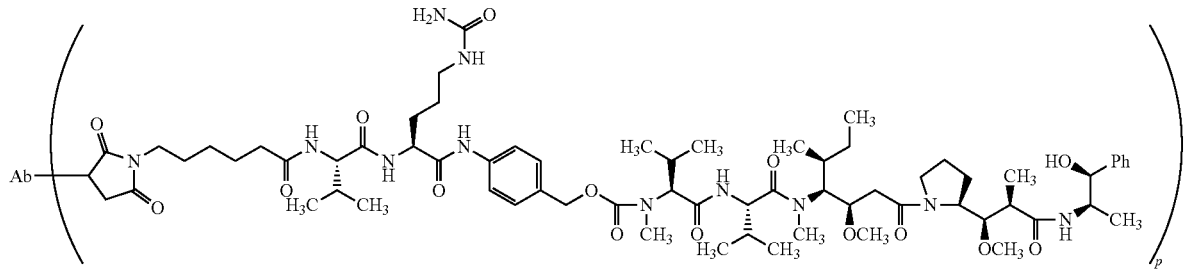

wherein Ab is the antibody or antigen-binding fragment and the average value of p in a population of the antibody-drug conjugate is about 2 to about 5.

95. An antibody-drug conjugate comprising an anti-αvβ6 antibody, or antigen-binding fragment thereof, comprising a heavy chain and a light chain, wherein the heavy chain has an amino acid sequence comprising SEQ ID NO:21 and the light chain has an amino acid sequence comprising SEQ ID NO:29, conjugated to a cytotoxic or cytostatic agent via a linker, wherein the linker is attached to monomethyl auristatin E and the antibody-drug conjugate has the structure:

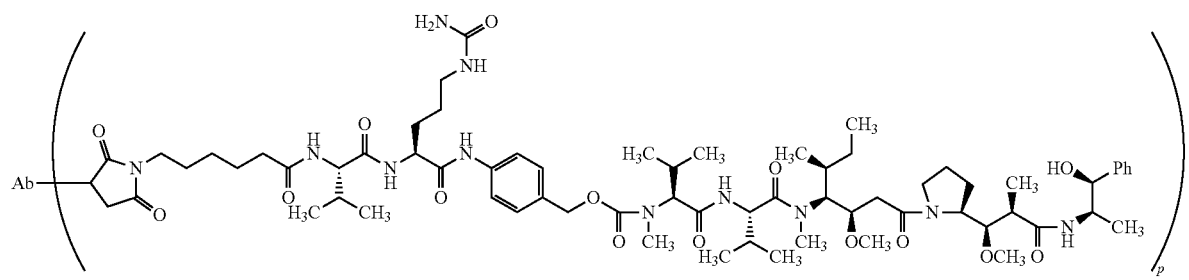

wherein Ab is the antibody or antigen-binding fragment and the average value of p in a population of the antibody-drug conjugate is about 2 to about 5.

96. A method of treating cancer in a human subject, the method comprising administering to the subject the antibody-drug conjugate comprising an anti-αvβ6 antibody, or antigen-binding fragment thereof, comprising a heavy chain variable region and a light chain variable region, wherein the heavy chain variable region comprises:
(i) a CDR-H1 comprising the amino acid sequence of SEQ ID NO:31;
(ii) a CDR-H2 comprising the amino acid sequence of SEQ ID NO:32; and
(iii) a CDR-H3 comprising the amino acid sequence of SEQ ID NO:33; and
wherein the light chain variable region comprises:
(i) a CDR-L1 comprising the amino acid sequence of SEQ ID NO:37;
(ii) a CDR-L2 comprising the amino acid sequence of SEQ ID NO:42; and
(iii) a CDR-L3 comprising the amino acid sequence of SEQ ID NO:39
wherein the CDRs are determined by Kabat, conjugated to a cytotoxic or cytostatic agent via a linker, wherein the linker is attached to monomethyl auristatin E, and the antibody-drug conjugate has the structure:

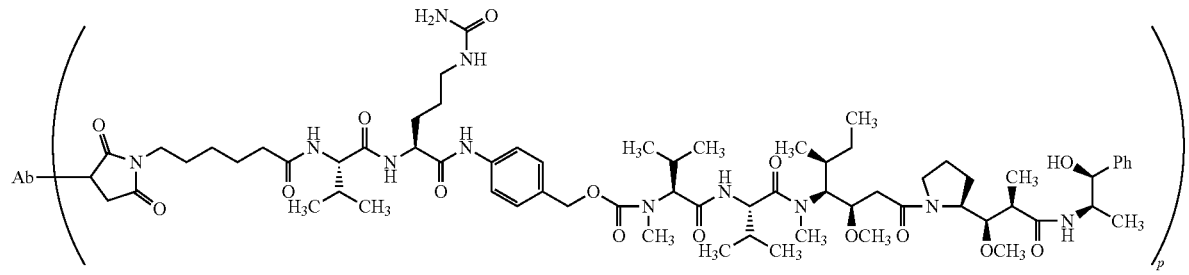

wherein Ab is the antibody or antigen-binding fragment and the average value of p in a population of the antibody-drug conjugate is about 2 to about 5.

97. The method of claim 96, wherein the average value of p in a population of the antibody-drug conjugate is about 4.

98. The method of claim 96, wherein the cancer is selected from the group consisting of non-small cell lung cancer (NSCLC), head and neck cancer, esophageal cancer, breast cancer, ovarian cancer, bladder cancer, skin cancer (SCC), ovarian cancer, cervical cancer, gastric cancer, and pancreatic cancer.

99. A method of treating cancer in a human subject, the method comprising administering to the subject the antibody-drug conjugate comprising an anti-αvβ6 antibody, or antigen-binding fragment thereof, comprising a heavy chain variable region and a light chain variable region, wherein the heavy chain variable region comprises the amino acid sequence of SEQ ID NO: 6 and the light chain variable region comprises the amino acid sequence of SEQ ID NO:17, conjugated to a cytotoxic or cytostatic agent via a linker, wherein the linker is attached to monomethyl auristatin E and the antibody-drug conjugate has the structure:

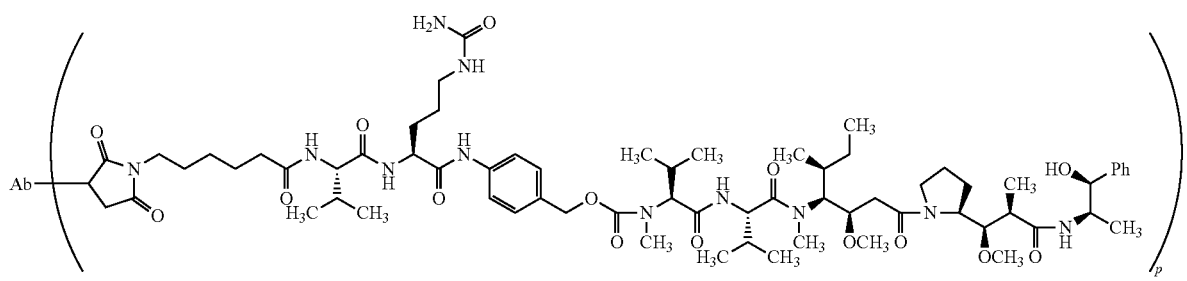

wherein Ab is the antibody or antigen-binding fragment and the average value of p in a population of the antibody-drug conjugate is about 2 to about 5.

100. The method of claim 99, wherein the average value of p in a population of the antibody-drug conjugate is about 4.

101. The method of claim 99, wherein the cancer is selected from the group consisting of non-small cell lung cancer (NSCLC), head and neck cancer, esophageal cancer, breast cancer, ovarian cancer, bladder cancer, skin cancer (SCC), ovarian cancer, cervical cancer, gastric cancer, and pancreatic cancer.

102. A method of treating cancer in a human subject, the method comprising administering to the subject the antibody-drug conjugate comprising an anti-αvβ6 antibody, or antigen-binding fragment thereof, comprising a heavy chain and a light chain, wherein the heavy chain has an amino acid sequence comprising SEQ ID NO:21 and the light chain has an amino acid sequence comprising SEQ ID NO:29, conjugated to a cytotoxic or cytostatic agent via a linker, wherein the linker is attached to monomethyl auristatin E and the antibody-drug conjugate has the structure:

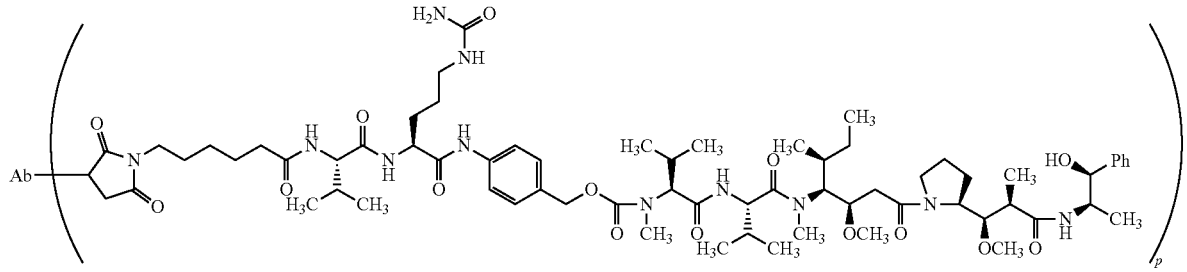

wherein Ab is the antibody or antigen-binding fragment and the average value of p in a population of the antibody-drug conjugate is about 2 to about 5.

103. The method of claim 102, wherein the average value of p in a population of the antibody-drug conjugate is about 4.

104. The method of claim 102, wherein the cancer is selected from the group consisting of non-small cell lung cancer (NSCLC), head and neck cancer, esophageal cancer, breast cancer, ovarian cancer, bladder cancer, skin cancer (SCC), ovarian cancer, cervical cancer, gastric cancer, and pancreatic cancer.

* * * * *